US010980862B2

(12) United States Patent
Hattersley et al.

(10) Patent No.: US 10,980,862 B2
(45) Date of Patent: Apr. 20, 2021

(54) FORMULATIONS OF ABALOPARATIDE, TRANSDERMAL PATCHES THEREOF, AND USES THEREOF

(71) Applicants: Radius Health, Inc., Boston, MA (US); Kindeva Drug Delivery L.P., St. Paul, MN (US)

(72) Inventors: Gary Hattersley, Stow, MA (US); Alan Harris, New York City, NY (US); Jamal Saeh, Belmont, MA (US); Ehab Hamed, Lexington, MA (US); Kenneth Brown, Inver Grove Heights, MN (US); Daniel Dohmeier, White Bear Lake, MN (US); Joan Moseman, Lake Elmo, MN (US); Ying Zhang, Woodbury, MN (US); Lisa Dick, Afton, MN (US)

(73) Assignees: Radius Health, Inc., Boston, MA (US); Kindeva Drug Delivery L.P., St. Paul, MN (US)

(*) Notice: Subject to any disclaimer, the term of this patent is extended or adjusted under 35 U.S.C. 154(b) by 0 days.

(21) Appl. No.: 16/733,779

(22) Filed: Jan. 3, 2020

(65) Prior Publication Data
US 2020/0164045 A1 May 28, 2020

Related U.S. Application Data
(63) Continuation of application No. 16/092,587, filed as application No. PCT/US2017/026462 on Apr. 6, (Continued)

(51) Int. Cl.
A61K 38/29 (2006.01)
A61K 9/70 (2006.01)
(Continued)

(52) U.S. Cl.
CPC ............ *A61K 38/29* (2013.01); *A61K 9/0014* (2013.01); *A61K 9/0021* (2013.01); *A61K 9/703* (2013.01);
(Continued)

(58) Field of Classification Search
CPC ........ A61K 38/20; A61K 33/06; A61K 33/30; A61K 9/0021; A61K 9/703; A61K 47/10; A61K 38/29; A61P 19/02; A61P 19/10
See application file for complete search history.

(56) References Cited

U.S. PATENT DOCUMENTS 5,589,452 A 12/1996 Krstenansky et al.
6,583,114 B2 6/2003 Vickery
(Continued)

FOREIGN PATENT DOCUMENTS

WO 2009137093 * 11/2009
WO 2009139093 * 11/2009
(Continued)

OTHER PUBLICATIONS

Yates et al, A Transdermal Patch Delivering the PTHrP1-34 Analog, Abaloparatide, Dose-Dependently Increases Spine and Hip BMD Compared to Placebo , Osteoporosis Clinical Trials, Endocrine Society. (Year: 2014).*
(Continued)

*Primary Examiner* — Carlos A Azpuru
(74) *Attorney, Agent, or Firm* — Womble Bond Dickinson (US) LLP; Danielle L. Herritt

(57) ABSTRACT

Disclosed are abaloparatide formulations for transdermal delivery of a therapeutically effective amount of abaloparatide, as well as transdermal patches prepared using these formulations, methods of preparing the disclosed formulations and patches, and methods of using these formulations and patches to treat osteoporosis, osteopenia,
(Continued)

osteoarthritis, and/or bone fracture, improve bone mineral density (BMD), improve trabecular bone score (TBS), and treat, prevent, and/or reduce bone fractures.

18 Claims, 35 Drawing Sheets

Related U.S. Application Data 2017, now Pat. No. 10,568,937, which is a continuation-in-part of application No. PCT/US2016/056196, filed on Oct. 8, 2016.

(60) Provisional application No. 62/479,250, filed on Mar. 30, 2017, provisional application No. 62/396,196, filed on Sep. 18, 2016, provisional application No. 62/353,249, filed on Jun. 22, 2016, provisional application No. 62/324,336, filed on Apr. 18, 2016.

(51) Int. Cl.

| | |
|---|---|
| A61P 19/02 | (2006.01) |
| A61P 19/10 | (2006.01) |
| A61K 9/00 | (2006.01) |
| A61K 33/06 | (2006.01) |
| A61K 33/30 | (2006.01) |
| A61K 47/10 | (2017.01) |

(52) U.S. Cl.
CPC ............. *A61K 33/06* (2013.01); *A61K 33/30* (2013.01); *A61K 47/10* (2013.01); *A61P 19/02* (2018.01); *A61P 19/10* (2018.01)

(56) References Cited

U.S. PATENT DOCUMENTS

| | | | |
|---|---|---|---|
| 6,881,203 | B2 | 4/2005 | Delmore et al. |
| 7,537,795 | B2 | 5/2009 | Cormier et al. |
| 7,556,821 | B2 | 7/2009 | Ameri et al. |
| 7,579,013 | B2 | 8/2009 | Ameri et al. |
| 7,803,770 | B2 | 9/2010 | Dey et al. |
| 7,963,935 | B2 | 6/2011 | Cormier et al. |
| 8,148,333 | B2 | 4/2012 | Dey et al. |
| 8,361,022 | B2 | 1/2013 | Ameri et al. |
| 8,632,801 | B2 | 1/2014 | Ameri et al. |
| 8,633,159 | B2 | 1/2014 | Ameri et al. |
| 8,663,155 | B2 | 3/2014 | Cormier et al. |
| 8,741,377 | B2 | 6/2014 | Choi et al. |
| 8,748,382 | B2 | 6/2014 | Dey et al. |
| 8,920,817 | B2 | 12/2014 | Ameri et al. |
| 9,295,714 | B2 | 3/2016 | Ameri et al. |
| 9,339,956 | B2 | 5/2016 | Rendon |
| 9,573,717 | B2 | 2/2017 | Ameri et al. |
| 9,775,799 | B2 | 10/2017 | Sugahara et al. |
| 10,232,158 | B2 | 3/2019 | Quan et al. |
| 2004/0049150 | A1 | 3/2004 | Dalton et al. |
| 2004/0265354 | A1 | 12/2004 | Ameri et al. |
| 2005/0009739 | A1 | 1/2005 | Wang et al. |
| 2005/0032698 | A1* | 2/2005 | Day ....................... A61K 45/06 514/11.8 |
| 2005/0261631 | A1 | 11/2005 | Clarke et al. |
| 2006/0094642 | A1 | 5/2006 | Gaich et al. |
| 2006/0195067 | A1 | 8/2006 | Wolter et al. |
| 2006/0211608 | A1 | 9/2006 | Holick |
| 2007/0270341 | A1 | 11/2007 | Morley et al. |
| 2008/0039775 | A1 | 2/2008 | Ameri et al. |
| 2009/0016935 | A1 | 1/2009 | Andrianov et al. |
| 2010/0029556 | A1 | 2/2010 | Dey et al. |
| 2011/0281790 | A1 | 11/2011 | Pohl et al. |
| 2013/0006217 | A1 | 1/2013 | Hattersley et al. |
| 2013/0041330 | A1 | 2/2013 | Matsudo et al. |
| 2014/0046293 | A1 | 2/2014 | Hattersley et al. |
| 2014/0228293 | A1 | 8/2014 | Danishefsky et al. |
| 2014/0330198 | A1 | 11/2014 | Zhang et al. |
| 2014/0343499 | A1 | 11/2014 | Zhang et al. |
| 2017/0065682 | A1 | 3/2017 | Hattersley |
| 2017/0135951 | A1 | 5/2017 | Ameri et al. |
| 2017/0368148 | A1 | 12/2017 | Hattersley |
| 2018/0289615 | A1 | 10/2018 | Brown et al. |
| 2019/0091138 | A1 | 3/2019 | Hattersley et al. |
| 2019/0117739 | A1 | 4/2019 | Hattersley et al. |

FOREIGN PATENT DOCUMENTS

| | | |
|---|---|---|
| WO | WO-2009137093 A1 | 11/2009 |
| WO | WO-2010059605 | 5/2010 |
| WO | WO-2010117602 | 10/2010 |
| WO | WO-2014105508 A1 | 7/2014 |
| WO | WO-2016055550 A1 | 4/2016 |
| WO | WO-2017/062922 A1 | 4/2017 |
| WO | WO-2017060500 A1 | 4/2017 |
| WO | WO-2017184355 A1 | 10/2017 |

OTHER PUBLICATIONS

Alkalani et al, Transdermal Drug Delivery: Innovative Pharmaceutical Developments Based on Disruption of the Barrier Properties of the Stratum Corneum, Pharmaceutics: (4) (Year: 2015).*
U.S. Appl. No. 16/297,280.
U.S. Appl. No. 16/667,850.
Extended European Search Report issued by the European Patent Office Related to European Patent Application EP16854524.2, dated May, 29, 2019.
Hattersley, et.al., "Transdermal Delivery of BA058, a novel analog of hPTHrP (1-34), With a Short Wear Time Patch in Preclinical and Clinical Studies," Bone Abstracts, May 2013.
Shirkhanzadeh, et.al., "Microneedles Coated with Porous Calcium Phosphate Ceramics: Effective Vehicle for Transdermal Delivery of Solid Trehalose," Journal of Material Science: Materials in Medicine, vol. 16, No. 1, Jan. 1, 2005.
Ameri, M., et al., "Demonstrated Solid-State Stability of Parathyroid Hormone PTH(134) Coated on a Novel Transdermal Microprojection Delivery System" Pharmaceutical Research, vol. 26 Issue 11 (Nov. 2009): pp. 2454-2463.
Yates, J., et al., "A Transdermal Patch Delivering the PTHrP1-34 Analog, Abaloparatide, Dose-Dependently Increases Spine and Hip BMD Compared to Placebo." Osteoporosis-Clinical Trials, Endocrine Society. Jun. 2014.
International Search Report and Written Opinion related to PCT/US1656196, dated Dec. 23, 2016.
International Search Report and Written Opinion related to PCTUS2017026462, dated Jun. 6, 2017.
International Preliminary Report on Patentablity related to PCTUS2016055924, dated Apr. 10, 2018.
International Preliminary Report on Patentablity related to PCTUS2017026462, dated Oct. 23, 2018.
International Preliminary Report on Patentablity related to PCTUS2016056196, dated Apr. 10, 2018.
International Search Report and Written Opinion related to PCTUS0160555924, dated Apr. 13, 2017.
TYMLOS (abaloparatide) injection Label (Approval 2017)—Dated Apr. 28, 2017.
TYMLOS (abaloparatide) injection Label (Approval 2017)—Dated Oct. 17, 2017.
Labeling Regulatory Requirements for Medical Devices, 53 pages (1989).
Osteoporosis Fact Sheet; retrieved from: http://report.nih.gov/nihfactsheets/Pdfs/Osteoporosis(NIAMS).pdf, 2 pages (2010).
Apenberg, P., et al., "Teriparatide for Acceleration of Fracture Repair in Humans: A Prospective, Randomized, Double-Blind Study of 102 Postmenopausal Women With Distal Radial Fractures" Journal of Bone and Mineral Research, vol. 25, No. 2, Feb. 2010, pp. 404-414.
Shi, Z., et al., "Effectiveness of Teriparatide on Fracture Healing: A Systematic Review and Meta-Analysis" PLoS ONE 11(12): e0168691, Dec. 20, 2016, 13 pages.

(56) References Cited

OTHER PUBLICATIONS

Lou, S., et al., "The Effect of Teriparatide on Fracture Healing of Osteoporotic Patients: A Meta-Analysis of Randomized Controlled Trials" Hindawl Publishing Corporation, BioMed Research International, vol. 2016, Article ID 6040379, 10 pages.

Extended European Search Report issued by the European Patent Office Related to European Patent Application No. EP17786338.8, dated Apr. 4, 2020.

NCT01674721: Phase 2 Study of BA058 (Abaloparatide) Transdermal Delivery in Postmenopausal Women with Osteoporosis (2014).

* cited by examiner

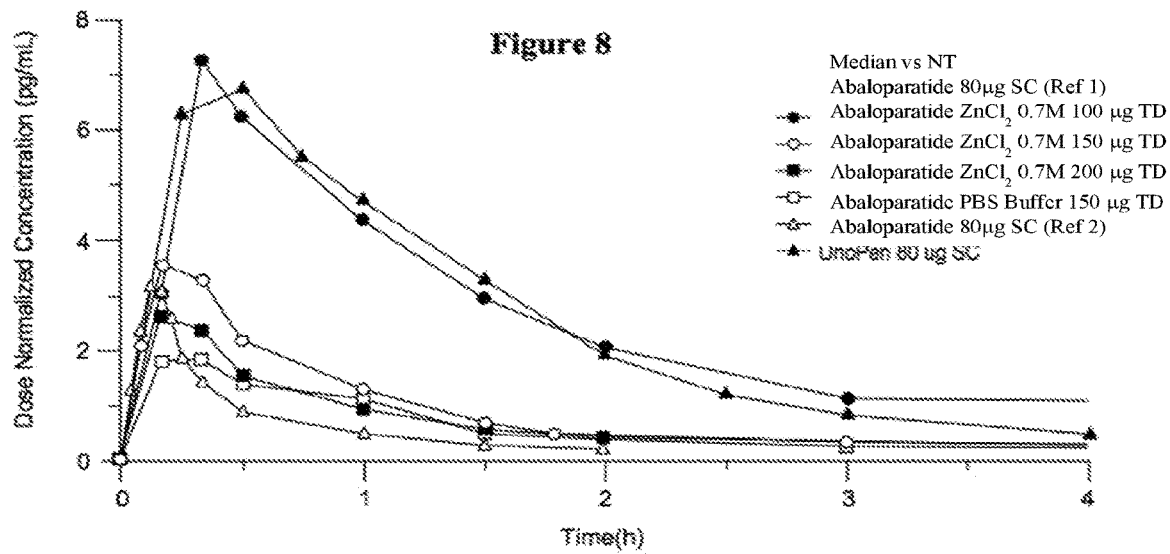
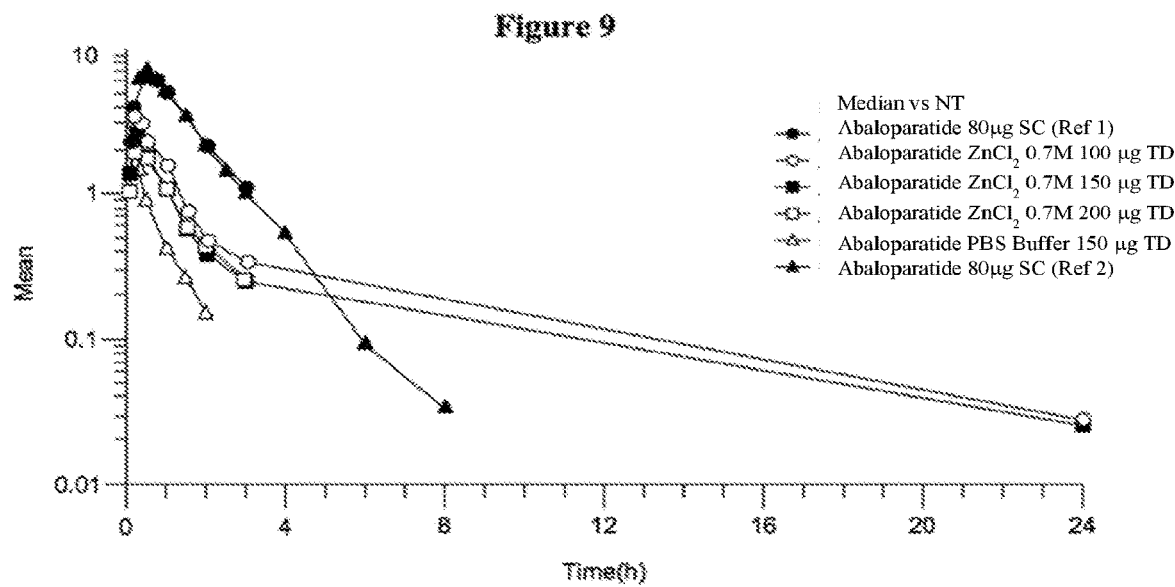

Lumbar spine BMD (mITT population, N = 231)

Total Hip BMD (mITT population, N = 231)

Local Tolerance (Safety population, N = 249)

FORMULATIONS OF ABALOPARATIDE, TRANSDERMAL PATCHES THEREOF, AND USES THEREOF

PRIORITY CLAIM

The present application claims priority to U.S. Provisional Application No. 62/324,336, filed Apr. 18, 2016, U.S. Provisional Application No. 62/353,249, filed Jun. 22, 2016, and U.S. Provisional Application No. 62/396,196, filed Sep. 18, 2016, and International Application No. PCT/US 16/56196, filed Oct. 8, 2016, all of which are incorporated herein by reference in their entirety, including drawings.

INTRODUCTION

Conventionally, osteoporosis is treated by administration of antiresorptive agents to suppress bone resorption. The most common of these treatments is oral or intravenous administration of bisphosphonates. However, an undesirable side effect of bisphosphonate administration is reduced bone formation (MacLean 2008). Anabolic agents provide an alternative to antiresorptives. The only anabolic agent currently available for treatment of osteoporosis is teriparatide (PTH (1-34), Forteo®), a recombinant form of parathyroid hormone (PTH) that acts by a mechanism that involves stimulating new bone formation (along with resorption) and reconstituting internal bone microarchitecture (Recker 2009; Dempster 2012; Ma 2011). The effects of teriparatide on bone mineral density (BMD) are superior to antiresorptive agents at the spine, but its effects at the hip are more modest, and often delayed until the second year of a two-year course of therapy (Leder 2014; Neer 2001).

Parathyroid hormone-related protein (PTHrP; UniProt Accession No. P12272) shares some homology with parathyroid hormone (PTH) at their N-terminal ends, and both proteins bind to the same G-protein coupled receptor, PTH receptor type-1 (PTH1R). Despite a common receptor, PTH primarily acts as an endocrine regulator of calcium homeostasis whereas PTHrP plays a fundamental paracrine role in the mediation of endochondral bone development (Kronenberg 2006). The differential effects of these proteins may be related not only to differential tissue expression, but also to distinct receptor binding properties (Pioszak 2009; Okazaki 2008; Dean 2008). Over the past several years, PTHrP and its secretory forms (PTHrP (1-36), PTHrP (38-94), and osteostatin), as well as analogues thereof, have been investigated as potential treatments for osteoporosis. Subcutaneous injection of PTHrP and its derivatives and analogues has been reported to be effective for treating osteoporosis and/or improving bone healing (Horwitz 2010; Horwitz 2006; Bostrom 2000; Augustine 2013).

Abaloapratide is a PTHrP analogue that is useful for bone and related disorders and therefore, it is desirable to have an alternative delivery route that is both effective for treatment (e.g., a substantial bioequivalence of the subcutaneous delivery of abaloparatide and/or derivatives and analogues thereof) and easy for administration to improve patients' satisfaction and compliance.

SUMMARY OF THE INVENTION

Provided herein in certain embodiments are preparation formulations for use in transdermal delivery of abaloparatide and one or more excipients selected from the group consisting of $Zn^{2+}$ salts (e.g., $ZnCl_2$, $Zn(OAc)_2$, $Zn_3(PO_4)_2$, ZnCitrate, ZnOxalate, etc., or combinations thereof), $Mg^{2+}$ salts (e.g., MgO, MgCitrate, $MgSO_4$, MgOrotate, MgLactate, $MgCO_3$, $MgCl_2$, $Mg(OAc)_2$, etc., or combinations thereof) $Ca^{2+}$ salts (e.g., CaSorbate, CaCitrate, CaAscorbate, $Ca_3(PO_4)_2$, $CaCl_2$, $CaCO_3$, $CaSO_4$, $Ca(OAc)_2$, etc., or combinations thereof), PEG (polyethylene glycol), PVP (polyvinylpyrrolidone), cyclodextrin (CD, e.g., 2-hydroxypropyl-β-cyclodextrin (HPβCD)), salts of carboxylic acids including fatty acids, NaCl and histidine and various combinations thereof. In certain embodiments, the preparation formulation further comprises water for injection, saline or phosphate buffered saline (PBS). The abaloparatide sequence is known in the art and can be described by ([Glu$^{22,25}$, Leu$^{23,28,31}$, Aib$^{29}$, LyS$^{26,30}$]hPTHrP(1-34)NH$_2$.

Provided herein in certain embodiments are methods for treating osteoporosis, treating osteopenia, treating osteoarthritis, improving bone mineral density (BMD), improving trabecular bone score (TBS), and treating, preventing, and reducing bone fractures, improving fracture healing in a subject comprising transdermally administering a therapeutically effective amount of abaloparatide via a transdermal patch comprising at least one microprojections prepared using abaloparatide as disclosed herein. In some embodiments the osteoporosis being treated is postmenopausal osteoporosis. In some embodiments the osteoporosis being treated is glucocorticoid induced osteoporosis. In certain of these embodiments, the preparation formulation is administered via a transdermal patch as disclosed herein. The bone fractures being treated, prevented, or reduced and the bone with improved BMD or TBS may be vertebral or non-vertebral.

BRIEF DESCRIPTION OF DRAWINGS

FIG. 1A: One possible bioequivalence "window" of the abaloparatide-SC treatment, % scale on the vertical axis indicates the plasma abaloparatide concentration represented by % of its own maximum ($C_{max}$), i.e. 100=$C_{max}$, hereinafter referred to as the "normalized plasma concentration. " FIG. 1B: transdermal delivery in monkeys using a preparation formulation of abaloparatide comprising $ZnCl_2$, the vertical axis indicates normalized peptide plasma concentration. FIG. 1C: transdermal delivery using a preparation formulation of abaloparatide comprising PEG.

For FIG. 3 through FIG. 24, sc administration to abdomen, td 150 ug with PBS buffer (×1) only and td with $ZnCl_2$ excipient prepared from a solution comprising about a 0.7 M ("M" is defined throughout as molar ratio of excipient to abaloparatide in the coating solution; eg $ZnCl_2$ to abaloparatide in the coating solution) coating solution with dosage used (about 100, 150 or 200 ug abaloparatide) on patch indicated in legends. TD patches administered to abdomen.

Figure 3:
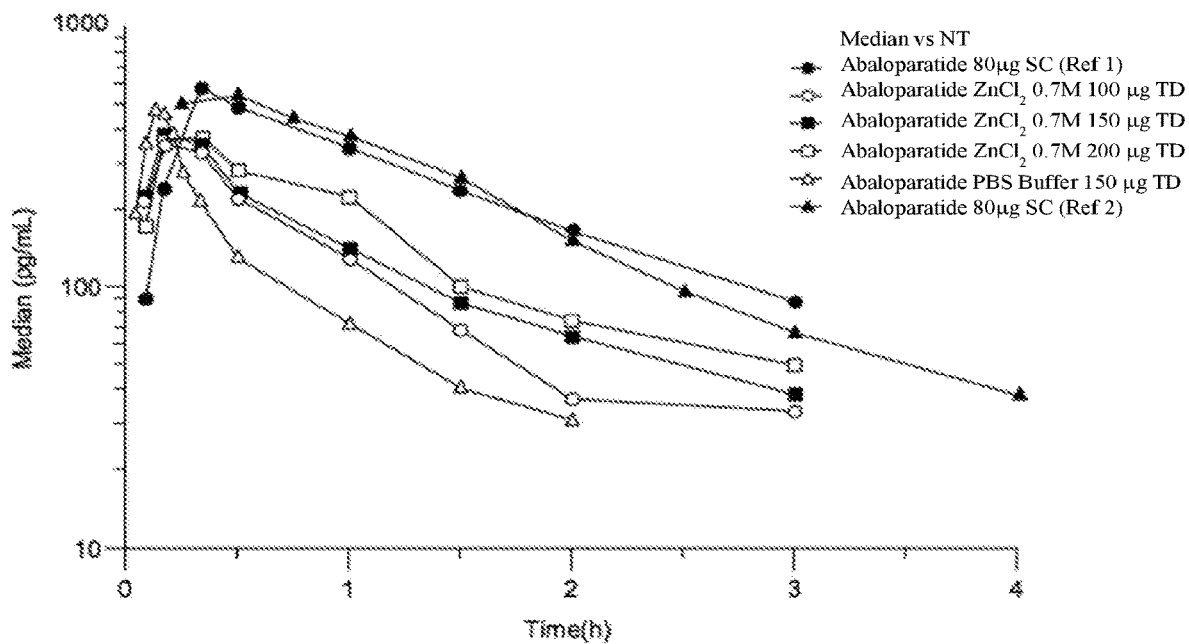

FIG. 3: Pharmacokinetic profile of abaloparatide administered by transdermal (TD) versus subcutaneous (SC) routes, longitude of median plasma abaloparatide concentration v. time post administration in healthy postmenopausal women.

Figure 4:
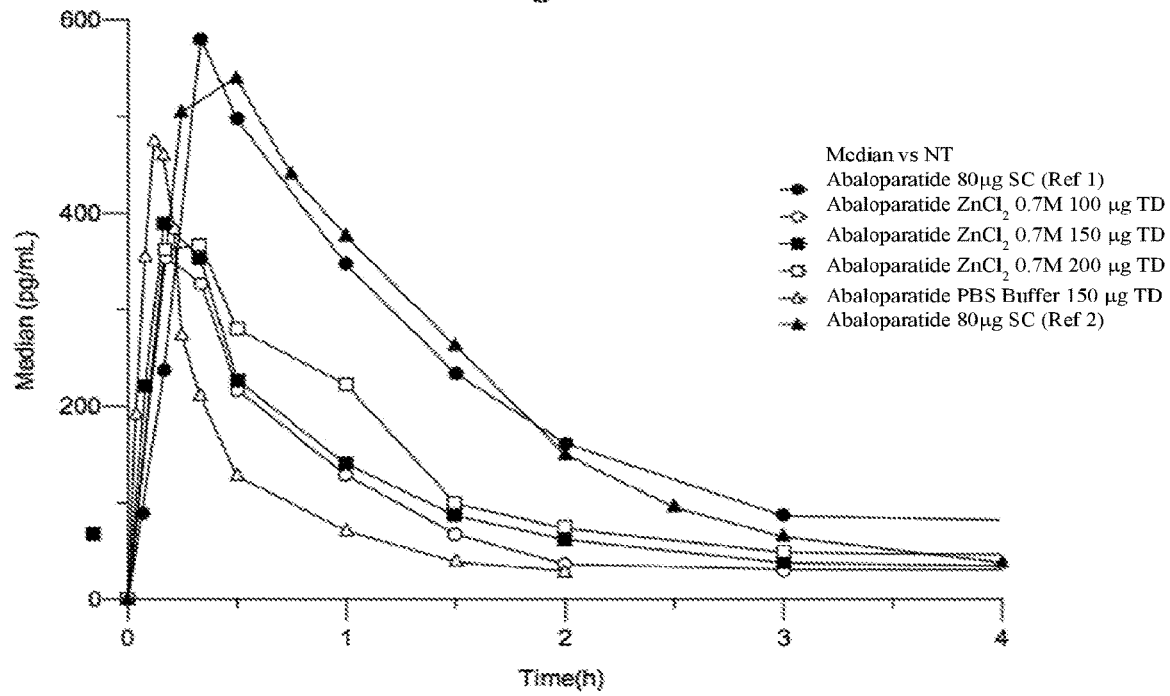

FIG. 4: Pharmacokinetic profile of formulations of abaloparatide administered by transdermal versus subcutaneous routes, median plasma abaloparatide concentration v. time post administration in healthy postmenopausal women.

Figure 5:
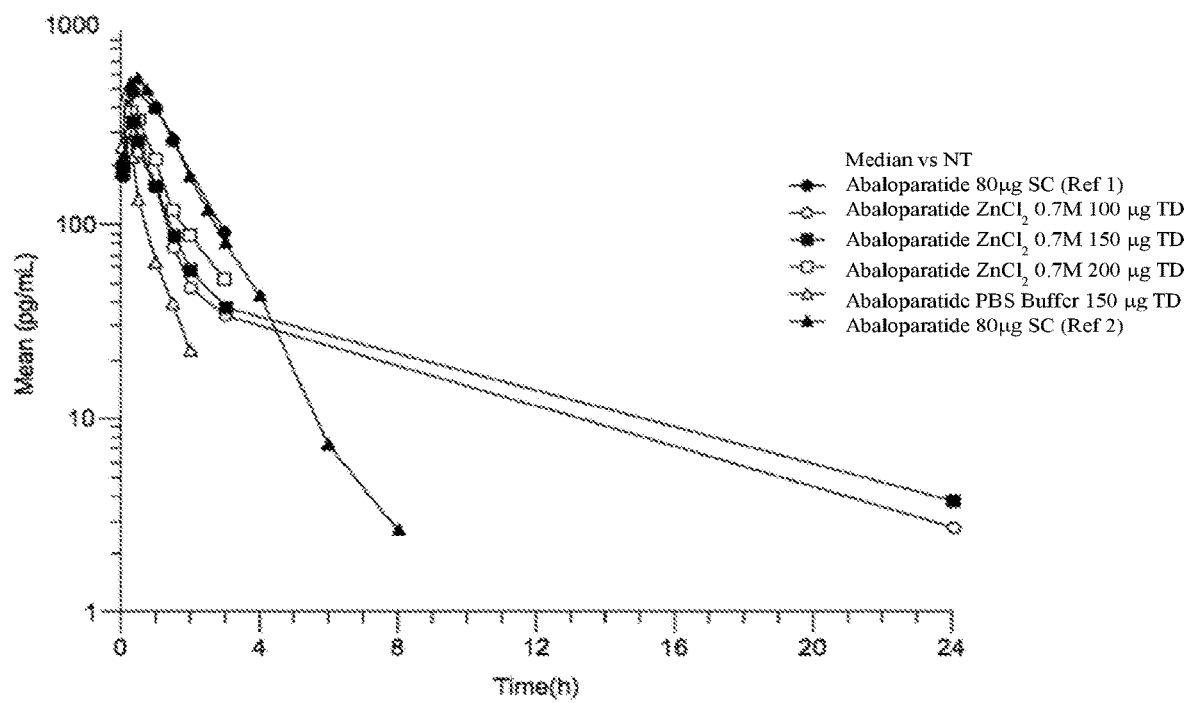

FIG. 5: Pharmacokinetic profile of formulations of abaloparatide administered by transdermal versus subcutaneous routes, longitude of mean plasma abaloparatide concentration v. time post administration in healthy postmenopausal women.

Figure 6:
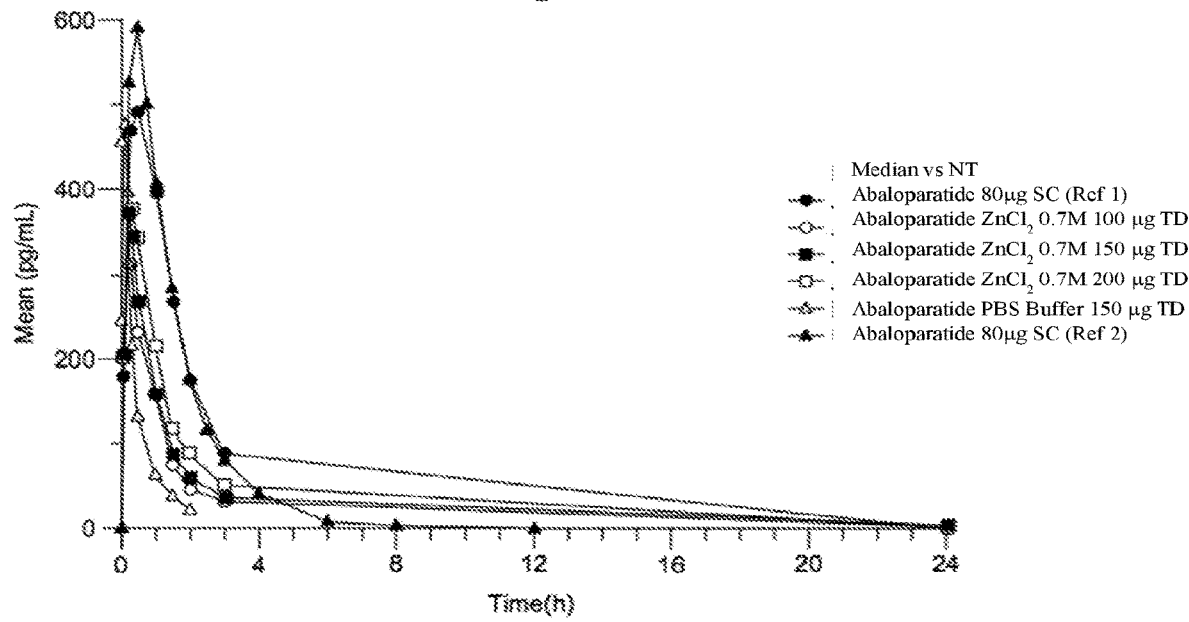

FIG. 6: Pharmacokinetic profile of formulations of abaloparatide administered by transdermal versus subcutaneous routes, mean plasma abaloparatide concentration v. time post administration in healthy postmenopausal women.

Figure 7:
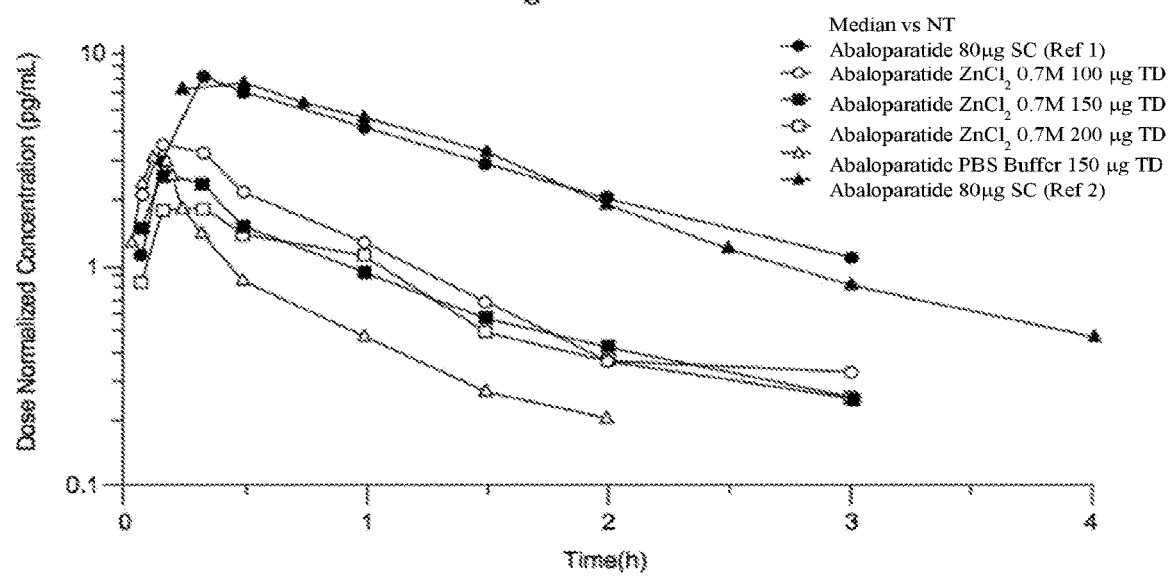

FIG. 7: Pharmacokinetic profile of formulations of abaloparatide administered by transdermal versus subcutaneous routes, longitude of median of dose normalized plasma abaloparatide concentration v. time post administration in healthy postmenopausal women.

FIG. 8: Pharmacokinetic profile of formulations of abaloparatide administered by transdermal versus subcutaneous routes, median of dose normalized plasma abaloparatide concentration v. time post administration in healthy postmenopausal women.

FIG. 9: Pharmacokinetic profile of formulations of abaloparatide administered by transdermal versus subcutaneous routes, longitude of mean of dose normalized plasma abaloparatide concentration v. time post administration.

Figure 10:
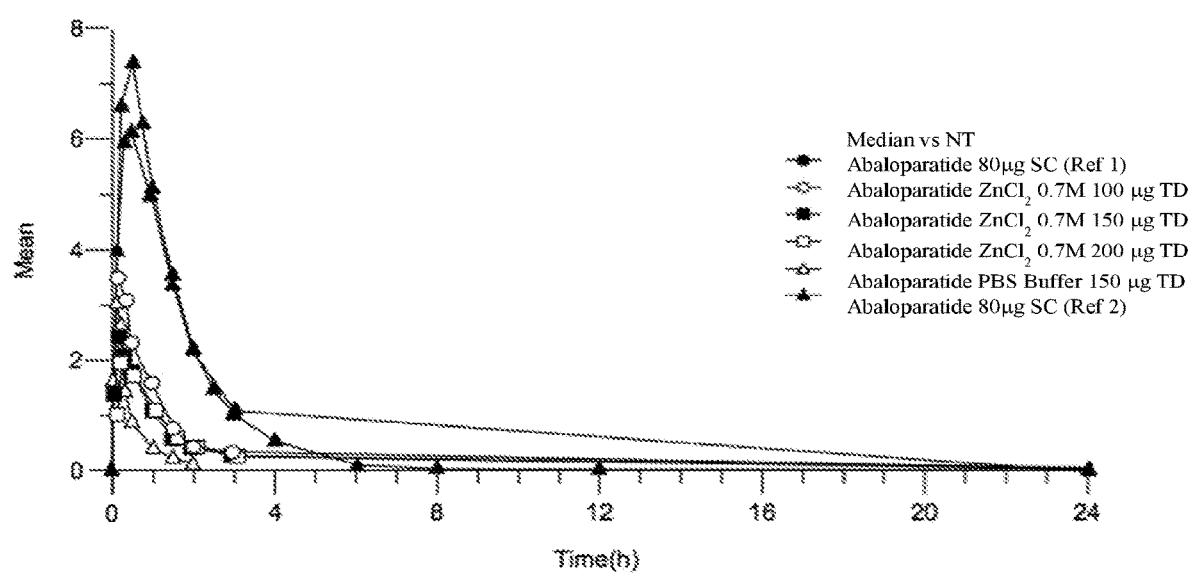

FIG. 10: Pharmacokinetic profile of formulations of abaloparatide administered by transdermal versus subcutaneous routes, mean of dose normalized plasma abaloparatide concentration v. time post administration in healthy postmenopausal women.

Figure 11:
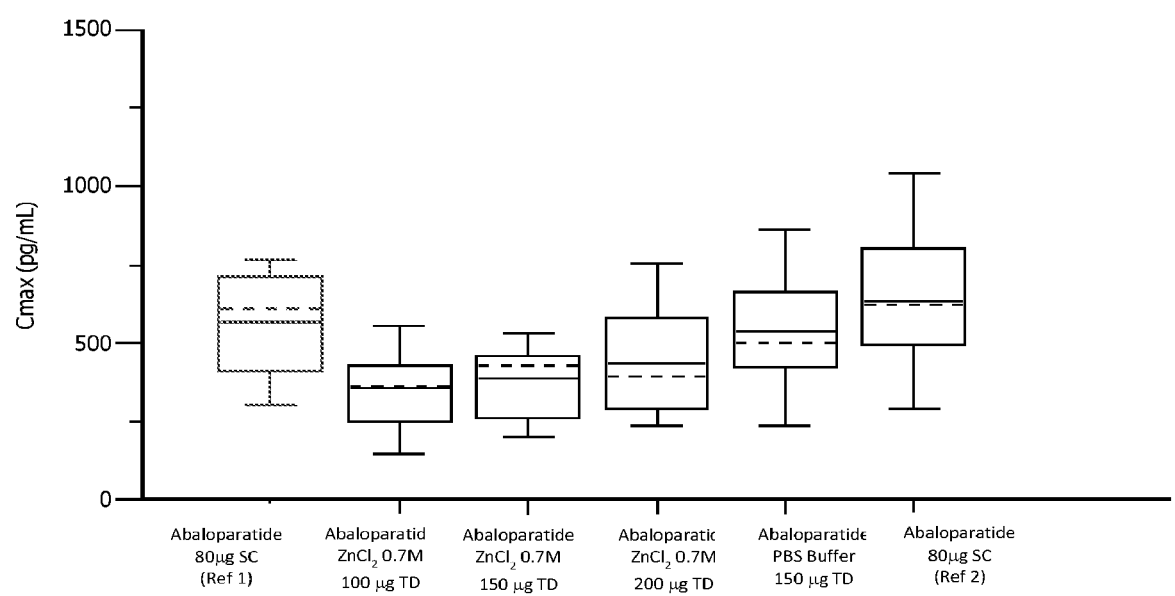

FIG. 11: Comparison of $C_{max}$ of formulations of abaloparatide administered by transdermal versus subcutaneous routes in healthy postmenopausal women.

Figure 12:
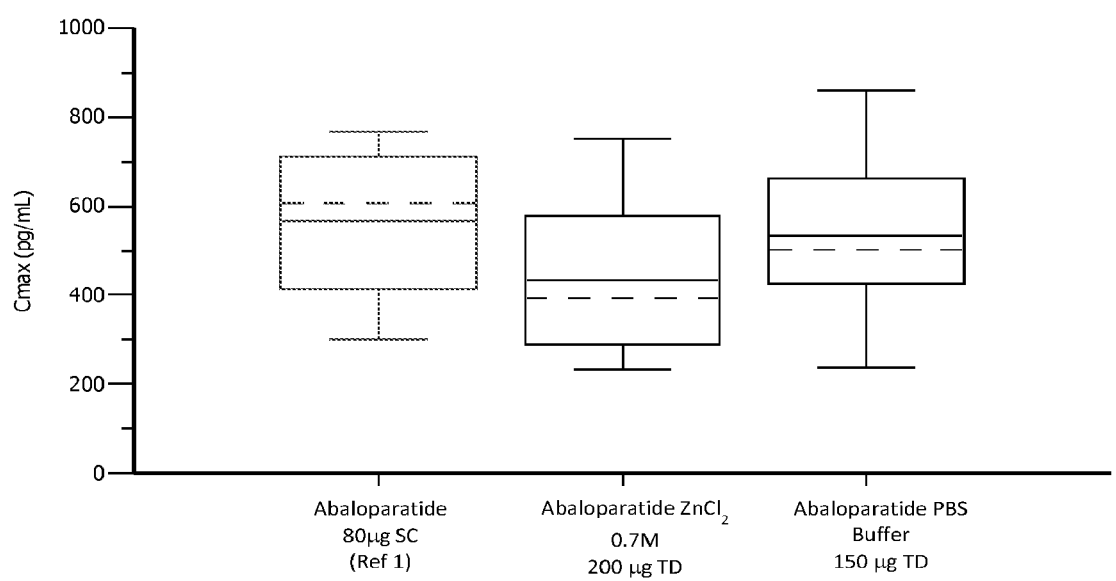

FIG. 12: Comparison of $C_{max}$ of formulations of abaloparatide administered by transdermal versus subcutaneous routes in healthy postmenopausal women.

Figure 13:
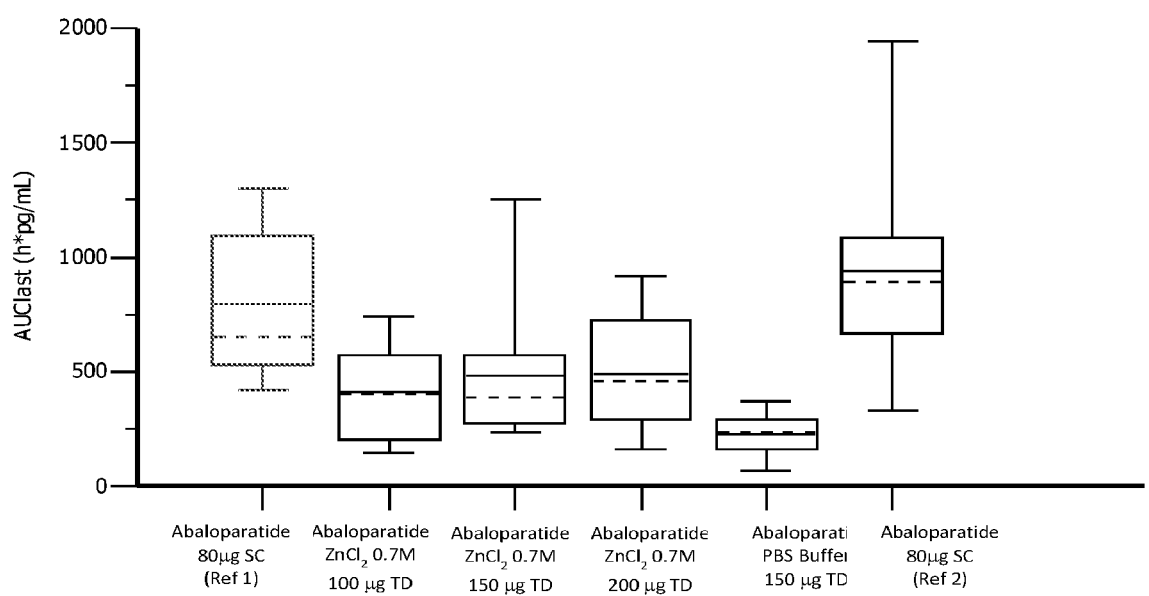

FIG. 13: Comparison of $AUC_{last}$ of formulations of abaloparatide administered by transdermal versus subcutaneous routes in healthy postmenopausal women.

Figure 14:
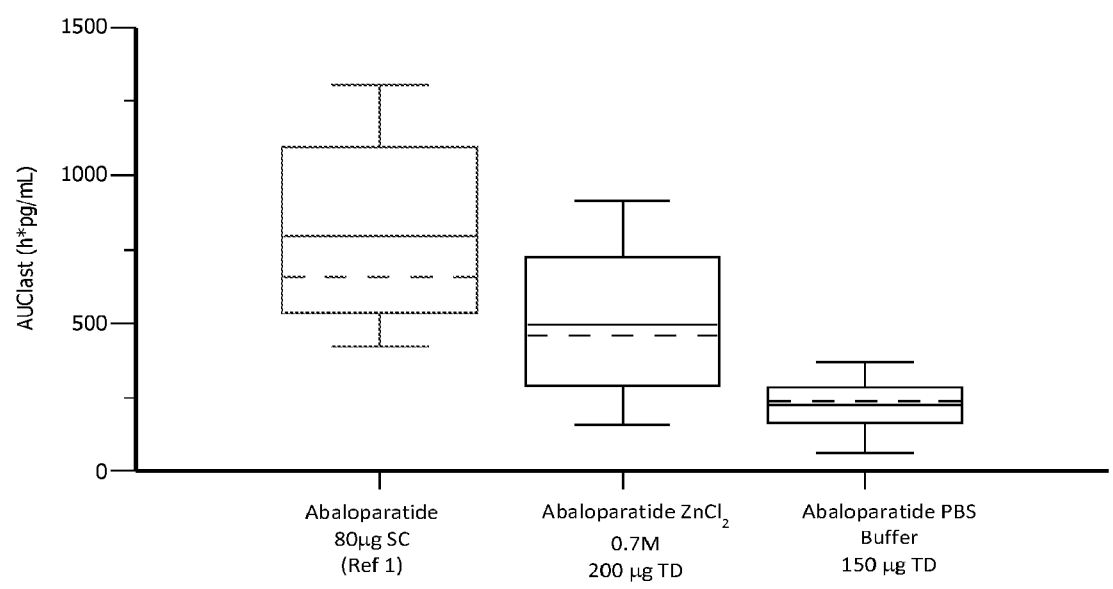

FIG. 14: Comparison of $AUC_{last}$ of formulations of abaloparatide administered by transdermal versus subcutaneous routes in healthy postmenopausal women.

Figure 15:
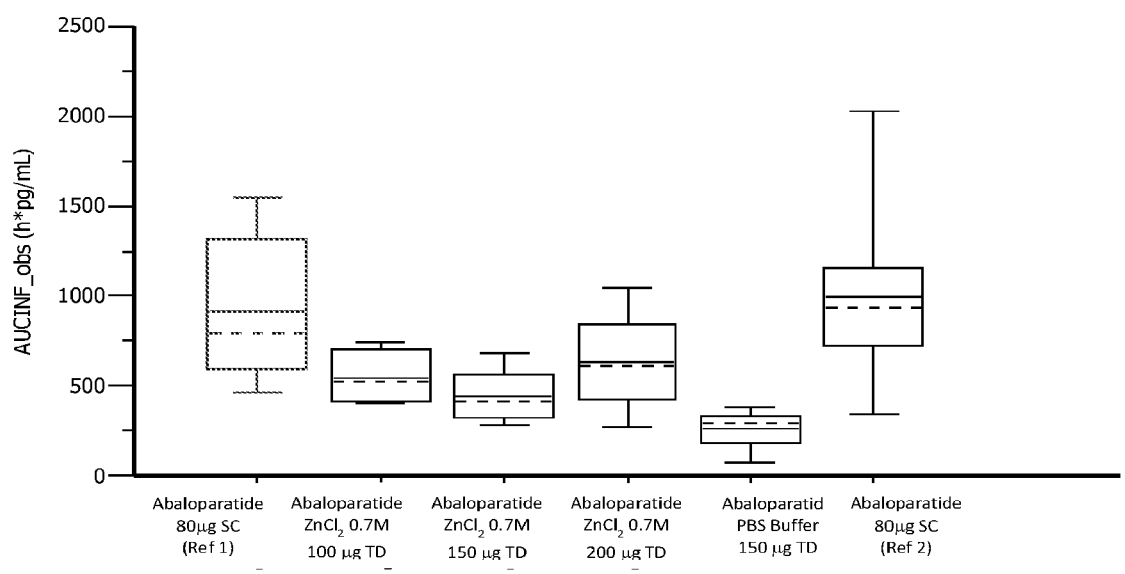

FIG. 15: Comparison of $AUC_{inf}$ of formulations of abaloparatide administered by transdermal versus subcutaneous routes in healthy postmenopausal women.

Figure 16:
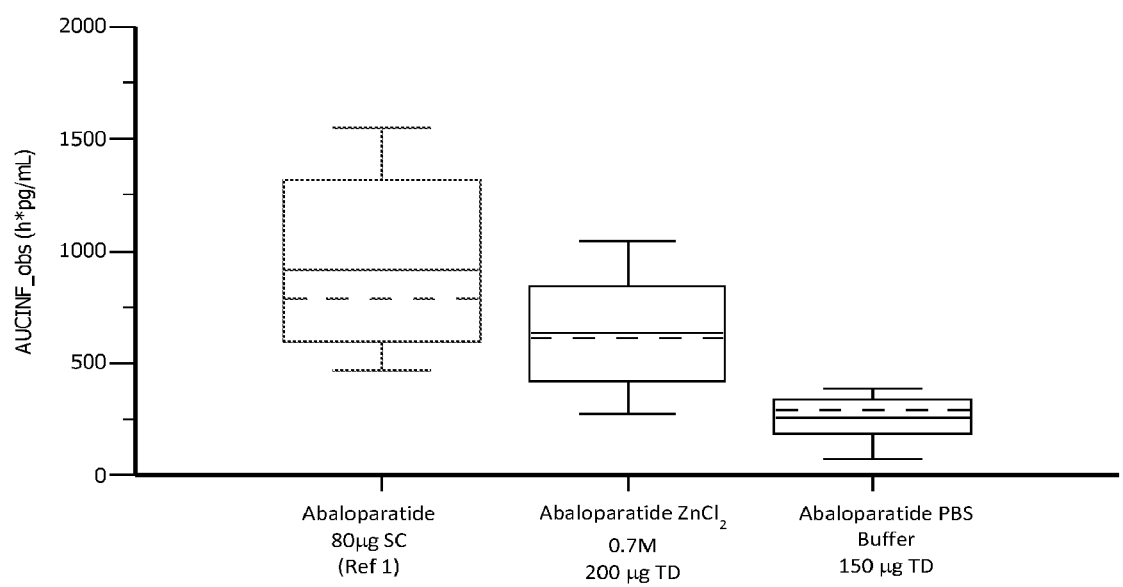

FIG. 16: Comparison of $AUC_{inf}$ of formulations of abaloparatide administered by transdermal versus subcutaneous routes in healthy postmenopausal women.

Figure 17:
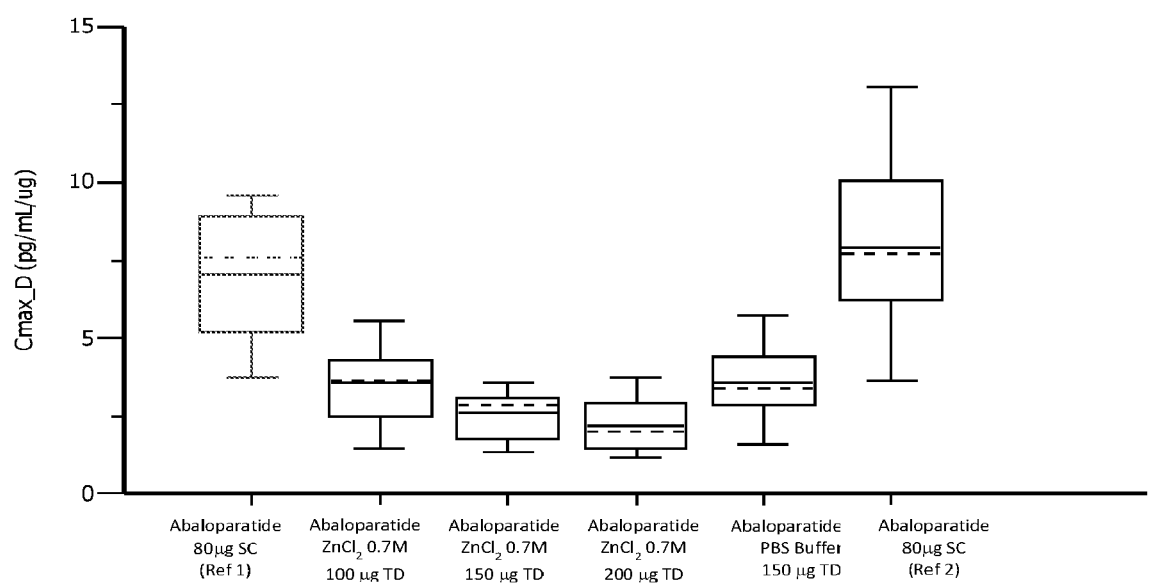

FIG. 17: Comparison of $C_{max}/D$ ($C_{max}$ per dosage) of formulations of abaloparatide administered by transdermal versus subcutaneous routes in healthy postmenopausal women.

Figure 18:
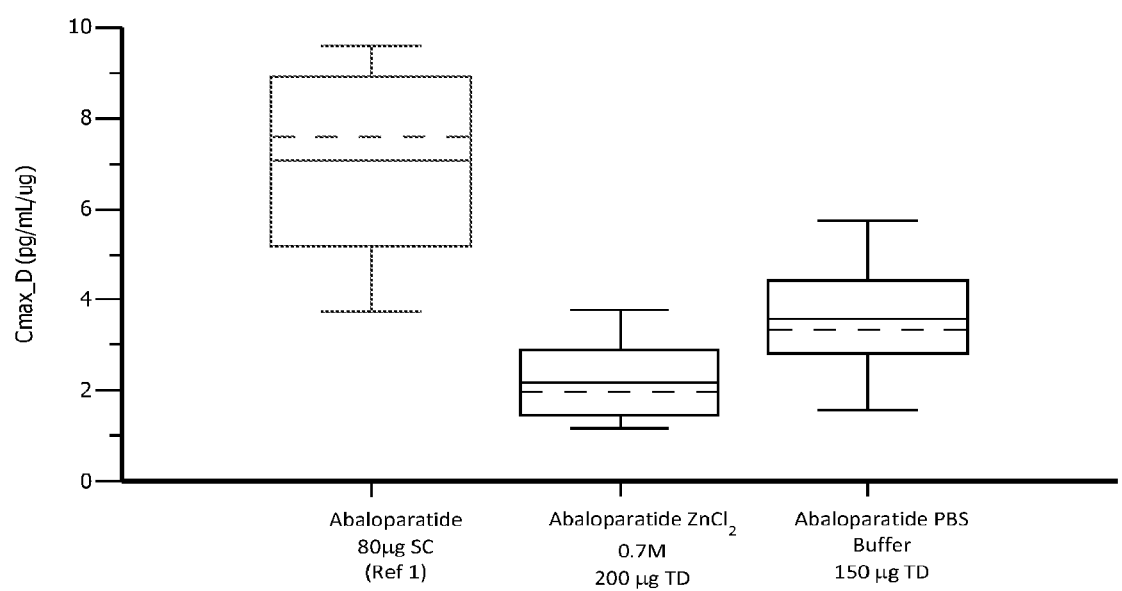

FIG. 18: Comparison of $C_{max}/D$ ($C_{max}$ per dosage) of formulations of abaloparatide administered by transdermal versus subcutaneous routes in healthy postmenopausal women.

Figure 19:
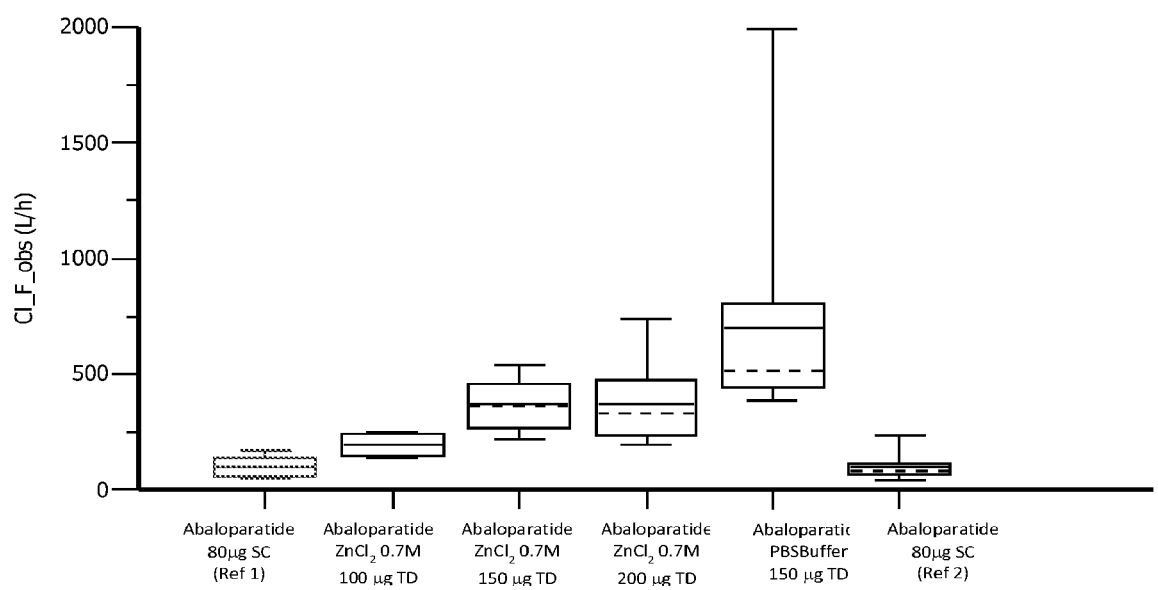

FIG. 19: Comparison of CL/F of formulations of abaloparatide administered by transdermal versus subcutaneous routes in healthy postmenopausal women.

Figure 20:
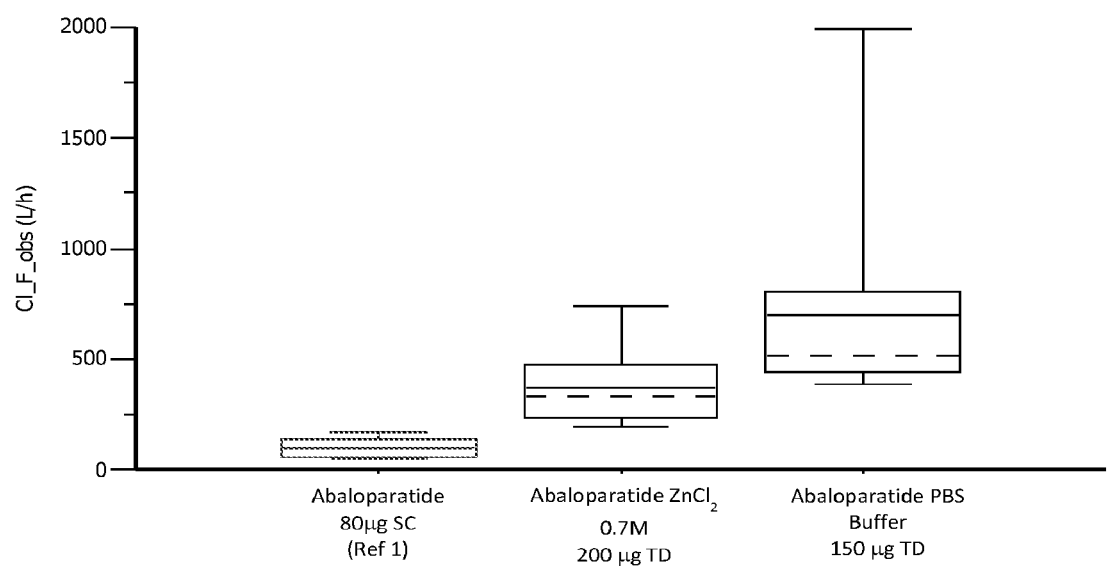

FIG. 20: Comparison of CL/F of formulations of abaloparatide administered by transdermal versus subcutaneous routes in healthy postmenopausal women.

Figure 21:
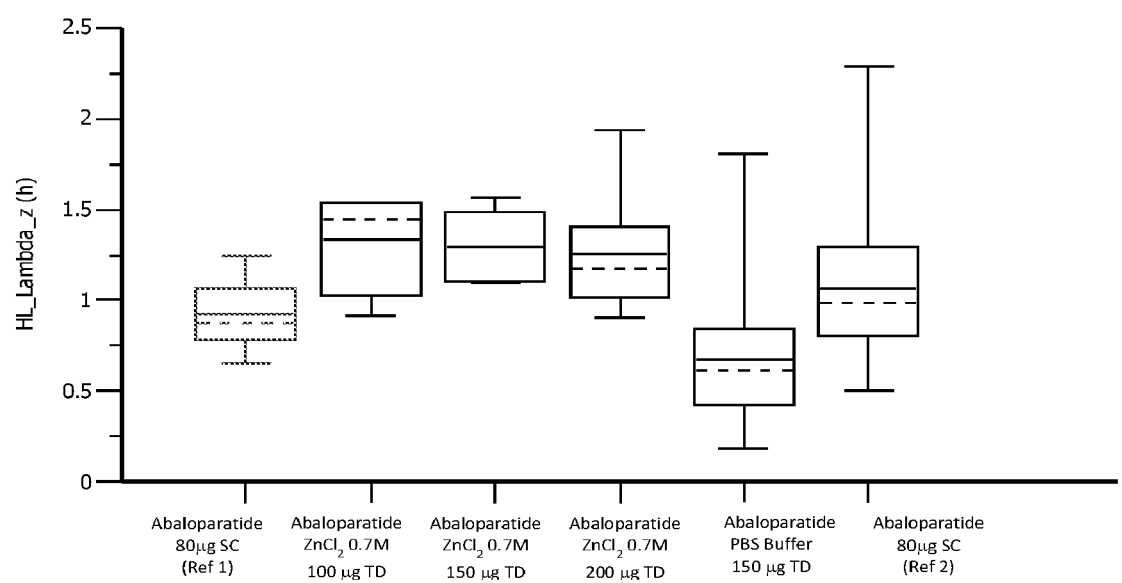

FIG. 21: Comparison of HL_Lambda_z of formulations of abaloparatide administered by transdermal versus subcutaneous routes in healthy postmenopausal women.

Figure 22:
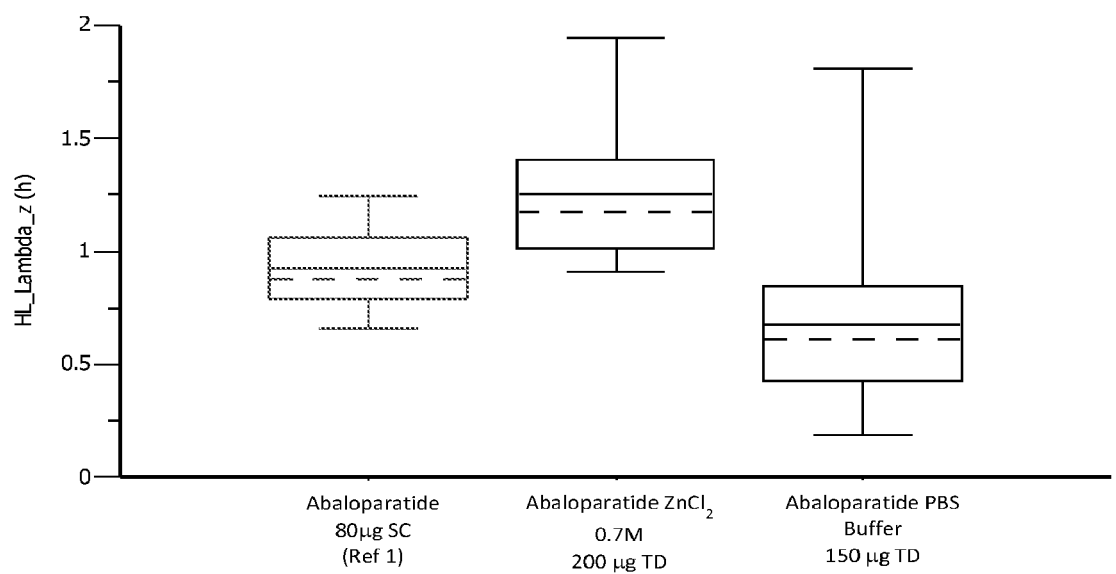

FIG. 22: Comparison of HL_Lambda_z of formulations of abaloparatide administered by transdermal versus subcutaneous routes in healthy postmenopausal women.

Figure 23:
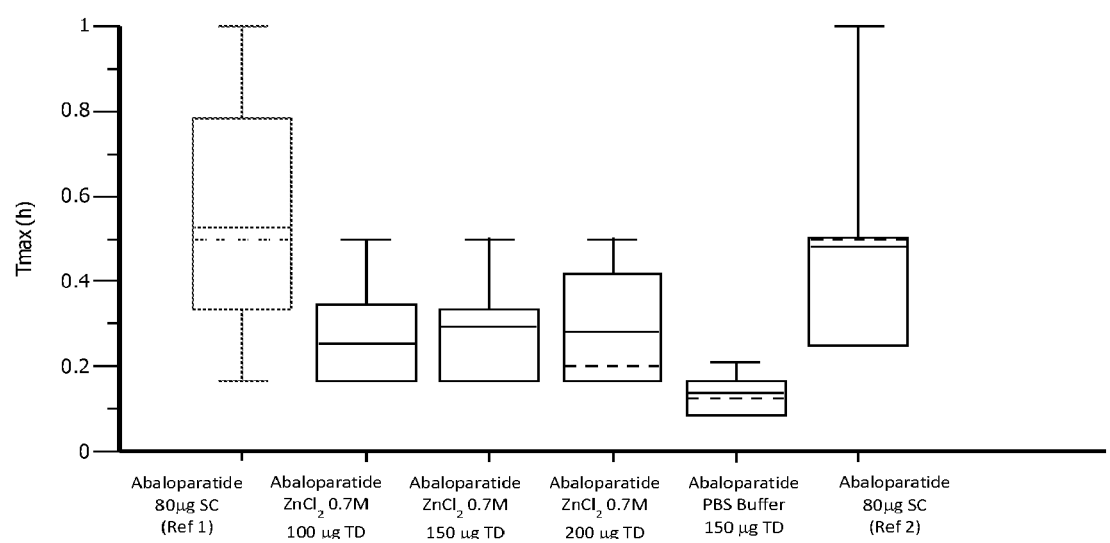

FIG. 23: Comparison of $T_{max}$ of formulations of abaloparatide administered by transdermal versus subcutaneous routes in healthy postmenopausal women.

Figure 24:
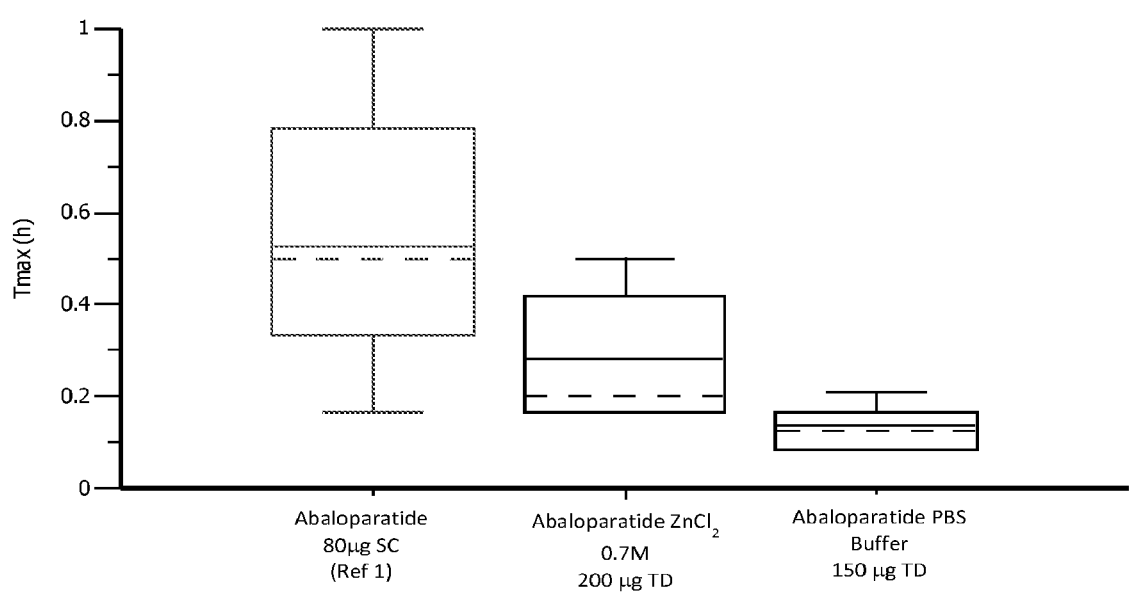

FIG. 24: Comparison of $T_{max}$ of formulations of abaloparatide administered by transdermal (abdomen) versus subcutaneous routes in healthy postmenopausal women.

Figure 25:
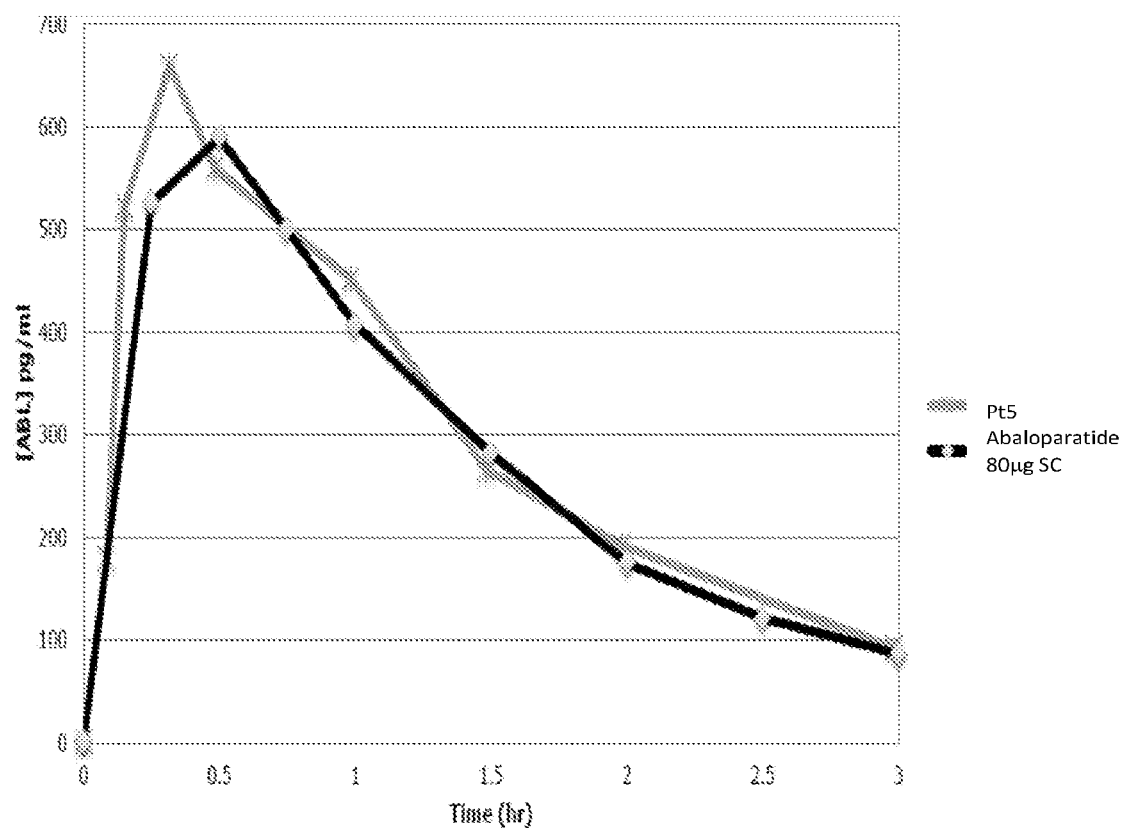

FIG. 25: Pharmacokinetic profile of formulations of abaloparatide formulation including $ZnCl_2$ (from 0.7M coating solution) administered by transdermal route in a selected patient versus subcutaneous dose in healthy postmenopausal women.

Figure 26:
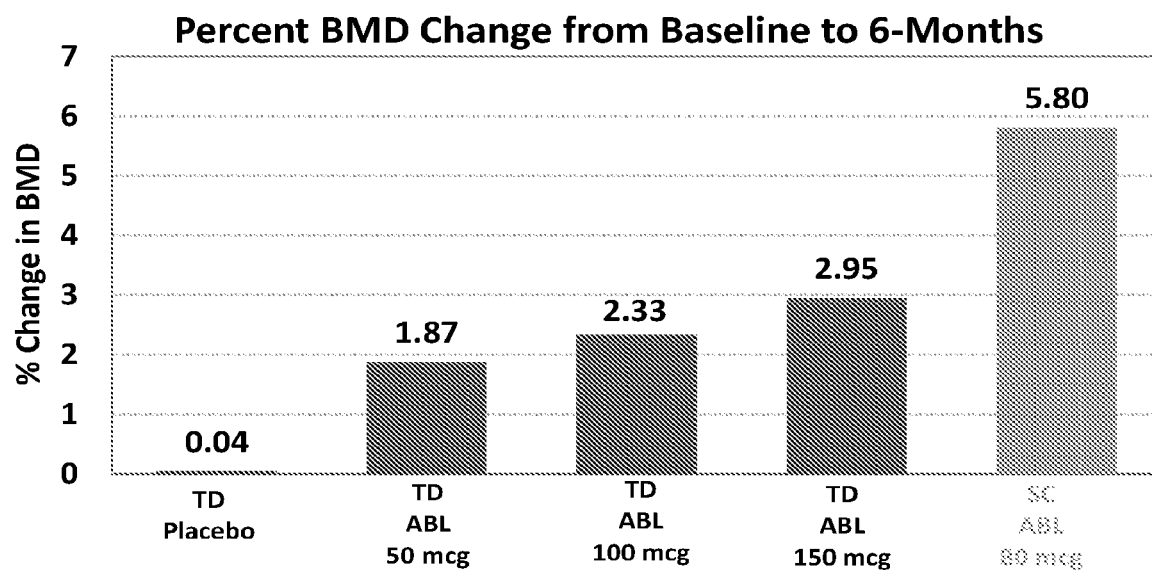

FIG. 26: Percent BMD changes from baseline at lumber spine of the subjects treated with abaloparatide via transdermal delivery or SC injection in postmenopausal women with osteoporosis. Transdermal delivery used abaloparatide formulations with PBS buffer (no additional added excipient).

Figure 27:
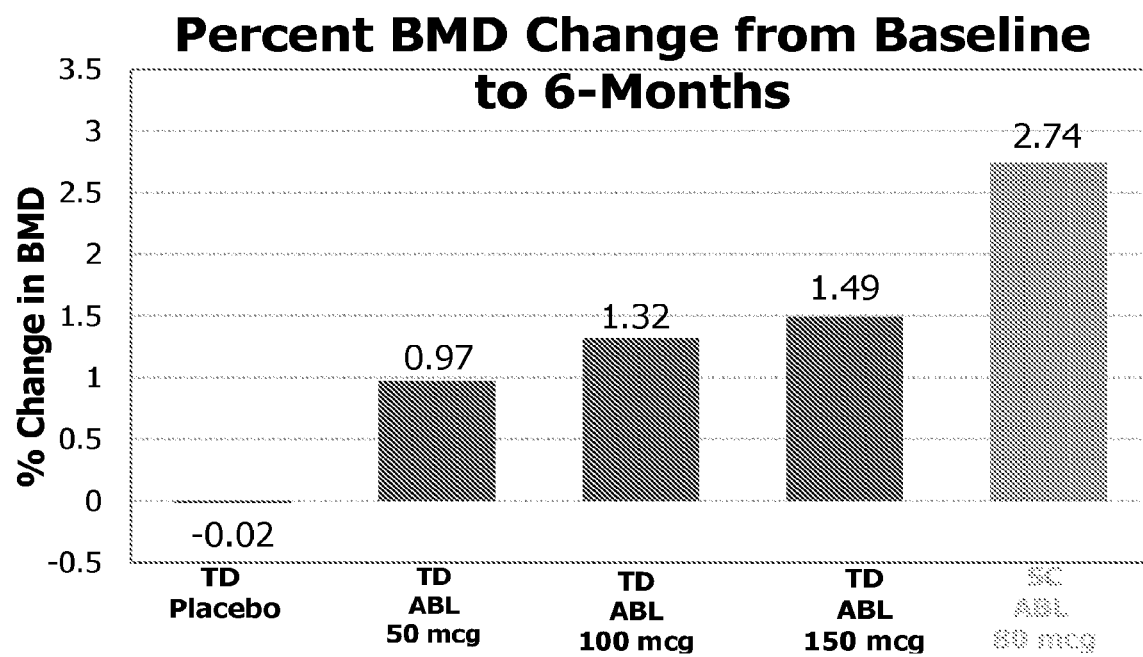

FIG. 27: Percent BMD changes from baseline at total hip of the subjects treated with abaloparatide via transdermal delivery or SC injection in postmenopausal women with osteoporosis. Transdermal delivery used abaloparatide formulations with PBS buffer (no additional excipient).

Figure 28:
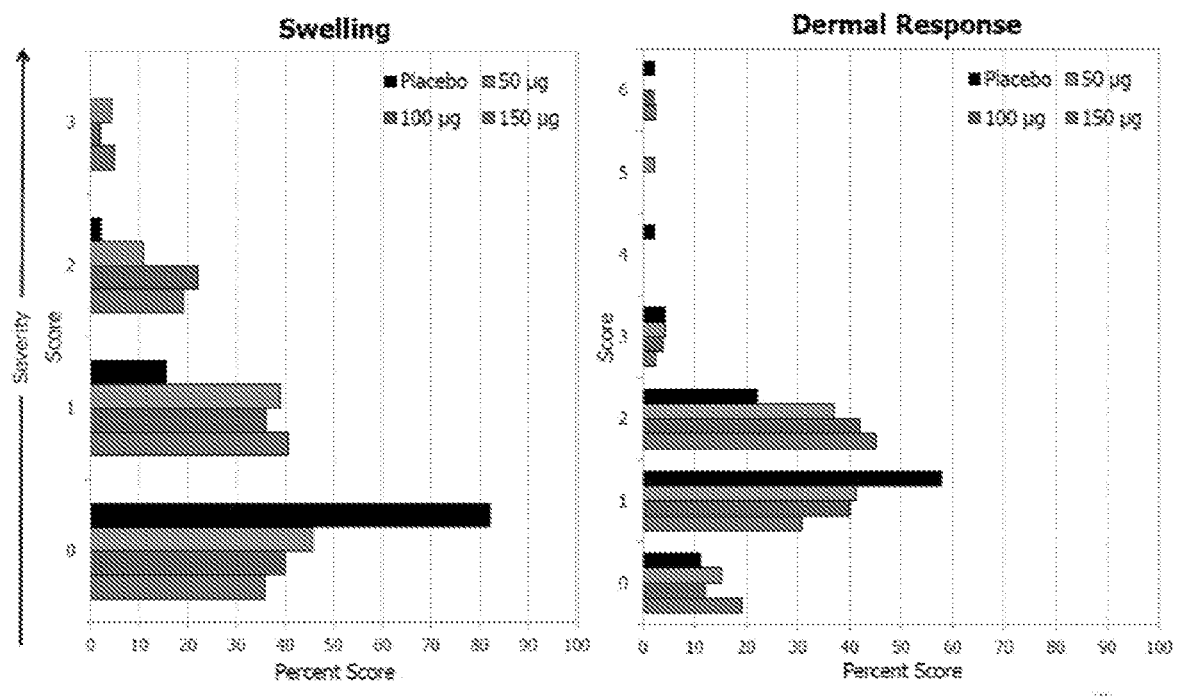

FIG. 28: Local tolerance data of the subjects treated with abaloparatide via transdermal delivery in postmenopausal women with osteoporosis. Transdermal delivery used abaloparatide formulations with PBS buffer (no additional excipient).

Figure 29:
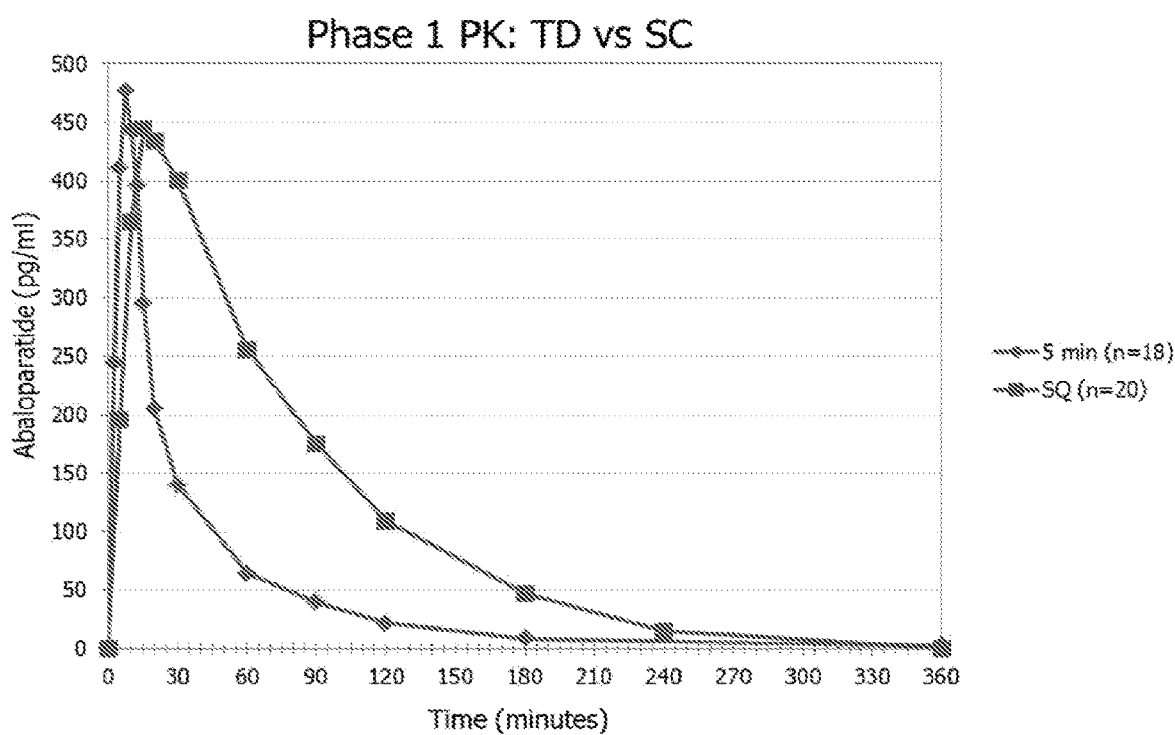

FIG. 29: Pharmacokinetic profile of formulations of abaloparatide administered by transdermal delivery using abaloparatide formulations with PBS buffer only in healthy postmenopausal women (diamond) versus subcutaneous (square) routes. Note the very rapid and pulsatile release in the transdermal delivery compared to the SC administration.

Figure 30A:
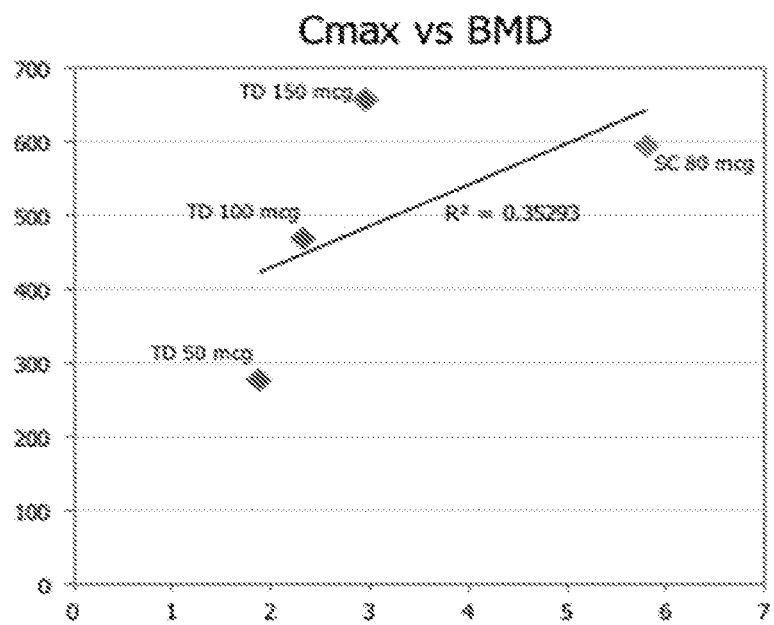
Figure 30B:
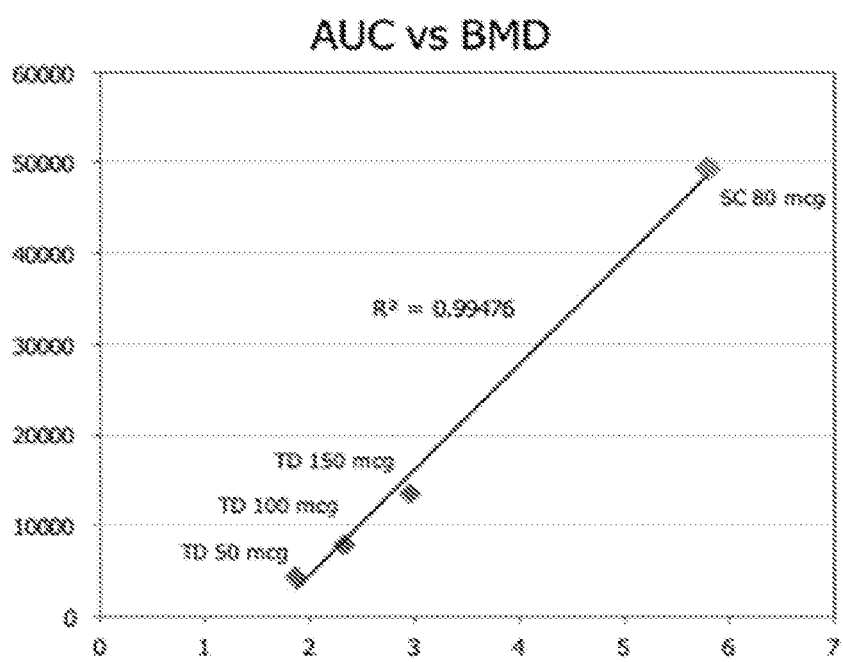

FIGS. 30A-30B: PK/PD relationship of formulations of abaloparatide administered by transdermal and by subcutaneous routes in postmenopausal women with osteoporosis. FIG. 30A: $C_{max}$ v. BMD improvement (%) for formulations of abaloparatide administered by transdermal and by subcutaneous routes. FIG. 30B: AUC v. BMD improvement (%) for formulations of abaloparatide administered by transdermal and by subcutaneous routes.

Figure 31:
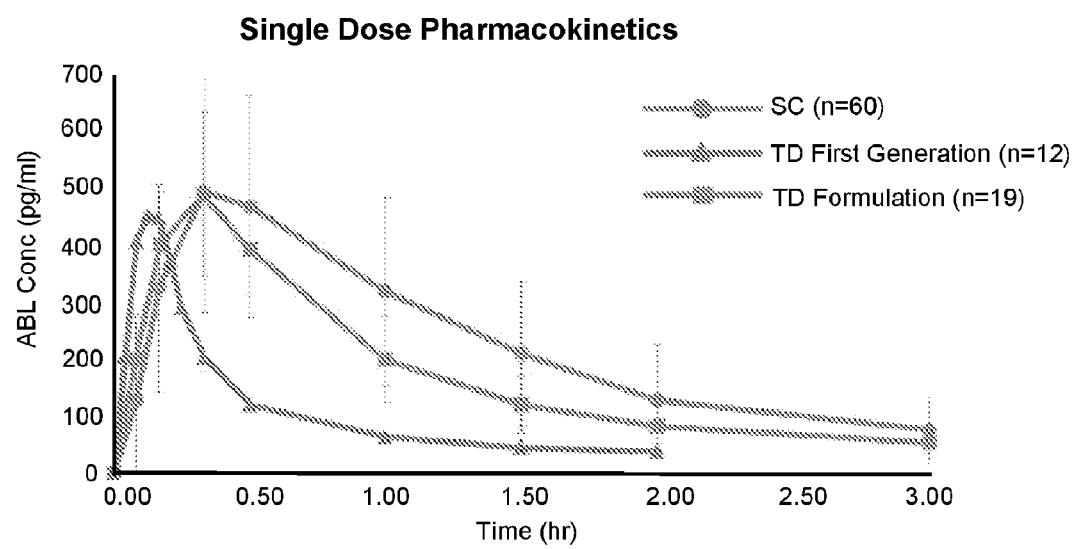

FIG. 31: Comparison of pK curves from a sc combination cohort (80 µg), (200 µg abaloparatide+PBS buffer only (labeled "1$^{st}$ generation") and (200 µg abaloparatide+$ZnCl_2$). Values are the geometric means.

Figure 32:
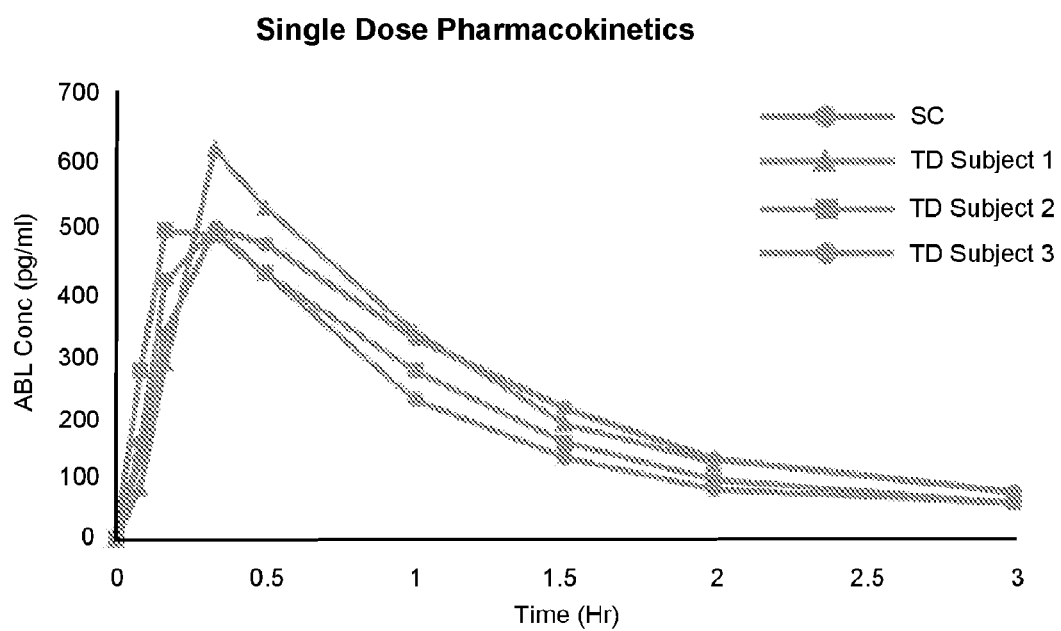

FIG. 32: Comparison of pK curves of selected individual patients being treated with (200 µg abaloparatide plus $ZnCl_2$) and compared to sc treated patients. Values are the geometric means.

Figure 33:
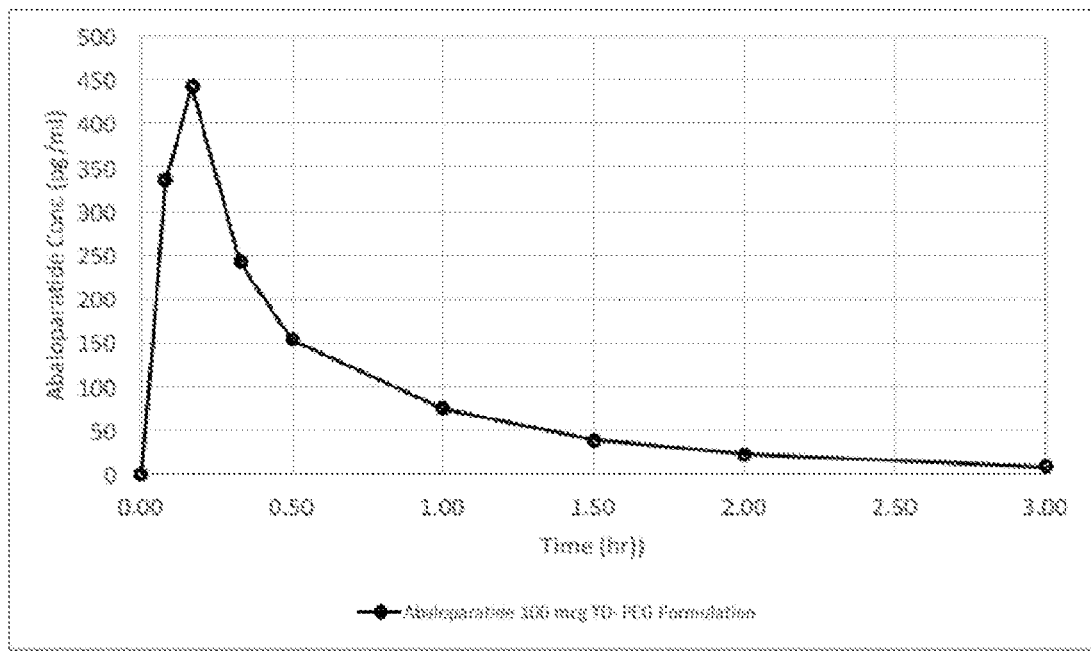

FIG. 33: Concentration-time graph after administration of patch formulated with PEG 3350 NF and 100 µg of abaloparatide to abdomen of healthy post-menopausal women (N=12) where plasma concentration time points are the arithmetic means.

Figure 34:
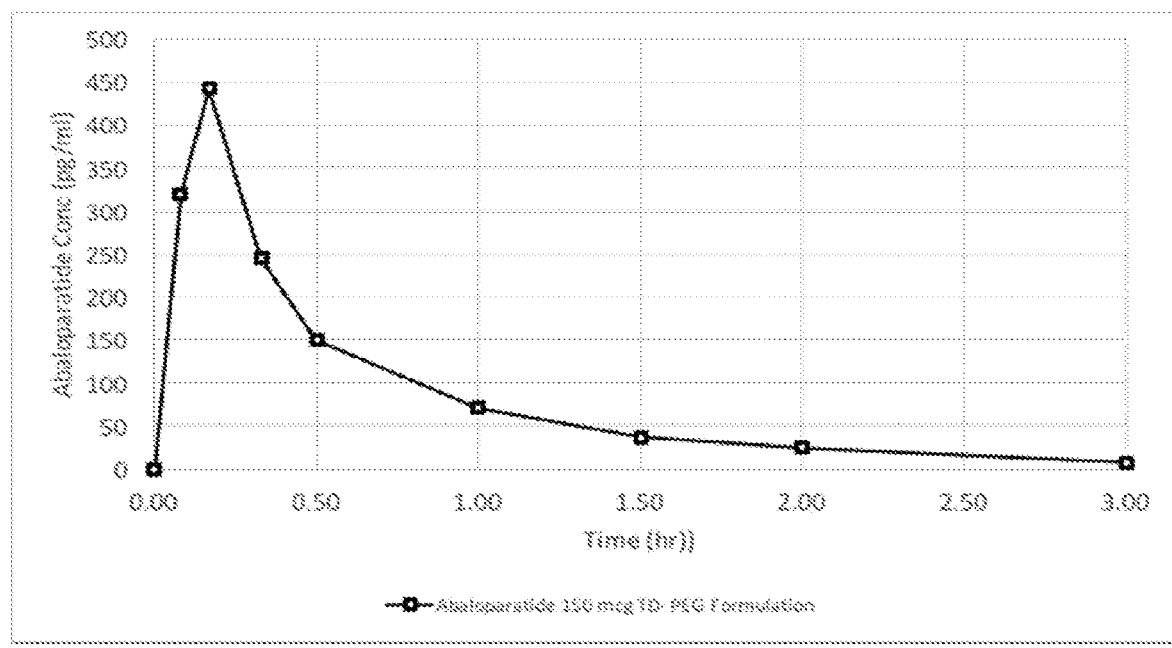

FIG. 34: Concentration-time graph after administration of patch formulated with PEG 3350 NF and 150 µg of abaloparatide to abdomen of healthy post-menopausal women (N=13) where plasma concentration time points are the arithmetic means.

Figure 35:
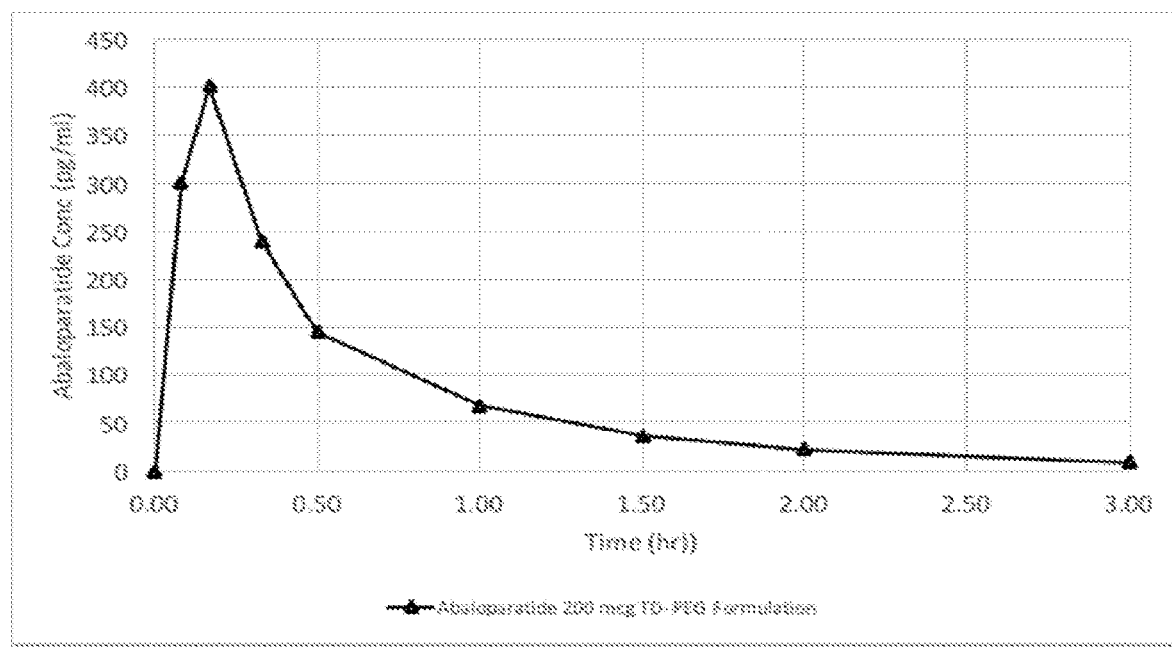

FIG. 35: Concentration-time graph after administration of patch formulated with PEG 3350 NF and 200 μg of abaloparatide to abdomen of healthy post-menopausal women (N=14) where plasma concentration time points are the arithmetic means.

Figure 36:
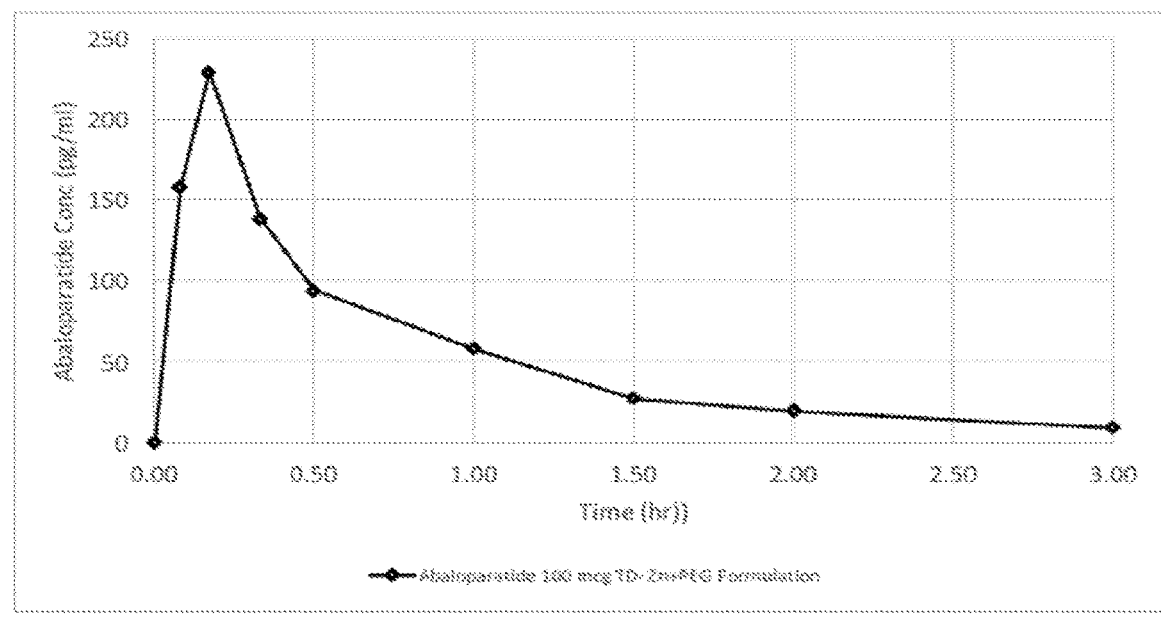

FIG. 36: Concentration-time graph after administration of patch formulated with PEG 3350 NF and $ZnCl_2$ and 100 μg of abaloparatide to abdomen of healthy post-menopausal women (N=8) where plasma concentration time points are the arithmetic means.

Figure 37:
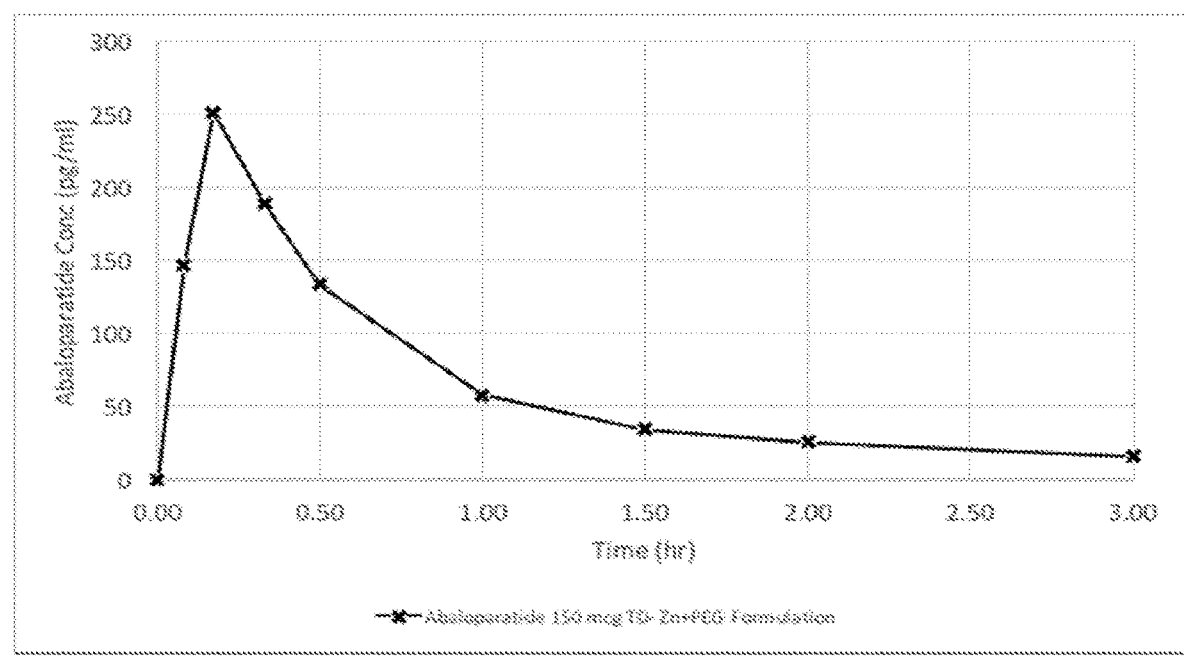

FIG. 37: Concentration-time graph after administration of patch formulated with PEG 3350 NF and $ZnCl_2$ and 150 μg of abaloparatide to abdomen of healthy post-menopausal women (N=7) where plasma concentration time points are the arithmetic means.

Figure 38:
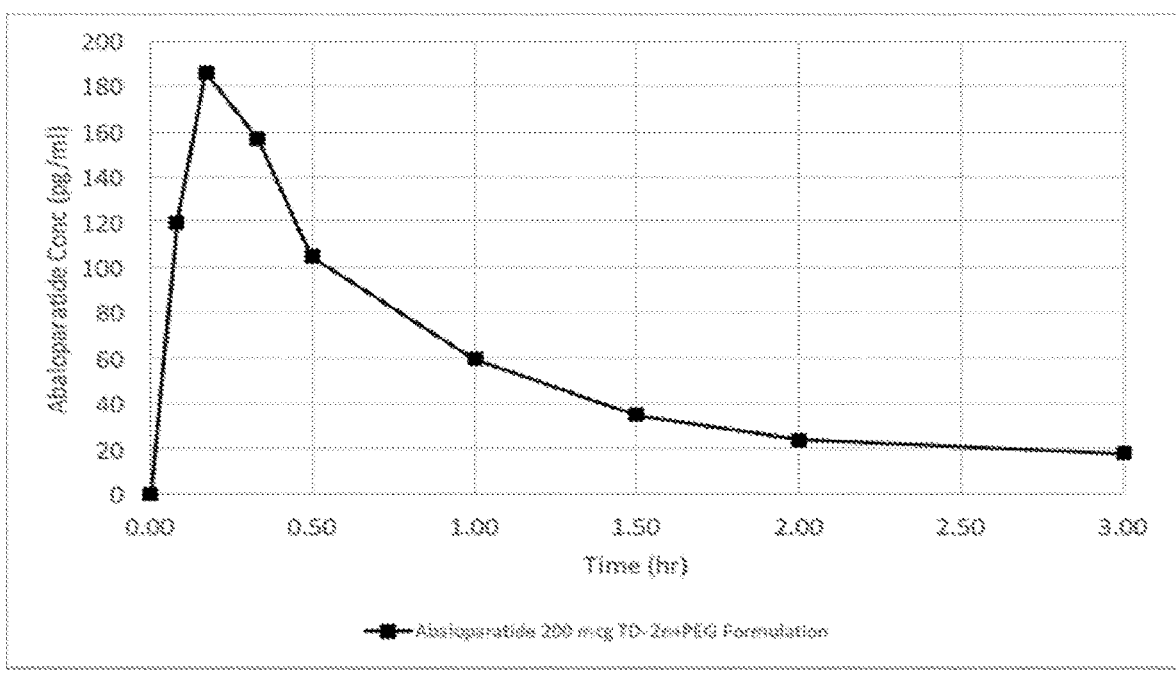

FIG. 38: Concentration-time graph after administration of patch formulated with PEG 3350 NF and $ZnCl_2$ and 200 μg of abaloparatide to abdomen of healthy post-menopausal women (N=8) where plasma concentration time points are the arithmetic means.

Figure 39:
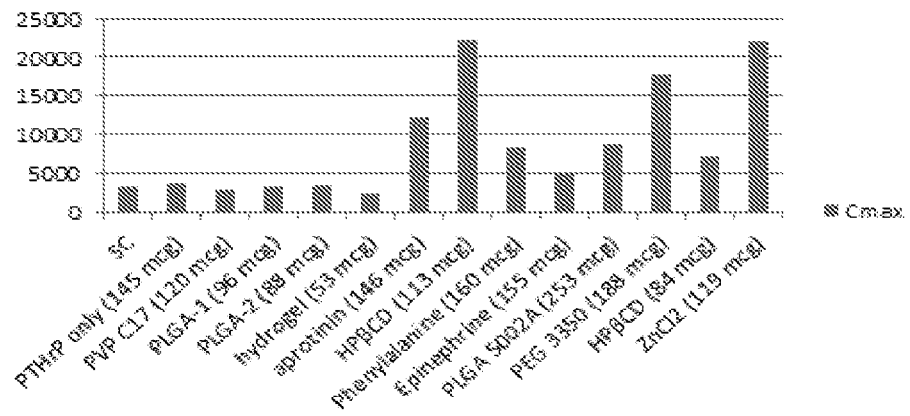

FIG. 39: Comparison of $c_{max}$ (peak plasma concentration (pg/mL)) of various formulations of abaloparatide in monkeys.

Figure 40:
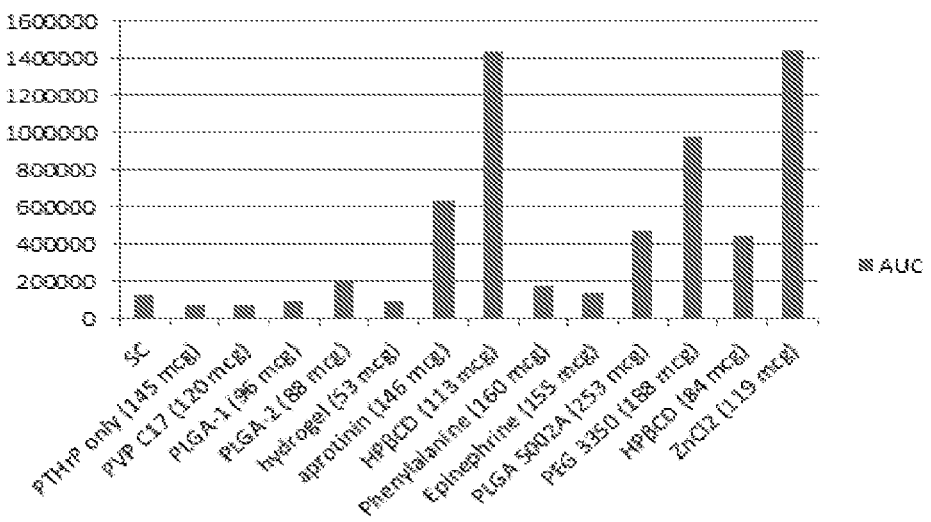

FIG. 40: Comparison of AUC (area under the curve) of various formulations of abaloparatide administered by transdermal versus subcutaneous route in monkeys.

Figure 41:
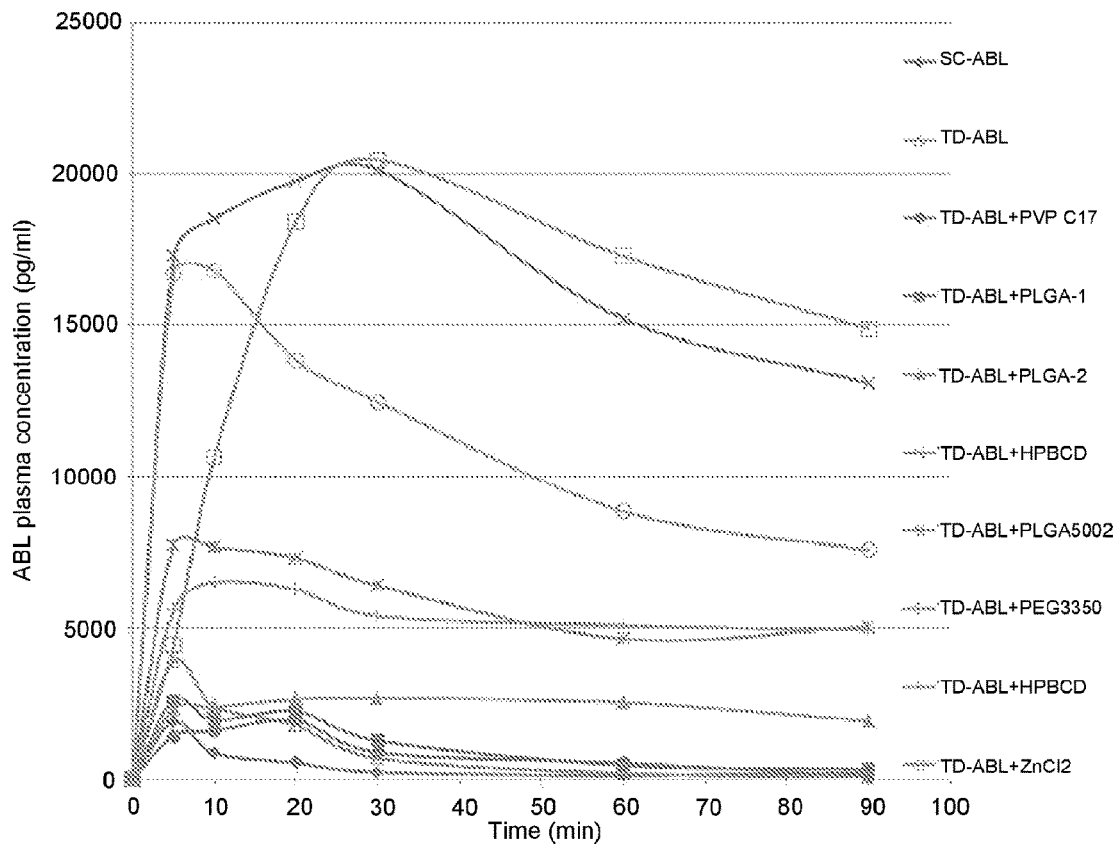

FIG. 41: Comparison of plasma concentration (pg/mL) of formulation of abaloparatide administered by subcutaneous route (SC) or transdermal administration (TD), wherein the transdermal administration utilized a transdermal patch coated using different transdermal formulations in monkeys.

Figure 42:
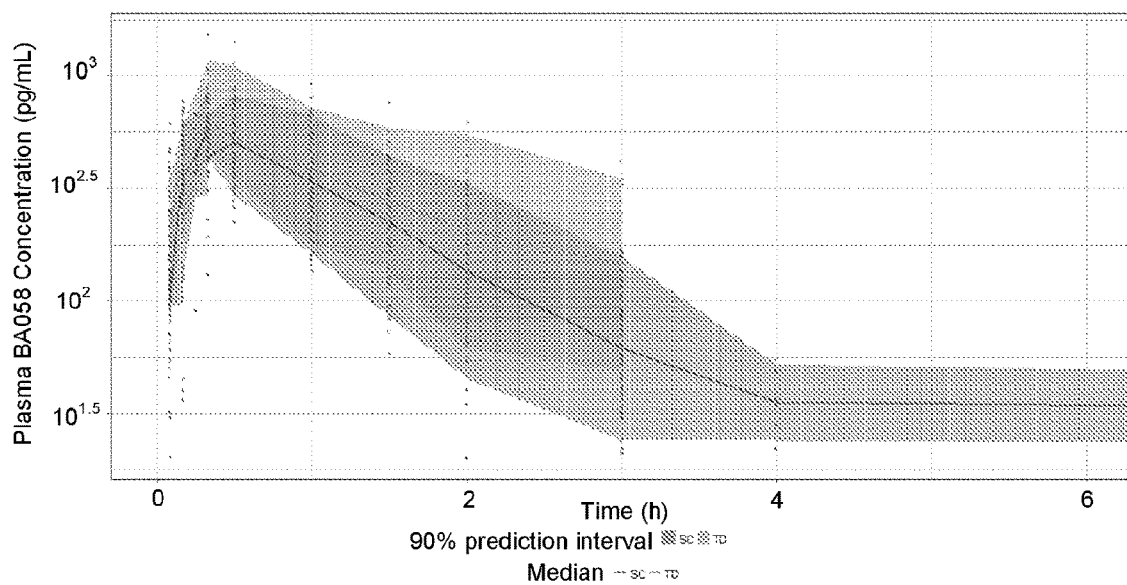

FIG. 42: pK profile of abaloparatide administration in a transdermal formulation containing $ZnCl_2$ overlayed with a reference abaloparatide 80 μg sc dose. Shaded areas around the geometric mean lines represent the 90% confidence intervals.

Figure 43:
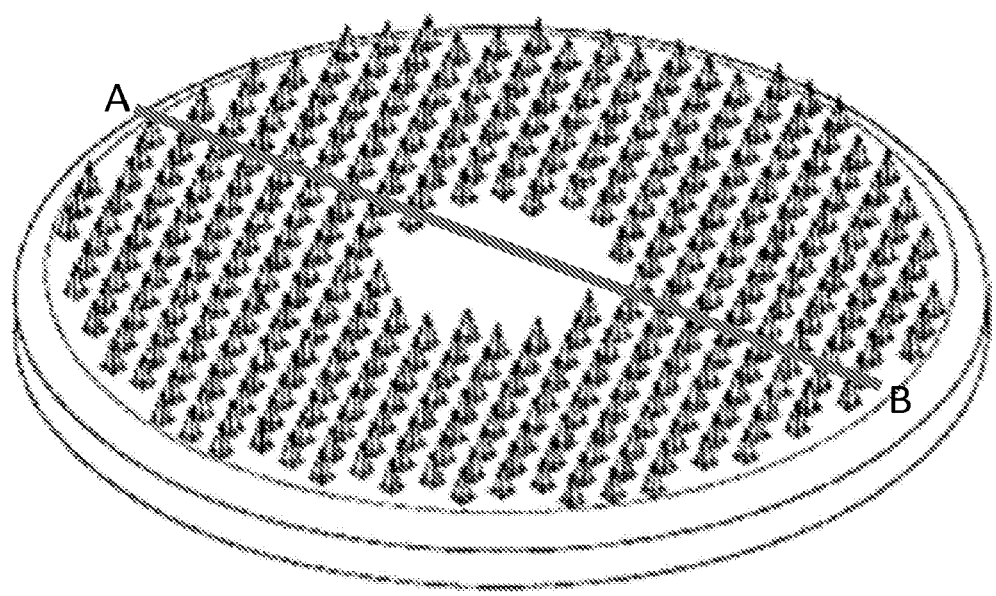

FIG. 43: Circular patch illustration with diameter shown by A-B.

Table 1. Modeling of TD-A32 data for bioequivalence for the abaloparatide-SC treatment.

Table 2. pK Results of TD Abaloparatide ($ZnCl_2$, (0.7 mole ratio to abaloparatide) in coating solution) at 100 μg 150 μg TD, 200 μg; Abaloparatide 80 μg SC (Ref1); and abaloparatide 150 μg TD (PBS buffer only).

Table 3. pK Results of TD Abaloparatide ($ZnCl_2$, (0.7 mole ratio to abaloparatide) coating solution) at 100 μg 150 μg TD, 200 μg; Abaloparatide 80 μg SC Ref1; abaloparatide 150 μg TD (PBS buffer only); to SC (Ref2).

Table 4. pK results of Abaloparatide ($ZnCl_2$ (0.7 mole ratio to abaloparatide) coating solution) at 100 μg TD, Abaloparatide 150 μg TD, Abaloparatide 200 μg TD; Abaloparatide 80 μg SC (Ref1); to 150 μg TD (PBS only)—Site of administration is abdomen Table 5. Design for a Phase 2 study of transdermal delivery of abaloparatide using a transdermal patch (PBS only).

Table 6. $C_{max}$, AUC, and BMD improvement of a Phase 2 study of transdermal delivery of abaloparatide (TD-50 mcg, TD-100 mcg, and TD-150 mcg with PBS buffer only) using a transdermal patch, and subcutaneous delivery of abaloparatide (SC-80 mcg).

Table 7. Pharmacokinetic parameters of TD formulation examples 8-13 compared to a reference group of 80 μg sc treated women. Geometric LS-means and ratios of TD and sc.

Table 8. Individual's pharmacokinetic parameters from one study cohort.

Table 9. Individual's pharmacokinetic parameters from one study cohort.

DETAILED DESCRIPTION

Abaloparatide is a synthetic PTHrP analogue having the sequence set forth in SEQ ID NO:1. Abaloparatide has shown potent anabolic activity with decreased bone resorption, less calcium-mobilizing potential, and improved room temperature stability (Obaidi 2010). Studies performed in animals have demonstrated marked bone anabolic activity following administration of abaloparatide, with complete reversal of bone loss in ovariectomy-induced osteopenic rats and monkeys (Doyle 2013a; Doyle 2013b; Hattersley 2013). Abaloparatide has been developed as a promising anabolic agent for the treatment of osteopenia (e.g., glucocorticoid-induced osteopenia), osteoporosis (e.g. glucocorticoid-induced osteoporosis), and/or osteoarthritis.

Subcutaneous administration of 80 μg abaloparatide (hereinafter the "abaloparatide-SC treatment") has been shown to significantly reduce incidences of new vertebral, non-vertebral, major osteoporotic and clinical fractures versus a placebo. Subcutaneous abaloparatide administration has also been shown to improve bone mineral density (BMD) and/or trabecular bone score (TBS) of treated subjects at the lumbar spine, total hip, and femoral neck. In certain embodiments, the abaloparatide-SC treatment comprises subcutaneous administration of an aqueous formulation comprising abaloparatide (about 2 mg/mL) in an acetate buffer, with a pH of about 4.5 to about 5.6, or about 5.1. Optionally, the aqueous formulation further comprises phenol (about 5 mg/mL). In certain examples of these embodiments, the acetate buffer comprises tri-hydrate sodium acetate (about 5 mg/mL) with pH (e.g., about 4.5 to about 5.6, or about 5.1) adjusted with acetic acid. Unless specifically stated otherwise, comparative abaloparatide sc dose use an 80 μg dose delivered subcutaneously to the periumbilicular region of the abdomen of the patient.

Transdermal administration of abaloparatide is an attractive alternative to subcutaneous administration due to its less invasive nature. In particular, it might be advantageous in some contexts to develop transdermal abaloparatide administrations that are substantially bioequivalent or bioequivalent to the subcutaneous abaloparatide administration in order to benefit from its proven sc efficacy.

As disclosed herein, it has been unexpectedly found that transdermal abaloparatide administration using a patch prepared with a preparation formulation comprising abaloparatide and one or more of the described excipients can modify the pharmacokinetic profile of abaloparatide administered by sc.

Based on these findings, provided herein are abaloparatide formulations, transdermal patches prepared using these preparation formulations, transdermal patches comprising these preparation formulations, methods of making these patches, and methods of using the disclosed preparation formulations and patches to administer abaloparatide in a transdermal manner and to treat osteoporosis, osteopenia, and osteoarthritis, improve BMD, improve TBS, and treat, prevent, and reduce bone fractures in a subject. In certain embodiments of the preparation formulations, transdermal patches, and methods provided herein, the transdermal delivery of abaloparatide produces substantial bioequivalence or bioequivalence to a subcutaneous delivery of abaloparatide at the dosage of about 20 µg to about 200 µg, about 40 µg to about 120 µg, about 60 µg to about 100 µg, about 70 µg to about 90 µg, or about 80 µg. In certain embodiments of the preparation formulations, transdermal patches, and methods provided herein, the transdermal delivery of abaloparatide is a substantial bioequivalence or bioequivalence of the abaloparatide-SC treatment.

Figure 1A:
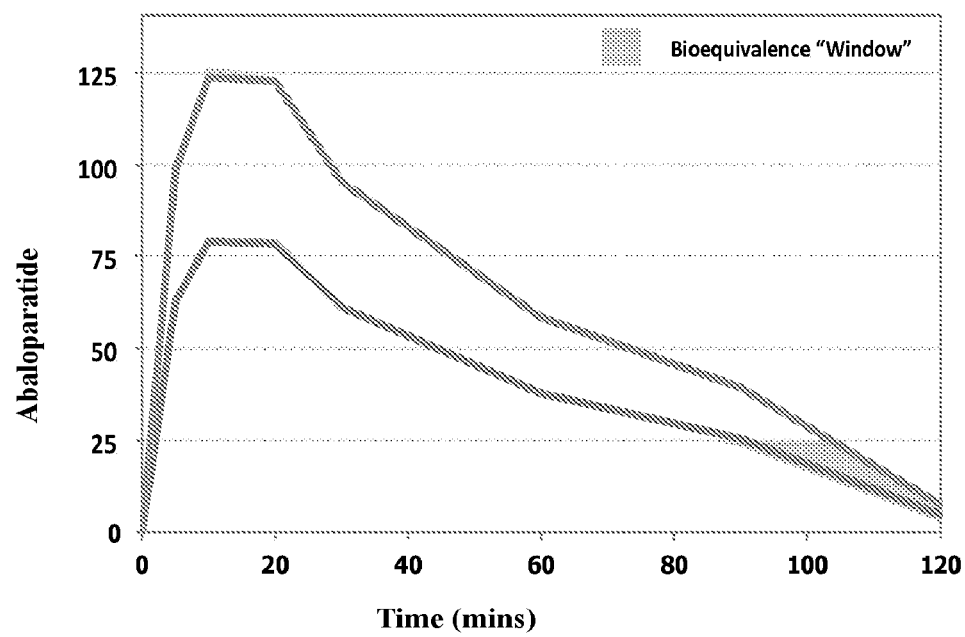
FIGS. 1A-1C: Pharmacokinetic profile of various formulations of abaloparatide administered by transdermal versus subcutaneous routes.

As used herein, two treatments of an active agent are bioequivalent to one another if the 90% confidence interval of the ratio of area under the curve (AUC) and/or the peak serum concentration of the active agent ($C_{max}$) falls completely within the range 80-125%. See, e.g., FIG. 1A showing a bioequivalence window of the abaloparatide-SC treatment in Chinese Cynomolgus monkeys. Serum abaloparatide concentrations are presented as percentage of $C_{max}$.

As used herein, the term "substantially," "substantial" or "essentially" bioequivalent means nearly completely or completely bioequivalent to a sc abaloapratide formulation, eg an 80 µg abaloparatide sc formulation. In one embodiment, a formulation is substantially or essentially bioequivalent if it falls within a bioequivalent range. In one embodiment, a bioequivalent range means the 90% confidence interval of the mean or geometric mean ratio of a compound in a particular formulation for transdermal delivery to a reference formulation falls within 80%-125% for AUC $_{(0-t,}$ and/or $_{0-inf)}$ and/or $C_{max}$. In some embodiments the reference formulation is the SC formulation of 80 µg abaloparatide as described herein. In certain embodiments, the transdermal delivery of a compound or more particularly abaloparatide falls within a substantially bioequivalent range wherein said range is 50%-200%, or 60%-147%, or 60%-167%, or 65%-141%, 65%-154%, 70%-136%, 70%-143%, or 75%-133%, for the mean or geometric mean of the 90% confidence interval (CI)) of AUC $_{(0-t}$ and/or $_{0-inf)}$ and/or $C_{max}$ of the test formulation (and delivery method, eg TD) to the reference formulation and delivery method (eg SC). In certain embodiments, confidence intervals can be narrower or broader, for example, confidence intervals between 70-95% or 75%, 80%, 85%, 90% or 95% may be applicable. In some embodiments, $t_{1/2}$ and/or $t_{max}$ are components of a bioequivalence calculation and in some embodiments, the confidence intervals and ranges described herein apply as well.

In some embodiments, the bioavailability of a test article to a reference is defined by the upper and lower bound including the upper and lower confidence intervals and can be represented as shown in the formula below, where T is test, R is reference. Multiplying the ratios obtained by 100% gives the upper and lower confidence bounds where $t_{df}^{1-\alpha}$ value is set according to the desired confidence interval (eg 90%). In some embodiments, the bioequivalence is established according to a standard two-way crossover design.

$$\left[ \tilde{x}_T - \tilde{x}_R - t_{df}^{1-\alpha} \sqrt{\frac{\hat{\sigma}_T^2}{n_T} + \frac{\hat{\sigma}_R^2}{n_R}}, \tilde{x}_T - \tilde{x}_R + t_{df}^{1-\alpha} \sqrt{\frac{\hat{\sigma}_T^2}{n_T} + \frac{\hat{\sigma}_R^2}{n_R}} \right]$$

Sometimes overall bioequivalence is established by setting different parameters around the 90% confidence interval needs to fall within. For example, bioequivalence may require falling within an 80-125% range on AUC parameters while allowing Cmax to fall within 70-143% and still be acceptable. Similarly, confidence intervals can be varied depending on the circumstance. Normally 90% confidence windows are used but in some instances lower or even higher confidence intervals might be required (eg 85% or 95%). More broadly, the particular bioequivalence definition for a particular product can be adjusted according to the particular requirements of the situation.

It is an aspect of this invention that the $t_{max}$ is affected by the excipient embodiments of this invention. One feature of many embodiments of this invention is the ability to modulate the $t_{max}$ of a transdermal delivery. In certain embodiments, the $t_{max}$ is increased compared to the administration of a non-excipient containing patch (eg buffer only, like PBS buffer). In some embodiments, the transdermal administration of abaloparatide to humans with a formulation embodiment of this invention results in a $t_{max}$ that is greater than the $t_{max}$ under the same conditions except without one of the formulation embodiments of this invention. In some instances, a mean $t_{max}$ of >0.135 h, or >0.15 h, or >0.2 h, >0.3 h, >0.35 h, or between 0.135 h-0.45 h, or between 0.135 h-0.4 h, or between 0.15 h-0.4 h, between 0.2 h and 0.5 h, or between 0.2 h and 0.6 h is achieved following the administration of a transdermal patch embodiment of this invention. In certain embodiments, the $t_{max}$ can be defined as a median $t_{max}$. Expressed as a median $t_{max}$, the embodiments of this invention can reach >0.1 h, or >0.16 h, >0.2 h or >0.3 h or about 0.17 h, or about 0.33 h, or between 0.1 h and 0.4 h.

In some aspects, the embodiments of this invention provide a way to increase the apparent $t_{1/2}$ of an administered drug, eg abaloparatide. The apparent $t_{1/2}$ can be increased for the administration of a transdermal patch containing a formulation or excipient embodiment of this invention. Administration of a transdermal embodiment of this invention can result in an apparent mean $t_{1/2}$ in a subject of >0.70 h or >0.8 h or >1 h or >1.09 h or >1.25 h or >1.5 h or between 0.8 h and 2.0 h, or between 1.0 h and 2.0 h. The median $t_{1/2}$ can be >0.6 h, or >0.75 h, or >1 h, or 1.4 h or >1.5 h.

The geometric mean $AUC_{0-last}$ (or 0-t) of abalopartide after transdermal administration under embodiments of this invention can fall with certain ranges. For example, a geo mean $AUC_{0-t}$ can be therapeutically effective between 386-916 h*pg/mL, or >375 h*pg/mL, or >450 h*pg/mL, or >525 h*pg/mL, or >550 h*pg/mL, or >600 h*pg/mL, or >700 h*pg/mL or between 600-1000 h*pg/mL, or 700-1100 h*pg/mL, or 700-1000 h*pg/mL.

The geometric mean $AUC_{0-inf}$ of abaloparatide after transdermal administration under embodiments of this invention can fall with certain ranges. For example, a geo mean $AUC_{0-t}$ can be therapeutically effective between 444-1292 h*pg/mL, or >400 h*pg/mL, or >450 h*pg/mL, or >550 h*pg/mL, or >700 h*pg/mL or between 600-1000 h*pg/mL, or 700-1100 h*pg/mL, or 700-1000 h*pg/mL.

The $C_{max}$ of abaloparatide after transdermal administration can fall with certain ranges. For example, a geo mean $C_{max}$ can be therapeutically effective between 358 pg/ml and 707 pg/ml, or >350 pg/ml, or >500 pg/ml, or >600 pg/ml, or >700 pg/ml, or between 300-850 pg/mL, or between 400-900 pg/ml.

In general and unless stated otherwise, bioequivalence or substantial bioequivalence does not require that there be a dose parity to the sc dosage being compared to but rather, that the $C_{max}$ and/or AUC are substantially bioequivalent or bioequivalent according to the definitions of each as provided herein. For example, a transdermal dose can be higher than the sc dose and still meet the bioequivalent definitions as explained herein.

As used herein, the term "about" or "approximately" means a range of ±0-10%, or ±0-5% or the numeral following the term.

As used herein, "SC Ref 1" refers to an 80 μg delivery of abaloparatide subcutaneously using a reusable pen delivery device. "SC Ref 2" refers to a disposable pen delivery device. Unless stated otherwise, both use the same formulation and injection site and either or both can be used for establishing comparative features of the invention to the reference(s). In cases where an 80 μg sc dose is referred to but not by reference it is one or the other.

As used herein, the term "transdermal delivery" refers to a delivery of an active agent through the stratum corneum to make contact with the intradermal space without significant pain upon penetration. Because the stratum corneum has no nerves, it may be pierced without stimulating nerves. The terms "transdermal" and "intradermal" are used interchangeably herein. The stratum corneum is composed primarily of several layers of dead skin cells and is not vascularized. Thus, the stratum corneum often poses a formidable barrier to the transdermal delivery of an active agent, especially for charged macromolecules such as peptides. Unlike active agents delivered by subcutaneous injection, which almost provides a complete entrance into the blood stream, many factors (and barriers) can affect the pharmacokinetics of drugs delivered by a transdermal route. For example, the site of application, the thickness, integrity, and hydration condition of the skin, the thickness and density of the adipose tissue under the skin of the application site, the size of the drug molecules, the pH condition and permeability of the membrane of the transdermal device, etc., all may affect the bioavailability of drugs delivered transdermally. In certain embodiments, transdermal delivery involves penetrating the skin through the stratum corneum into the dermis to a depth of up to about 700 μm, or up to about 600 μm, or up to about 500 μm, or up to about 400 μm, or up to about 300 μm, or up to about 250 μm, or up to about 150 μm. In some embodiments, the average needle depth of penetration is approximately 800 μm, or about 700 μm, or about 600 μm, or about 500 μm, or about 400 μm, or about 300 μm, or about 250 μm, or about 150 μm.

I. Preparation Formulation for Transdermal Delivery

Provided herein in certain embodiments are preparation formulations for transdermal delivery of abaloparatide. In certain embodiments, the transdermal delivery produces a substantial bioequivalence or bioequivalence to subcutaneous delivery of (e.g., at 80 μg), for example, abaloparatide. These formulations comprise abaloparatide and one or more excipients selected from the group consisting of salts of $Zn^{2+}$, salts of $Mg^{2+}$, salts of $Ca^{2+}$, salts of histidine, salts of carboxylic acids (e.g., fatty acids), NaCl, PEG, PVP, cyclodextrin (CD, e.g., 2-hydroxypropyl-β-cyclodextrin (HPβCD)), and combinations thereof. In certain embodiments the salt of $Zn^{2+}$ is selected from the group consisting of $Zn(OAc)_2$, $ZnCl_2$, $Zn_3(PO_4)_2$, zinc citrate (ZnCitrate), zinc oxalate (ZnOxalate), and combinations thereof, the salt of $Ca^{2+}$ is selected from the group consisting of calcium sorbate (CaSorbate), calcium citrate (CaCitrate), calcium ascorbate (CaAscorbate), $Ca_3(PO_4)_2$, $CaCl_2$, $CaCO_3$, $CaSO_4$, $Ca(OAc)_2$ and combinations thereof, the salt of $Mg^{2+}$ is selected from the group consisting of MgO, magnesium citrate (MgCitrate), $MgSO_4$, magnesium orotate (MgOrotate), magnesium lactate (MgLactate), $MgCO_3$, $MgCl_2$, $Mg(OAc)_2$, and combinations thereof. In certain embodiments, two or more salts of $Mg^{2+}$, $Zn^{2+}$ and/or $Ca^{2+}$ as described herein are combined together for purposes of a transdermal formulation. In certain embodiments, the preparation formulation further comprises water for injection, brine or PBS. In certain embodiments, the transdermal delivery of abaloparatide produces substantial bioequivalence or bioequivalence to a subcutaneous delivery of abaloparatide at the dosage of about 20 μg to about 200 μg, about 40 μg to about 120 μg, about 60 μg to about 100 μg, about 70 μg to about 90 μg, or about 80 μg. In certain embodiments, the transdermal delivery of abaloparatide is substantially bioequivalent or bioequivalent to the abaloparatide-SC treatment. In certain embodiments, abaloparatide is delivered by a transdermal patch comprising at least one microprojection (e.g., microneedle) prepared using the preparation formulation.

In certain embodiments, the preparation formulation comprises PEG with a molecular weight of about 3,000 to about 3,700, about 2,000 to about 5,000, about 3.00 to about 3,500, or about 1,000 to about 6,000. A concentration by weight of PEG to the total amount of the preparation formulation is about 0.01% to about 50%, about 5% to about 50%, about 5% to about 45%, about 5% to about 40%, about 5% to about 35%, about 5% to about 30%, about 5% to about 25%, about 5% to about 20%, about 5% to about 15%, about 10% to about 50%, about 10% to about 45%, about 10% to about 40%, about 10% to about 35%, about 10% to about 30%, about 10% to about 25%, about 10% to about 20%, about 10% to about 15%, about 15% to about 50%, about 15% to about 45%, about 15% to about 40%, about 15% to about 35%, about 15% to about 30%, about 15% to about 25%, about 15% to about 20%, about 13% to about 17%, about 14% to about 16%, or about 14.9%.

In certain embodiments, the preparation formulation comprises water and a $Zn^{2+}$ salt (also referred to as Zn salt, salt of Zn, or salt of $Zn^{2+}$), in some embodiments said coating formulation comprises $ZnCl_2$, or $Zn(OAc)_2$, or $Zn_3(PO_4)_2$, or ZnCitrate or ZnOxalate or combinations thereof. Unless otherwise specified, the terms "preparation formulation", "coating formulation," and "coating solution" are interchangeable in this disclosure. The concentration of $Zn^{2+}$ salt (e.g., $ZnCl_2$) in the preparation formulation, for example, by weight to the total amount of the preparation formulation is about 0.01% to about 30%, 0.1% to about 30%, 0.3% to about 30%, about 0.5% to about 30%, about 0.8% to about 30%, about 1% to about 30%, about 1.5% to about 30%, about 2% to about 30%, about 5% to about 30%, 10% to about 30%, 15% to about 30%, about 20% to about 30%, about 25% to about 30%, about 0.01% to about 20%, 0.1% to about 20%, 0.3% to about 20%, about 0.5% to about 20%, about 0.8% to about 20%, about 1% to about 20%, about 1.5% to about 20%, about 2% to about 20%, about 5% to about 20%, 10% to about 20%, 15% to about 20%, about 0.01% to about 10%, 0.1% to about 10%, 0.3% to about 10%, about 0.5% to about 10%, about 0.8% to about 10%, about 1% to about 10%, about 1.5% to about 10%, about 2% to about 10%, about 5% to about 10%, about 0.01% to about 5%, 0.1% to about 5%, 0.3% to about 5%, about 0.5% to about 5%, about 0.8% to about 5%, about 1% to about 5%, about 1.5% to about 5%, about 2% to about 5%, about 0.01% to about 3%, 0.1% to about 3%, 0.3% to about 3%, about 0.5% to about 3%, about 0.8% to about 3%, about 1% to about 3%, about 1.5% to about 3%, about 2% to about 3%, about 0.01% to about 30%, 0.1% to about 30%, 0.3% to about 30%, about 0.5% to about 30%, about 0.8% to about 2%, about 1% to about 2%, about 1.5% to about 2%, about 0.01% to about 1%, 0.1% to about 1%, 0.3% to about 1%, about 0.5% to about 1%, about 0.8% to about 1%, or about 0.8%.

The weight abaloparatide in a coating formulation refers to the weight of the abaloparatide to the total coating formulation.

Certain embodiments of this disclosure describe a coating formulation wherein the excipient to abaloparatide is described as a mole ratio which is represented herein as "M" unless stated otherwise. For example, a coating solution described as 0.7 M $ZnCl_2$ indicates a mole ratio of $ZnCl_2$ to abaloparatide of 0.7 in the coating solution. For purposes of this calculation, the mole ratio is determined by calculation of the ratio of the specified excipient to abaloparatide in the coating solution.

The mole fraction ratio M in the coating solution can vary between about 0.1M and 4.4M or between about 0.35M and 4.4M or between about 0.35 and 3.0 M or between about 0.35M and 2.5M or between about 0.35M and 2.2M or between about 0.7M and 2.2M or is about 0.35M or about 0.5M or is about 0.7M or is about 1.4M or is about 2.2M or is about 2.9M or is about 3.6 M.

In certain embodiments, the coating formulation comprises a $Ca^{2+}$ salt wherein said $Ca^{2+}$ salt can include CaSorbate, CaCitrate, CaAscorbate, $Ca_3(PO_4)_2$, $CaCl_2$, $CaCO_3$, $CaSO_4$, $Ca(OAc)_2$ or combinations thereof. $Ca^{2+}$ salt is also referred to as Ca salt, salt of Ca, or salt of $Ca^{2+}$. The concentration of $Ca^{2+}$ salt (e.g., $CaSO_4$) in the preparation formulation, for example, by weight to the total amount of the preparation formulation is about 0.01% to about 30%, 0.1% to about 30%, 0.3% to about 30%, about 0.5% to about 30%, about 0.8% to about 30%, about 1% to about 30%, about 1.5% to about 30%, about 2% to about 30%, about 5% to about 30%, 10% to about 30%, 15% to about 30%, about 20% to about 30%, about 25% to about 30%, about 0.01% to about 20%, 0.1% to about 20%, 0.3% to about 20%, about 0.5% to about 20%, about 0.8% to about 20%, about 1% to about 20%, about 1.5% to about 20%, about 2% to about 20%, about 5% to about 20%, 10% to about 20%, 15% to about 20%, about 0.01% to about 10%, 0.1% to about 10%, 0.3% to about 10%, about 0.5% to about 10%, about 0.8% to about 10%, about 1% to about 10%, about 1.5% to about 10%, about 2% to about 10%, about 5% to about 10%, about 0.01% to about 5%, 0.1% to about 5%, 0.3% to about 5%, about 0.5% to about 5%, about 0.8% to about 5%, about 1% to about 5%, about 1.5% to about 5%, about 2% to about 5%, about 0.01% to about 3%, 0.1% to about 3%, 0.3% to about 3%, about 0.5% to about 3%, about 0.8% to about 3%, about 1% to about 3%, about 1.5% to about 3%, about 2% to about 3%, about 0.01% to about 30%, 0.1% to about 30%, 0.3% to about 30%, about 0.5% to about 30%, about 0.8% to about 2%, about 1% to about 2%, about 1.5% to about 2%, about 0.01% to about 1%, 0.1% to about 1%, 0.3% to about 1%, about 0.5% to about 1%, about 0.8% to about 1%, or about 0.8%.

The mole ratio M of the Ca salt in the coating solution can vary between about 0.1M and 4.4M or between about 0.35M and 4.4M or between about 0.35 and 3.0 M or between about 0.35M and 2.5M or between about 0.35M and 2.2M or between about 0.7M and 2.2M or is about 0.35M or about 0.5M or is about 0.7M or is about 1.4M or is about 2.2M or is about 2.9M or is about 3.6 M.

In some embodiments the coating solution comprises a $Mg^{2+}$ salt wherein said $Mg^{2+}$ salt can include MgO, MgCitrate, $MgSO_4$, MgOrotate, MgLactate, $MgCO_3$, $MgCl_2$, $Mg(OAc)_2$, or combinations thereof. $Mg^{2+}$ salt is also referred to as Mg salt, salt of Mg, or salt of $Mg^{2+}$. The concentration of $Mg^{2+}$ salt (e.g., $MgCl_2$) in the preparation formulation, for example, by weight to the total amount of the preparation formulation is about 0.01% to about 30%, 0.1% to about 30%, 0.3% to about 30%, about 0.5% to about 30%, about 0.8% to about 30%, about 1% to about 30%, about 1.5% to about 30%, about 2% to about 30%, about 5% to about 30%, 10% to about 30%, 15% to about 30%, about 20% to about 30%, about 25% to about 30%, about 0.01% to about 20%, 0.1% to about 20%, 0.3% to about 20%, about 0.5% to about 20%, about 0.8% to about 20%, about 1% to about 20%, about 1.5% to about 20%, about 2% to about 20%, about 5% to about 20%, 10% to about 20%, 15% to about 20%, about 0.01% to about 10%, 0.1% to about 10%, 0.3% to about 10%, about 0.5% to about 10%, about 0.8% to about 10%, about 1% to about 10%, about 1.5% to about 10%, about 2% to about 10%, about 5% to about 10%, about 0.01% to about 5%, 0.1% to about 5%, 0.3% to about 5%, about 0.5% to about 5%, about 0.8% to about 5%, about 1% to about 5%, about 1.5% to about 5%, about 2% to about 5%, about 0.01% to about 3%, 0.1% to about 3%, 0.3% to about 3%, about 0.5% to about 3%, about 0.8% to about 3%, about 1% to about 3%, about 1.5% to about 3%, about 2% to about 3%, about 0.01% to about 30%, 0.1% to about 30%, 0.3% to about 30%, about 0.5% to about 30%, about 0.8% to about 2%, about 1% to about 2%, about 1.5% to about 2%, about 0.01% to about 1%, 0.1% to about 1%, 0.3% to about 1%, about 0.5% to about 1%, about 0.8% to about 1%, or about 0.8%.

The mole ratio M of Mg in the coating solution can vary between about 0.1M and 4.4M or between about 0.35M and 4.4M or between about 0.35 and 3.0 M or between about 0.35M and 2.5M or between about 0.35M and 2.2M or between about 0.7M and 2.2M or is about 0.35M or about 0.5M or is about 0.7M or is about 1.4M or is about 2.2M or is about 2.9M or is about 3.6 M.

In some embodiments of this invention, a formulated patch ready to package and use (the initial coating solution dried to remove water) is provided wherein said formulated patch comprises a $Zn^{2+}$ salt. In certain embodiments the $Zn^{2+}$ salt is $Zn(OAc)_2$, in some embodiments the $Zn^{2+}$ salt is $ZnCl_2$, in certain embodiments it is $Zn_3(PO_4)_2$, in some embodiments it is ZnCitrate and in certain embodiments it is ZnOxalate or combinations thereof. In certain embodiments, the formulated patch is made by coating with the coating solution in one or multiple coating iterations and then drying said patch or allowing said patch to dry to a fairly constant weight and then characterizing said patch as weight by percent of the salt, the metal including its counterions. In certain embodiments, the coated patch, dried and ready to use comprises a Zn salt. In some embodiments, the Zn salt is a $Zn^{2+}$ salt, in some embodiments the Zn salt comprises between 0.5% to 30% w/w of the formulation, or from 1.0 to 20% w/w, from 1.5% to 15% w/w Zn salt. In some embodiments, the coated and dried patch comprises 1.5% to 10% w/w Zn salt, or 1.0%-10% w/w, 1.8%-8.5% w/w, or 1.9% to 5.9% w/w, or about 1.9% to 8.5% w/w, or about 2.0% to about 8% w/w, or 5% to 8% w/w, or is between 7-9%, or is between 1.7% to 2.25% w/w, or between 5% to 7% w/w, or about 7.7%, or about 5.8% w/w, or about 1.9% w/w.

In some embodiments of this invention, a formulated patch ready to package and use (the initial coating solution dried to remove water) is provided wherein said formulated patch comprises a $Ca^{2+}$ salt. In some embodiments the $Ca^{2+}$ salt is CaSorbate, CaCitrate, CaAscorbate, $Ca_3(PO_4)_2$, $CaCl_2$, $CaCO_3$, $CaSO_4$, $Ca(OAc)_2$ or combinations thereof. In certain embodiments, the formulated patch is made by coating with the coating solution in one or multiple coating iterations and then drying said patch or allowing said patch to dry to a fairly constant weight and then characterizing said patch as weight by percent of the salt, the metal including its counterions. In certain embodiments, the coated patch, dried and ready to use comprises from 1.0 to 20% Ca salt w/w of the formulation. In certain embodiments, said coated patch comprises from 1.5% to 15% Ca salt w/w. In some embodiments, the coated and dried patch comprises 1.5% to 10% Ca salt w/w, or 1.8%-8.5% w/w, or 1.9% to 5.9% w/w, or about 1.9% to 8.5% w/w, or about 2.0% to about 8% w/w, or 5% to 8% w/w.

In some embodiments of this invention, a formulated patch ready to package and use (the initial coating solution dried to remove water) is provided wherein said formulated patch comprises a $Mg^{2+}$ salt. In some embodiments the $Mg^{2+}$ salt is MgO, MgCitrate, $MgSO_4$, MgOrotate, MgLactate, $MgCO_3$, $MgCl_2$, $Mg(OAc)_2$, or combinations thereof. In certain embodiments, the formulated patch is made by coating with the coating solution in one or multiple coating iterations and then drying said patch or allowing said patch to dry to a fairly constant weight and then characterizing said patch as weight by percent of the salt, the metal including its counterions. In certain embodiments, the coated patch, dried and ready to use comprises from 0.5 to 15% Mg salt w/w salt to formulation excluding residual water. In certain embodiments, said coated patch comprises from 1.0% to 10% Mg salt w/w salt to formulation excluding residual water. In some embodiments, the coated and dried patch comprises 1.5% to 10% Mg salt w/w salt to formulation excluding residual water, or 1.8%-8.5% w/w salt to formulation excluding residual water, or 1.9% to 5.9% w/w salt to formulation excluding residual water, or about 1.9% to 8.5% w/w salt to formulation excluding residual water, or about 2.0% to about 8% w/w salt to formulation excluding residual water, or 5% to 8% w/w salt to formulation excluding residual water.

In certain embodiments, the formulated patch comprises two or more of the $Zn^{2+}$, $Ca^{2+}$ and/or $Mg^{2+}$ salts described immediately above.

Example of coating solution and patch formulation contents. Where ranges are presented below in the following examples, it should be appreciated that the formulations should be read to comprise the elaborated materials and may contain additional excipients (active or inert). Where a specific amount is provided such that the collective materials add up to 100%, it should be appreciated that the formulation should be read as consisting essentially of the elaborated ingredients in the listed ratios.

Example of Abaloparatide Coating Solution

| Component | Function | Weight (about) % |
| --- | --- | --- |
| Abaloparatide | API | 35.78 |
| Zinc Chloride, USP ($ZnCl_2$) | Excipient | 2.22 (approx. 2.2 mole ratio Zn to abaloparatide) |
| Sterile Water for Injection, USP | Solvent | 62.00 |
| Total | | 100 |

Example of Abaloparatide Formulation on Patch Ready to Use (After Drying)

| Component | Function | Weight (about)% |
| --- | --- | --- |
| Abaloparatide | API | 94.16 |
| Zinc Chloride, USP ($ZnCl_2$) | Excipient | 5.84 |
| Total | | 100 |

Example of Abaloparatide Coating Solution

| Component | Function | Weight (about) % |
| --- | --- | --- |
| Abaloparatide | API | 45.11 |
| Zinc Chloride, USP ($ZnCl_2$) | Excipient | 0.89 (approx. 0.7 mole ratio to abaloparatide) |
| Sterile Water for Injection, USP | Solvent | 54.00 |
| Total | | 100 |

Example of Abaloparatide Formulation on Patch Ready to Use (After Drying)

| Component | Function | Weight (about) % |
| --- | --- | --- |
| Abaloparatide | API | 98.07 |
| Zinc Chloride, USP ($ZnCl_2$) | Excipient | 1.93 |
| Total | | 100 |

Example of Abaloparatide Coating Solution

| Component | Function | Weight (about)% |
| --- | --- | --- |
| Abaloparatide | API | 30-65 |
| Zinc Chloride, USP ($ZnCl_2$) | Excipient | 0.5-8.5 |
| Sterile Water for Injection, USP | Solvent | 30-65 |

Example of Abaloparatide Formulation on Patch Ready to Use (After Drying)

| Component | Function | Weight (about) % |
| --- | --- | --- |
| Abaloparatide | API | 85-99 |
| Zinc Chloride, USP ($ZnCl_2$) | Excipient | 0.5-10 |

Example of Abaloparatide Formulation on Patch Ready to Use (After Drying)

| Component | Function | Weight (about)% |
| --- | --- | --- |
| Abaloparatide | API | 85-99 |
| Zinc Chloride, USP ($ZnCl_2$) | Excipient | 4.5-8.5 |

Example of Abaloparatide Formulation on Patch
Ready to Use (After Drying)

| Component | Function | Weight (about) % |
|---|---|---|
| Abaloparatide | API | 85-99 |
| Zinc Chloride, USP (ZnCl$_2$) | Excipient | 5-8 |

Example of Abaloparatide Coating Solution

| Component | Function | Weight (about) % |
|---|---|---|
| Abaloparatide | API | 40.62 |
| Zinc Acetate, USP | Excipient | 1.38 (about 0.7 mole ratio to abaloparatide) |
| Sterile Water for Injection, USP | Solvent | 58.00 |
| Total | | 100 |

Example of Abaloparatide Formulation on Patch
Ready to Use (After Drying)

| Component | Function | Weight (about) % |
|---|---|---|
| Abaloparatide | API | 96.7 |
| Zinc Acetate, USP | Excipient | 3.3 |
| Total | | 100 |

Example of Abaloparatide Formulation on Patch
Ready to Use (After Drying)

| Component | Function | Weight (about) % |
|---|---|---|
| Abaloparatide | API | 85-99 |
| Zinc Acetate USP Zn(OAc)$_2$ | Excipient | 0.5-10 |

Example of Abaloparatide Formulation on Patch
Ready to Use (After Drying)

| Component | Function | Weight (about) % |
|---|---|---|
| Abaloparatide | API | 85-99 |
| Zinc Acetate USP Zn(OAc)$_2$ | Excipient | 1.5-7.5 |

Example of Abaloparatide Formulation on Patch
Ready to Use (After Drying)

| Component | Function | Weight (about) % |
|---|---|---|
| Abaloparatide | API | 85-99 |
| Zinc Phosphate USP Zn$_3$(PO$_4$)$_2$ | Excipient | 0.5-10 |

Example of Abaloparatide Formulation on Patch
Ready to Use (After Drying)

| Component | Function | Weight (about) % |
|---|---|---|
| Abaloparatide | API | 85-99 |
| Ca$^{2+}$ salt | Excipient | 0.5-10 |

Example of Abaloparatide Formulation on Patch
Ready to Use (After Drying)

| Component | Function | Weight (about) % |
|---|---|---|
| Abaloparatide | API | 85-99 |
| Ca$^{2+}$ salt | Excipient | 0.5-10 |

Example of Abaloparatide Coating Solution

| Component | Function | Weight (about) % |
|---|---|---|
| Abaloparatide | API | 40.5 |
| Polyethylene Glycol 3350 NF | Excipient | 14.5 |
| Sterile Water for Injection, USP | Solvent* | 45.00 |
| Total | | 100 |

Example of Abaloparatide Formulation on Patch
Ready to Use (After Drying)

| Component | Function | Weight % (about) |
|---|---|---|
| Abaloparatide | API | 73.64 |
| Polyethylene Glycol 3350 NF | Excipient | 26.36 |
| Total | | 100 |

Example of Abaloparatide Coating Solution

| Component | Function | Weight % (about) |
|---|---|---|
| Abaloparatide | API | 34.84 |
| Polyethylene Glycol 3350 NF | Excipient | 12.47 |
| Zinc Chloride, USP | Excipient | 0.69 |
| Sterile Water for Injection, USP | Solvent | 52 |
| Total | | 100 |

Example of Abaloparatide Formulation on Patch Ready to Use (After Drying)

| Component | Function | Weight (about) % |
|---|---|---|
| Abaloparatide | API | 72.58 |
| Polyethylene Glycol 3350 NF | Excipient | 25.98 |
| Zinc Chloride, USP | Excipient | 1.44 |
| Total | | 100 |

Example of Abaloparatide Coating Formulation for PEG, PVP, CD and Histidine

| No. | Excipient | MW | Concentration in the transdermal formulation for coating | Molar ratio excipient/ abaloparatide |
|---|---|---|---|---|
| 1. | PEG | 3,000-3,700 | About 2.8-about 15% (by weight) | 0.09-0.52 |
| 2. | PVP | 7,000-11,000 | About 600 mg/mL | Not determined |
| 4. | CD | Approx. 1410 | About 1.3-about 13.3% (by weight) | About 0.08-about 1.1 |
| 6. | Histidine (e.g., monohydrochloride monohydrate) | 209.6 | About 2-bout 5% (by weight) | About 1.4-about 3.4 |

Example of Abaloparatide Formulation on Patch Ready to Use (After Drying)

| No. | Excipient | MW | Concentration in the transdermal formulation for coating | % weight in final ready to use patch |
|---|---|---|---|---|
| 1. | PEG | 3,000-3,700 | About 2.8-about 15% (by weight) | About 6-about 30 |
| 2. | PVP | 7,000-11,000 | About 600 mg/mL | Not determined |
| 4. | CD | Approx. 1410 | About 1.3-about 13.3% (by weight) | About 3-about 30 |
| 6. | Histidine (e.g., monohydrochloride monohydrate) | 209.6 | About 2-bout 5% (by weight) | About 5-about 13 |

Coating solution, doses and sites of administration for clinical studies described herein.

| Cohort | Formulation | Dose | Anatomical Site |
|---|---|---|---|
| 1 | ZnCl$_2$ | 100 | Abdomen |
| | | 150 | |
| | | 200 | |
| 2 | PEG | 100 | Abdomen |
| | | 150 | |
| | | 200 | |
| 3 | ZnCl$_2$/PEG | 100 | Abdomen |
| | | 150 | |
| | | 200 | |
| 4 Period 1 | ZnCl$_2$ | 200 | Thigh |
| 4 Period 2 | ZnCl$_2$/PEG | 200 | Thigh |
| 4 Period 3 | ZnCl$_2$ | 2 × 150 | Abdomen |
| 5 Period 1 | ZnCl$_2$ | 200 | Thigh |
| 5 Period 2 | Zn(OAc)$_2$ | 200 | Thigh |
| 5 Period 3 | ZnCl$_2$ | 260 | Thigh |
| 5 Period 4 | ZnCl$_2$ | 2 × 200 | Thigh |

In certain embodiments, the preparation formulation comprises histidine (e.g., monohydrochloride monohydrate). The concentration of histidine (by weight to the total amount of the preparation formulation) is about 1% to about 15%, about 1% to about 10%, about 1% to about 5%, about 3% to about 15%, about 3% to about 10%, about 3% to about 5%, about 5% to about 15%, about 5% to about 10%, about 3%, about 5%, or about 10%.

In certain embodiments, the preparation formulation comprises two or three excipients selected from the group consisting of PEG, ZnCl$_2$, and histidine, wherein the concentration of each excipient is the same as disclosed herein.

In certain embodiments, the preparation formulation comprises two excipients selected from the group consisting of PEG, ZnCl$_2$, and histidine, e.g., a combination of PEG and ZnCl$_2$, a combination of histidine and PEG, and a combination of histidine and ZnCl$_2$.

In certain embodiments, the preparation formulation comprises a combination of PEG, ZnCl$_2$, and histidine.

In certain embodiments, the preparation formulation comprises abaloparatide at a concentration of about 5% to about 15%, about 12.5% to about 20%, about 15% to about 60%, about 40% to about 48%, about 43% to about 48%, about 40% to about 46%, about 40% to about 52%, about 46% to about 48%, about 46% to about 52%, about 50% to about 62%, about 52% to about 60%, or about 54% to about 58% by weight.

In certain embodiments, the preparation formulation for abaloparatide has a viscosity at 25° C. of greater than about 500 centipoise, greater than about 550 centipoise, greater than about 600 centipoise, greater than about 700 centipoise, greater than about 800 centipoise, greater than about 900 centipoise, greater than about 1,000 centipoise, greater than about 1,500 centipoise, greater than about 2,000 centipoise, greater than about 10,000 centipoise, about 500 to about 5,000 centipoise, about 500 to about 2,000 centipoise, or about 500 to about 1,000 centipoise, about 550 to about 5,000 centipoise, about 550 to about 2,000 centipoise, or about 550 to about 1,000 centipoise.

In certain embodiments, the preparation formulations disclosed herein further comprise a bioactive peptide or protein. In certain embodiments, the preparation formulations disclosed herein comprise an antibody.

II. Transdermal Patches

Provided herein in certain embodiments are transdermal patches for administration of abaloparatide comprising one or more microprojections prepared using a preparation formulation as disclosed herein, wherein transdermal delivery of abaloparatide using the patch can provide a pharmacokinetic profile, in some instances substantial bioequivalence or bioequivalence to subcutaneous delivery of abaloparatide at a given dose. n certain embodiments, the transdermal delivery of abaloparatide produces substantial bioequivalence or bioequivalence to a subcutaneous delivery of abaloparatide at the dosage of about 20 μg to about 250 μg, about 20 μg to about 200 μg, about 40 μg to about 120 μg, about 60 μg to about 100 µg, about 70 µg to about 90 µg, about 80 µg, about 100 µg, about 150 µg, or about 200 µg.

In certain embodiments, transdermal delivery of abaloparatide produces substantial bioequivalence or bioequivalence to the abaloparatide-SC treatment For a given dosage, the patch formulation embodiments comprising one or more excipients as described herein can deliver, after administration, a $C_{max}$ that is higher than a patch formulation without the one or more excipient(s) (eg plain buffered formulation such as PBS buffer), the $C_{max}/C_{max}$ ratios of >1; or >1.2; or >1.5; or between 1.2-1.5 at a given dosage and/or and AUC/AUC ($_{last}$ and/or $_{inf}$)>1; or >1.2; or >1.5 or between 1.2-1.5 at a given dosage.

In some embodiments, the transdermal patches are designed for active delivery of the abaloparatide using an external energy source.

In certain embodiments, the preparation formulation of abaloparatide is used to prepare one or more microprojections on a transdermal patch, resulting in the transdermal patches comprising abaloparatide. For example, at least part of the one or more microprojections on the transdermal patch comprises abaloparatide. In certain embodiments, at least part of the one or more microprojections on the transdermal patch further comprises one or more excipients selected from the group consisting of PEG, $ZnCl_2$ and histidine.

In certain embodiments, the amount of each excipient per patch is about 1 µg to about 300 µg, about 10 µg to about 300 µg, about 100 µg to about 300 µg, about 200 µg to about 300 µg, about 1 µg to about 200 µg, about 10 µg to about 200 µg, about 100 µg to about 200 µg, about 150 µg to about 200 µg, about 1 µg to about 150 µg, about 10 µg to about 150 µg, about 100 µg to about 150 µg, about 1 µg to about 100 µg, about 10 µg to about 100 µg, about 50 µg to about 100 µg, about 1 µg to about 50 µg, about 10 µg to about 50 µg, about 20 µg to about 50 µg, about 1 µg to about 20 µg, about 10 µg to about 20 µg, about 15 µg to about 20 µg, about 1 µg, about 5 µg, about 10 µg, about 20 µg, about 30 µg, about 40 µg, about 50 µg, about 60 µg, about 70 µg, about 80 µg, about 90 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, or about 300 µg.

In certain embodiments, the amount of abaloparatide) per ready to use patch (a patch that has been processed through manufacturing and is pharmaceutically suitable for use) is about 100-450 µg; or about 150-375 µg; or about 200-400 µg, or about 200-350 µg, or about 250-350 µg, or about 160-240 µg, or about 200-300 µg, or about 220-330 µg, or about 240-360 µg, or about 260-390 µg, or about 280-420 µg, or about 300-450 µg, or about 320-480 µg, or about 180-220 µg, or about 225-275 µg, or about 247.5-302.5 µg, or about 270-330 µg, or about 282.5-357.5 µg, or about 315-385 µg, or about 337.5-412.5 µg, or about 360-440 µg, or about 382.5-467.5 µg, or about 405-495 µg, about 200 µg, about 210 µg, about 220 µg, about 230 µg, about 240 µg, about 250 µg, about 260 µg, about 270 µg, about 280 µg, about 290 µg, or about 300 µg.

In certain embodiments, the transdermal patches provided herein comprise a plurality of these microprojections. The term "microprojection" as used herein refers to a piercing element of any shape or size on a transdermal patch that is capable of piercing the stratum corneum of the skin. These small piercing elements can have various materials, shapes and dimensions. In certain embodiments, one or more of the microprojections on the disclosed transdermal patches are microneedles. The term "microneedle" as used herein refers to a microprojection comprising a base and a tip, wherein the tip has a smaller diameter, width, perimeter or circumference than the base. A transdermal patch comprising one or more microneedles may also be referred to as a "transdermal microneedle patch" or a "microneedle transdermal patch."

The microprojection patches of certain embodiments of this disclosure can be of different shapes, for example polygonal, rectangular, circular, etc. The patches can vary in area to meet the particular need of the situation. The patch size may be referred to as the area on the patch. In some embodiments, the area is defined as the area forming a continuous boundary and in direct contact with the base of the microprojections or molded together with the microprojections ("the support area" as by A-B in FIG. 43). Alternatively, the area of the patch can be defined by the outermost perimeter drawn around the bases of the microprojections themselves. This perimeter will generally be less than the perimeter of the support area as discussed above as most if not all of the outermost (perimeter) needles will not extend to the perimeter of the microneedle support area but still falls within the area ranges described herein. Or, the patch area is the area that contacts the patient's skin but does not include adhesive.

In certain embodiments, the support area of the patch is circular and the patch size can be characterized by the diameter across the patch portion that supports the microneedles and excludes additional diameter from portions of the patch not in direct support of the needle layer, for example, an adhesive portion of the patch. Patch diameters (to the support area of which is circular) of certain embodiments of this disclosure will fall within a range of between 0.75 and 2.5 cm in diameter. In some embodiments, a patch diameter is from about 1 cm to about 1.6 cm in diameter, or about 1.4 cm to about 1.6 cm, or about 1.4 cm, or about 1.25 or about 1.5 cm or about 1.6 cm or about 1.8 cm or about 1.9 cm. The area of a patch (with any shape of the support area) can be about 0.2 $cm^2$ to about 3 $cm^2$, or about 0.8 $cm^2$ to about 2 $cm^2$, or about 1.0 $cm^2$ to about 2 $cm^2$, or about 0.8 $cm^2$, or about 0.9 $cm^2$, or about 1.1 $cm^2$, or about 1.3 $cm^2$, or about 1.5 $cm^2$, or about 1.8 $cm^2$, or about 2.0 $cm^2$, or about 2.5 $cm^2$, or about 2.8 $cm^2$, or about 3.0 $cm^2$, or about 0.8 $cm^2$ to about 3 $cm^2$, or about 1.26 $cm^2$, or about 2.52 $cm^2$.

The described patch areas and patch area ranges cover a single patch, or can also define multiple patches administered within a short time of each other (such as to be considered a single drug administration) and in such instances the area of the patch administered will be the sum of the two or more patches administered within close simultaneity, for example within 5-30 seconds of each other, or at least within 1 minute. A microprojection (e.g., microneedle) in the transdermal patches provided herein may have any size, shape, or design commonly used in the art. In certain embodiments, the microprojections have their greatest diameter, width, perimeter, or circumference at the base. In certain embodiment, the microprojections have a tapered design, meaning that the microprojection from base to tip reflects a relatively constant narrowing over the length. In certain embodiments, the ratio of the diameter, width, perimeter, or circumference at the base of the microprojection to the diameter, width, perimeter, or circumference at the tip of the microneedle is greater than 2. In other embodiments, the ratio is greater than 4 or greater than 6. In certain embodiments, the microprojections have a generally circular perimeter about the axis that is broader at the base than the tip. In certain embodiments, the microprojections are pyramidal in shape, with an approximately rectangular base that tapers to an apex, wherein said apex is approximately rectangular. In certain embodiments, the microprojections are pyramidal in shape, with a square base that tapers to an apex wherein said apex is approximately square. In certain embodiments, the microprojections are pyramidal in shape with a rectangular or square base and a shape that is not readily characterized as rectangular or square at the top. In certain embodiments, the width at the base of the microprojections is greater than the length of the needle (aspect ratio of the protrusion). In certain embodiments, the aspect ratio is about 2:1, about 3:1 or about 4:1.

The microprojections on a given patch will generally have the same length but different microprojection patches may contain microprojections of various lengths, e.g., about 30 µm to about 1,500 µm, about 50 µm to about 1,500 µm, about 100 µm to about 1,500 µm, about 250 µm to about 1,500 µm, about 500 µm to about 1,500 µm, about 600 µm to about 1,500 µm, about 750 µm to about 1,500 µm, about 800 µm to about 1,500 µm, about 1,000 µm to about 1,500 µm, about 30 µm to about 1.00 µm, about 50 µm to about 1,500 µm, about 30 µm to about 1,000 µm, about 50 µm to about 1,000 µm, about 750 µm to about 1,200 µm, about 800 µm to about 1,200 µm, about 100 µm to about 1,000 µm, about 250 µm to about 1,000 µm, about 500 µm to about 1,000 µm, about 600 µm to about 1,000 µm, about 750 µm to about 1,000 µm, about 800 µm to about 1,000 µm, about 30 µm to about 750 µm, about 50 µm to about 750 µm, about 100 µm to about 750 µm, about 250 µm to about 750 µm, about 500 µm to about 750 µm, about 600 µm to about 750 µm, about 600 µm to about 800 µm, about 30 µm to about 600 µm, about 50 µm to about 600 µm, about 100 µm to about 600 µm, about 250 µm to about 600 µm, about 500 µm to about 600 µm, about 30 µm to about 500 µm, about 50 µm to about 500 µm, about 100 µm to about 500 µm, about 250 µm to about 500 µm, about 30 µm to about 250 µm, about 50 µm to about 250 µm, about 100 µm to about 250 µm, about 30 µm to about 50 µm, about 100 µm to about 150 µm, about 200 µm, about 250 µm, about 300 µm, about 500 µm, about 750 µm, or about 1,500 µm. In certain embodiments the length is between 300-1,000 µm, 600-1,000 µm, 400-600 µm, or about 500 µm, or about 750 µm.

Microprojections on the transdermal patches provided herein can be made from any suitable material, including for example carbon, polymers, metals, or a combination thereof, to achieve a desirable flexural modulus. In some embodiments, the microprojection has a flexural modulus of greater than 1,000 MPa, greater than 2,000 MPa, greater than 3,000 MPa, or between 3,000 MPa and 15,000 MPa. As used herein, "ISO 178" refers to ISO test standards for determination of flexural properties of plastics.

In certain embodiments, the transdermal patches provided herein comprise a first backing layer on which the microprojections are arrayed. In these embodiments, the microprojections may be affixed to or integral with the first backing layer. In certain embodiments, the microprojections are made from the same material as the first backing layer. For example, the microprojections may be formed by etching or punching from the first backing layer. In certain embodiments, the microprojections are made by an injection molding process. In other embodiments, the microprojections may be made of a different material than the first backing layer. In certain of these embodiments, the microprojections are affixed to the first backing layer via an adhesive. In certain of these embodiments, the microprojections are detachable from the first backing layer and/or the second backing layer.

In certain embodiments, the transdermal patches provided herein further comprise a second backing layer on which the first backing layer is affixed. The second backing layer may be flexible or inflexible.

In certain embodiments, the transdermal patches provided herein comprise an adhesive material to facilitate the patch staying in place on a subject's skin before and/or during transdermal administration of abaloparatide. In certain of these embodiments, the adhesive material is comprised on the first and/or second backing layer(s).

In certain embodiments of the transdermal patches provided herein, the vertical axis of the one or more microprojections extends at an angle of at least 45 degrees or at least 60 degrees from the first and/or second backing layer(s). In some embodiments, the microprojections are perpendicular to the first and/or second backing layer(s).

In certain embodiments of the transdermal patches provided herein, the patches have a microprojection density of about 20 to about 2,000 microprojections per $cm^2$, about 50 to about 2,000 microprojections per $cm^2$, about 100 to about 2,000 microprojections per $cm^2$, about 250 to about 2,000 microprojections per $cm^2$, about 500 to about 2,000 microprojections per $cm^2$, about 750 to about 2,000 microprojections per $cm^2$, about 1,000 to about 2,000 microprojections per $cm^2$, about 1,500 to about 2,000 microprojections per $cm^2$, about 300 to about 500 microprojections per $cm^2$. In certain embodiments, the patches comprise about 50 to about 4,000 microprojections, about 100 to about 4,000 microprojections, about 250 to about 4,000 microprojections, the patches comprise about 1,400 to about 4,000 microprojections, about 1,600 to about 4,000 microprojections, about 2,000 to about 4,000 microprojections, about 3,000 to about 4,000 microprojections, about 3,500 to about 4,000 microprojections, the patches comprise about 50 to about 3,500 microprojections, about 100 to about 3,500 microprojections, about 250 to about 3,500 microprojections, about 1,400 to about 3,500 microprojections, about 1,600 to about 3,500 microprojections, about 2,000 to about 3,500 microprojections, about 3,000 to about 3,500 microprojections, about 50 to about 3,000 microprojections, about 100 to about 3,000 microprojections, about 250 to about 3,000 microprojections, about 1,400 to about 3,000 microprojections, about 1,600 to about 3,000 microprojections, about 2,000 to about 3,000 microprojections, about 50 to about 600 microprojections per $cm^2$, about 100 to about 500 microprojections per $cm^2$, about 150-350 microprojections per $cm^2$, about 250 to about 400 microprojections per $cm^2$, about 300 to about 375 microprojections per $cm^2$, about 300 to about 750 microprojections about 366 microprojections per $cm^2$, about 316 microprojections per $cm^2$, or about 320 microprojections per $cm^2$, or about 250 microprojections per $cm^2$.

In certain embodiments, the transdermal patch containing abaloparatide comprises at least one microprojection at least partially coated with abaloparatide (hereinafter the "coated microprojection").

The term "coated" as used herein with regard to an individual microprojection means that the microprojection comprises abaloparatide on at least part of its surface. In certain embodiments, the microprojection comprises an abaloparatide composition on about 1% to about 100%, 1% to about 80%, about 1% to about 50%, about 2% to about 40%, about 5% to about 35%, about 5% to about 50%, about 30% to about 50%, about 10% to about 30%, about 15% to about 20%, or about 30% to about 50% of the total surface area of the microneedle, or about 1-100%, or about 1-80%, or about 1-50%, or about 2-40%, or about 35% of its surface. In certain embodiments, the microprojection comprises abaloparatide on about 30% to about 50% of the top of the microprojection (as used herein, "top" means the end of the microprojection which would contact the skin).

The term "coated" as used herein with regard to a plurality of microprojections means that two or more of the microprojections in the plurality are coated as the term is used above with regard to an individual microprojection. In certain embodiments, more than 10%, more than 20%, more than 30%, more than 40%, more than 50%, more than 60%, more than 70%, more than 80%, or more than 90% of the microprojections in a plurality of microinjections are coated, about 1 to about 100%, about 1% to about 80%, about 1% to about 50%, about 2% to about 40%, in certain embodiments, about 1% to about 100%, 1% to about 80%, about 1% to about 50%, about 2% to about 40%, about 5% to about 35%, 10% to about 30%, 15% to about 20%, or about 30% to about 50% of the total microprojection surface area in the plurality of microprojections are coated. "Microprojection surface area" as used herein refers to the combined surface area of all microprojections on a single transdermal patch.

In certain embodiments, a transdermal patch comprising one or more coated microprojections may further comprise abaloparatide on at least part of its surface of the first backing layer. For example, the transdermal patch comprises an abaloparatide composition on more than about 1% to about 100%, 1% to about 80%, about 1% to about 50%, about 2% to about 40%, about 5% to about 35%, 10% to about 30%, 15% to about 20%, or about 30% to about 50% of its total surface area of the first backing layer.

In certain embodiments, the transdermal patch of abaloparatide=comprises at least one microprojection comprising a plurality of layers arranged roughly parallel (e.g. at least about 80% parallel, at least about 90% parallel, or at least about 95% parallel) to the first backing layer, and at least one layer of the plurality of layers comprises abaloparatide (hereinafter the "active agent layer") (hereinafter the "layered microprojection"). In such cases, it is understood that when the layered microprojection(s) penetrate the skin, the active agent layer may dissolve in the tissue matrix thus delivering the active agent. In certain embodiments, the preparation formulation further comprises other materials (e.g., soluble polymers that are typically physiologically inactive) used to form the active agent layer and provide its structure.

In certain embodiments, the first backing layer of the transdermal patch comprising at least one layered microprojection further comprises an active agent layer. In certain embodiments, the active agent layer forms a tip of the microprojection which can penetrate through the stratum corneum for the transdermal delivery. The tip of the microprojection may adopt any shape as disclosed supra regarding the shapes of microprojections (e.g., pyramid, square, rectangle, etc.).

In other embodiments, the microprojection provided herein comprises a reservoir that is in fluid communication with the skin when applied to the subject. The reservoir is loaded with abaloparatide to be administered. The reservoir may be an inner space of the microprojection in fluid communication with the skin when applied, e.g., microprojections comprising a hollow portion. In certain embodiments, the hollow portion may have a side-opening.

In certain embodiments, the transdermal patches disclosed herein comprise a plurality of microprojections wherein at least one microprojection (e.g., microneedles) in the array is covered at least in part by a coating, said coating comprising a therapeutically active substance and one or more excipients selected from the group consisting of $Zn^{2+}$ salts, $Mg^{2+}$ salts, $Ca^{2+}$ salts, polyethylene glycols and hydroxypropyl beta-cyclodextrins. In certain embodiments, the therapeutically active substance comprises a bioactive peptide or protein. In certain embodiments, the therapeutically active substance comprises an antibody. In certain embodiments, the one or more excipients the transdermal patches disclosed herein has are selected from the group consisting of $ZnCl_2$, $Zn(OAc)_2$, $Zn_3(PO_4)_2$, ZnCitrate, ZnOxalate, MgO, MgCitrate, $MgSO_4$, MgOrotate, MgLactate, $MgCO_3$ CaSorbate, CaCitrate, CaAscorbate, $Ca_3(PO_4)_2$, $CaCl_2$, $CaCO_3$, $CaSO_4$, and $Ca(OAc)_2$. In certain embodiments, the one or more excipients the transdermal patches disclosed herein has are selected from the group consisting of $ZnCl_2$ and $Zn(OAc)_2$ and combinations thereof. In certain embodiments, the transdermal patches disclosed herein have a molar ratio of the excipient or excipients to the abaloparatide from the range of about 0.1 to about 3.0, about 0.2 to about 2.5, or about 0.25 to about 1.0.

Transdermal patches may also be prepared as disclosed in U.S. application Ser. Nos. 14/361,787, 14/361,802, 13/452,412, 13/791,170, 13/791,360, which are incorporated herein by reference in their entirety, including drawings.

The coated patches as embodied herein include one or more of the excipient embodiments described herein that can act to affect the release of the bioactive (eg abaloparatide) into the circulation to achieve the desired therapeutic ends.

III. Method of Preparing Transdermal Patches

Provided herein in certain embodiments are methods of preparing a transdermal patch for administration of abaloparatide as disclosed herein, comprising preparing at least one microprojection on a transdermal patch with a preparation formulation disclosed herein. In certain embodiments the microprojections are microneedles. In certain embodiments, the abaloparatide comprises, consists of, or consists essentially of abaloparatide. In certain embodiments, the transdermal delivery of abaloparatide produces substantial bioequivalence or bioequivalence to a subcutaneous delivery of abaloparatide at the dosage of about 20 µg to about 200 µg, about 40 µg to about 120 µg, about 60 µg to about 100 µg, about 70 µg to about 90 µg, or about 80 µg. In certain embodiments the transdermal delivery of abaloparatide produces substantial bioequivalence or bioequivalence to the abaloparatide-SC treatment.

In certain embodiments, the preparation methods provided herein comprise contacting one or more microprojections on a blank (i.e., previously free of abaloparatide) transdermal patch with the preparation formulations provided herein. In certain of these embodiments, the microprojections are coated by contacting a preparation formulation disclosed herein. In some embodiments, the contacting with the preparation formulation is accomplished by dipping a blank transdermal patch into the preparation formulation, then removing the patch and allowing it to dry.

In some embodiments, the preparation formulation is sprayed or brushed onto the microprojections and dried.

In certain of these embodiments, the microprojections are layered microprojections and are prepared by casting or depositing the layers onto the first and/or second backing layer, then removing the patch and allowing it to dry.

In certain embodiments, accelerated drying conditions are applied to the transdermal patch, including for example circulating air flow, desiccants, vacuum, and/or heat.

IV. Method of Treatments

Provided herein in certain embodiments are methods of treating osteoporosis, osteopenia, and osteoarthritis, improving bone mineral density (BMD), improving trabecular bone score (TBS), and/or treating, preventing, and/or reducing bone fractures in a subject comprising transdermally administering a therapeutically effective amount of abaloparatide comprised in a preparation formulation provided herein. While not being limiting to the types of osteoporosis that can be treated, the osteoporosis can be postmenopausal osteoporosis as well as severe postmenopausal osteoporosis. The osteoporosis can also be male osteoporosis. The osteoporosis in males and females can be due to hypogonadism or where hormone levels are gonadal but, for example, the patient is being treated with an anti-hormonal agent or the patient's hormonal response to a eugonadal level of hormones is for some reason attenuated. The osteoporosis to be treated can be caused by nutritional deficiencies or taking other drugs that cause bone loss, for example, corticosteroids. Patients can be treated where presented either with low bone mineral density in one or more sites where said bone mineral density falls one standard deviation below the norm, or two standard deviations below the norm or three or more standard deviations below the norm. In addition, patients even with normal bone mineral density may be at high risk for fracture due to the quality of bone they have. If bone is of low quality, it might appear to be normal from a bone mineral density perspective but due to any number of structural and/or physiochemical factors may place the patient at higher risk. Relatedly, a patient may be at high risk who has a history of one or more fractures. Accordingly, the patient can be recommended for treatment by the methods and products of certain embodiments of this disclosure. The prevention or treatment of different types of fractures are supported by the methods and products described herein. For example, treating and/or preventing vertebral, non-vertebral, clinical and/or major osteoporotic fractures are features of the disclosed methods and products. The osteoporosis treatments described herein can be accomplished by, for example, the once daily administration of a microprojection patch as described herein, and in some embodiments, microprojection arrays that after administration that result in a bioequivalent or substantially bioequivalent profile to a SC injection, for example, an 80 ug sc injection of abaloparatide.

Certain embodiments of the methods disclosed herein also include the treatment of osteoarthritis in a person in need thereof comprising the administration of a microprojection patch comprising abaloparatide and one or more of the configurations, formulations, etc described in this disclosure. In some embodiments the osteoarthritis being treated is associated with the patient's knee(s) and/or elbow(s) and/or wrist(s) and/or shoulder(s). In some of the methods of treatment, the osteoarthritis is primary and in some embodiments it is secondary and in certain embodiments it is undetermined.

Certain embodiments of the methods disclosed herein also include the use of the microprojection arrays as described herein in their various embodiments to accelerate fracture healing in a patient who has suffered one or more fractures and for which the fractures are not completely healed. Healing of bone fractures (eg long bone fractures) involves endochondral and intramembranous bone formation, which together form a callus that achieves union, stabilization, and gradual recovery of bone strength. Preclinically, abaloparatide at 5 or 25 ug/kg/d (sc daily) has been shown to accelerate fracture healing in a rat femur fracture model. Sixteen rats from each group were necropsied after 4 and 6 weeks of healing, with 12 fractured femurs per group used for micro-CT and biomechanical testing and the other 4 femurs used for micro-CT and histology. Semi-quantitative histologic scoring of cortical bridging across the fracture gap showed significantly greater bridging in the abaloparatide 5 or 25 ug/kg/d groups at week 4 compared with VEH controls. Histomorphometry at week 4 indicated significantly greater callus area in the abaloparatide 5 ug/kg/d and abaloparatide 25 ug/kg/d groups, which persisted at week 6 for the abaloparatide group, compared to VEH. Micro-CT of fracture calluses showed that the abaloparatide 5 and 25 ug/kg/d groups had significantly greater callus bone volume, bone volume fraction, and BMC at weeks 4 and 6, compared to VEH. Three-point bending tests at week 4 indicated that callus stiffness was 60% and 96% higher in the abaloparatide 5 and 25 ug/kg/d groups, respectively (both $P<0.05$ vs VEH). At week 6, callus stiffness was 112% higher in the abaloparatide 5 ug/kg/d group ($P<0.05$ vs VEH). Callus peak load was 77% higher in the abaloparatide 25 ug/kg/d group at week 4 ($P<0.05$ vs VEH), and remained numerically higher in both abaloparatide groups at week 6 compared with VEH. Together these data suggest systemically administered abaloparatide can enhance local healing in a preclinical fracture model.

Certain embodiments of the methods disclosed herein also include the use of the microprojection arrays as described herein in their various embodiments to accelerate fracture healing in a patient who has suffered one or more fractures and for which the fractures are not completely healed. In some instances, the patient is treated soon after the fracture in order to accelerate and/or help ensure the proper healing of the fracture. In certain embodiments, the patient has an identified fracture that has not properly healed over a period of time and is treated with certain microprojection embodiments disclosed herein. The administration can be once per day up to twice per day spaced out by at least eight hours. The number of days can vary depending on the needs of the particular patient. In some embodiments, the patient is treated, once or twice daily, every day for a period of 18 months, or 12 months, 6 months, 4, months, 3 months, 2 months, or between 1 month and 12 months, or 2 months-6 months. Alternatively, the treating physician or institution can monitor the bone fracture and continue treatment until a satisfactory result is maintained. In some embodiments, the patient is treated until the fracture is closed and in some embodiments, the treatment is continued until no more ameliorative effect is observed. For example, the fracture may close to an extent but not completely or may close in some spaces between the fracture but not completely. The result of the treatment can be shown in many ways including a reduced re-fracture rate at the same site (compared to the expected or a control rate), a radiographically detected improvement in the fracture (eg closing of the fracture), reduction in pain, reduced time to re-use of the affected area, etc.

The term "subject" as used herein refers to a mammalian subject. Examples of suitable subjects include, without limitation, subjects with one or more conditions selected from the group consisting of osteopenia, glucocorticoid-induced osteopenia, osteoporosis, glucocorticoid-induced osteoporosis, osteoarthritis, bone fractures, and high cortical porosity (e.g., subjects with diabetes, especially type II diabetes), female mammals, male mammals, dogs, cats, humans, men, women, women with osteoporosis, postmenopausal women, postmenopausal women with osteoporosis, mammals with high cortical porosity, and men and women with high cortical porosity.

As used herein, the term "cortical porosity" means the fraction of the cortical bone volume that is not occupied by the bone. The cortical porosity may be measured by Digital X-ray radiogrammetry (DXR) or other methods to provide an estimation of the local intensity minima ("holes") in the cortical bone regions using a recursive (climbing) algorithm starting from the outer region (Dhainaut 2013). A combined porosity measure is derived from the area percentage of holes found in the cortical part relative to the entire cortical area, by averaging over the involved bones and scaled to reflect a volumetric ratio rather than the projected area. A "high cortical porosity" means a porosity of about 10% higher, about 15% higher, about 20% higher, about 50% higher, about 100% higher, or about 150% higher than that of healthy subjects from the same age group as controls. For example, the subject may have a cortical porosity of about 0.01256, which the control group has a cortical porosity of about 0.01093 (Dhainaut 2013). Subjects with type II diabetes may have a cortical porosity up to twice that of controls (Oei 2013). Subject may have normal BMD or slightly lower BMD while have high cortical porosity.

Examples of bones which may exhibit improved BMD and/or TBS following the transdermal delivery of abaloparatide, without limitation, the lumbar spine, total hip, wrist, femur, cortical bone of the femur (femoral diaphysis), and/or femoral neck in the subject.

The transdermal delivery of abaloparatide may be administered at any treatment interval necessary for therapeutic effectiveness. In certain embodiments, the transdermal delivery of abaloparatide is administered on a daily basis. In other embodiments, the transdermal delivery of abaloparatide may be administered every other day, every 3rd day, every 4th day, every 5th day, once a week, or once or twice a month. One of ordinary skill in the art will recognize that the treatment interval may vary over the course of treatment. For example, the transdermal delivery of abaloparatide may be administered more frequently at the start of treatment, then less frequently over time as one or more therapeutic benchmarks are achieved. Alternatively, the transdermal delivery of abaloparatide may be administered less frequently at the start of treatment, with the treatment interval decreasing over time.

In those embodiments of the methods provided herein wherein the transdermal delivery of abaloparatide is administered using a transdermal patch provided herein. The transdermal patch may be placed in contact with the skin for any period of time necessary to achieve satisfactory analogue delivery. In certain embodiments, the transdermal patch may remain in contact with the skin for about 1 second to about 30 seconds, about 1 second to about 1 minute, about 15 second to about 30 seconds, about 15 second to about 1 minute, about 30 second to about 1 minute, about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, at least 60 minutes, at least 75 minutes, at least 90 minutes, or at least 120 minutes. In certain embodiments, two or more transdermal patches may be placed in contact with the skin in a sequential manner to achieve the desired dose and/or profile.

In certain embodiments of the methods provided herein, the treatment is carried out for a set period determined in advance. In other embodiments, the treatment is carried out until one or more therapeutic benchmarks are reached. Examples of a suitable timeframe for treatment include, without limitation, 6 weeks, 12 weeks, 3 months, 24 weeks, 6 months, 48 weeks, 12 months, 18 months, and 24 months. In certain embodiments, the treatment is carried out via once a day administration of a transdermal patch for 18 months.

In certain embodiments, the abaloparatide formulation is administrated in combination with one or more additional osteoporosis therapies, including for example alendronate therapy. In these embodiments, the additional osteoporosis therapy may be administered before, during, or after the treatment with abaloparatide.

In certain embodiments of the methods disclosed herein, said administration comprises application of a force to the transdermal patch sufficient to drive one or more of the microprojections through the stratum corneum of the patient. In certain embodiments of the methods disclosed herein, the site of administration is the abdomen or the thigh.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1: Pharmacokinetics of Abaloparatide Delivered via Transdermal Patch Prepared Using Preparation Formulations Comprising PEG or $ZnCl_2$ in Non-Human Primates Microneedle transdermal patches coated with various formulations of abaloparatide were provided ready for use and stored refrigerated at 2-8° C. At least one hour prior to use, the transdermal patches in individual pouches were placed at room temperature. For purposes of the examples presented below, the area of a single patch with microneedles on was typically about 1.26 cm². If two patches were used, they had a combined area of about 2.52 cm². The patch was typically applied by pushing the delivery device containing the patch to the skin with some force which helps to make the skin taut so that when the needles are delivered, reducing skin movement when the patch is delivered. A typical force might be between 15-25 newtons. Once the appropriate force was applied, the device was triggered and the patch pushed into the skin. The energy at impact to the patch upon delivery is generally delivered very quickly to the stratum corneum with a penetration time of less than, for example 50 milliseconds or even less than 10 milliseconds and an energy sufficient to cause one or more of the microprojections (ideally, most of them) to penetrate the stratum corneum by at least 50 micrometers, or more than 100 micrometers but generally less than 500 micrometers.

Eight female non-naïve Chinese Cynomolgus monkeys (2-4 kg at time of dosing) were included in the study. The same eight animals were used to test each formulation, with a three day washout period between tests. Each animal received a fixed dose of abaloparatide without correcting for body weight.

The skin was prepared 24 hours prior to each transdermal patch application. A small area (5×5 cm) of the dorsal flank was prepared by close clipping of the hair with a small animal clipper. Care was taken during the clipping procedure to avoid abrasion of the skin. Both sides of the dorsal flank (thigh) were prepared for each administration to ensure a side without skin irritation was used for dose administration. The skin was wiped with an alcohol swab 15 minutes prior to patch application. Extra care was taken to ensure the collar of the path was firmly attached to the applicator prior to application and that the transdermal patch was firmly seated on the leg for administration.

Body weights of the animals were recorded prior to Day 1. 1.5 mL of whole blood from a peripheral vessel was collected pre-dose on Day 1 into a $K_3$EDTA/aprotinin tube containing 15 µL (of 2.5 mg protein/mL/aprotinin solution) per ml of whole blood.

The transdermal patch was left in place for 15 minutes after placement. A line was drawn around the site of administration to enable post-dose observations. Each dose site was scored using the Draize scoring system pre-dose on Day 1 and at 1 hour and 24 hours post-dose. After patch removal, the transdermal patch was analyzed for residual content.

1.5 mL of whole blood from a peripheral vessel was collected at 5, 10, 20, 30, 60, and 90 minutes after patch application into a $K_3$EDTA/aprotinin tube containing 15 µL (of 2.5 mg protein/mL/aprotinin solution) per ml of whole blood. Whole blood samples were collected within ±5% of the scheduled collection time, with actual collection times recorded. Samples were kept on wet ice until processed. Animals were observed at each study blood collection time point. Any abnormalities were recorded by exception and reported immediately.

Whole blood samples were processed to plasma. Blood was centrifuged for 10±2 minutes in a refrigerated centrifuge. Plasma samples were transferred to two approximately equal aliquots (aliquot 1 and aliquot 2). Samples were frozen at −70° C.±10° C.

Figure 1B:
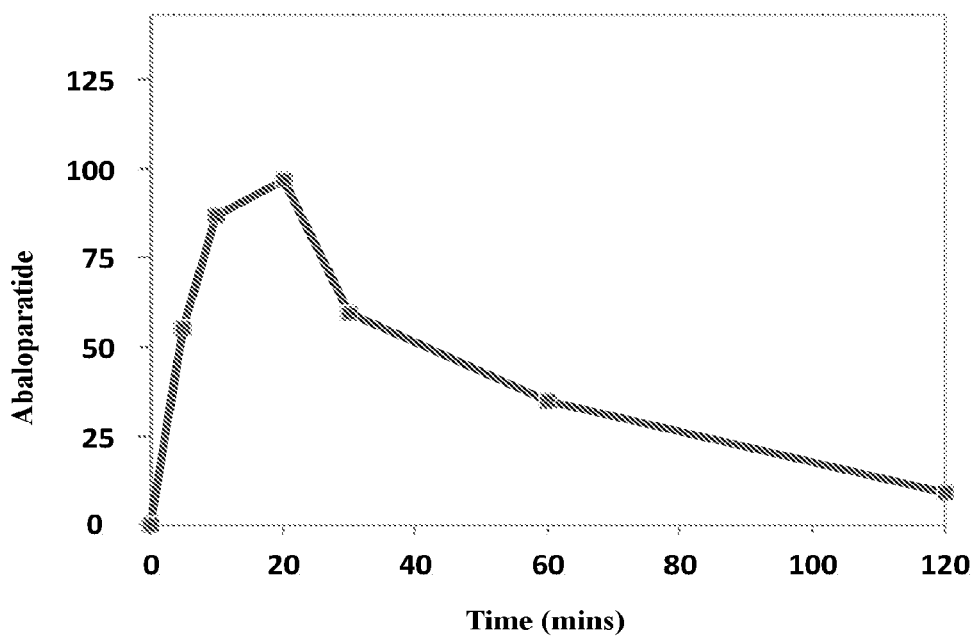

Abaloparatide concentrations were analyzed by LC-MS/MS. Abaloparatide serum concentrations were shown as percentage of the $C_{max}$ in FIGS. 1A-1B and FIG. 2.

The bioequivalence "window" for the abaloparatide-SC treatment was established by identifying the 80%-125% serum concentration of abaloparatide versus time following the abaloparatide-SC treatment (FIG. 1A). The abaloparatide-SC treatment was carried out by single subcutaneous administration of an aqueous formulation of abaloparatide (2 mg/mL) in an acetate buffer (5 mg/mL trihydrate sodium acetate, pH 5.1 adjusted with acetic acid) further comprising phenol (5 mg/mL) with a dose of 80 µg abaloparatide.

Application of a transdermal patch (hereinafter, the "TD-A32") prepared by coating a microneedle array with an abaloparatide coating formulation comprising about 0.89% w/w % $ZnCl_2$ and about 40% abaloparatide in water for injection (Preparation Formulation A32, FIG. 1B) resulted in a pharmacokinetic profile that overlapped significantly with the bioequivalence window of FIG. 1A. The patch ("patch-A32") is loaded with 79 µg of abaloparatide.

Figure 1C:
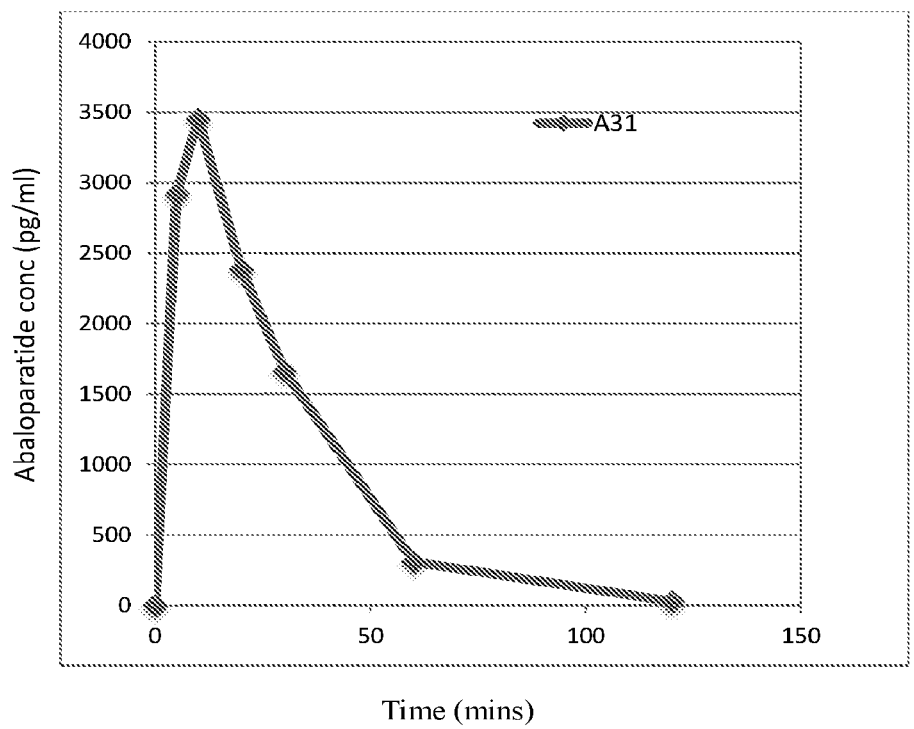

Application of a transdermal patch prepared by coating a microneedle array with an abaloparatide preparation formulation comprising about 14.5% PEG, and approximately 40% abaloparatide in water (Preparation Formulation A31, FIG. 1C) resulted in a pharmacokinetic profile hat overlapped significantly with the bioequivalence window of FIG. 1a. The patch is loaded with 125 µg of abaloparatide.

Furthermore, modeling using fix increments were carried out to the pharmacokinetic profile of TD-A32 obtained as described supra. The abaloparatide-SC treatment data and TD-A32 data with dose of 79 µg were obtained from the experiments described supra (Table 1). The TD-A32 data with doses of 118.5 µg, 146.95 µg, 158 µg, and 177.75 µg (Table 1) were obtained by modeling of the experimental data of TD-A32 with dose of 79 µg, with the following formulations:

$$\frac{C_{max} \text{ of TD-}A32 \text{ with dose of } A \text{ µg}}{C_{max} \text{ of TD-}A32 \text{ with dose of 79 µg}} = \frac{A}{79}$$

$$\frac{AUC \text{ of TD-}A32 \text{ with dose of } A \text{ µg}}{AUC \text{ of TD-}A32 \text{ with dose of 79 µg}} = \frac{A}{79}$$

The TD-A32 modeling data with $C_{max}$ 90% CI and AUC 90% CI both within the range of 80-125% were bioequivalent to the abaloparatide-SC treatment (e.g., Table 1, TD-A32 with a dose of about 177.75 µg). Thus, Table shows that adjusting dose of abaloparatide of the transdermal administration may adjust the PK profile to achieve bioequivalence or substantial bioequivalence of the abaloparatide-SC treatment.

Figure 2:
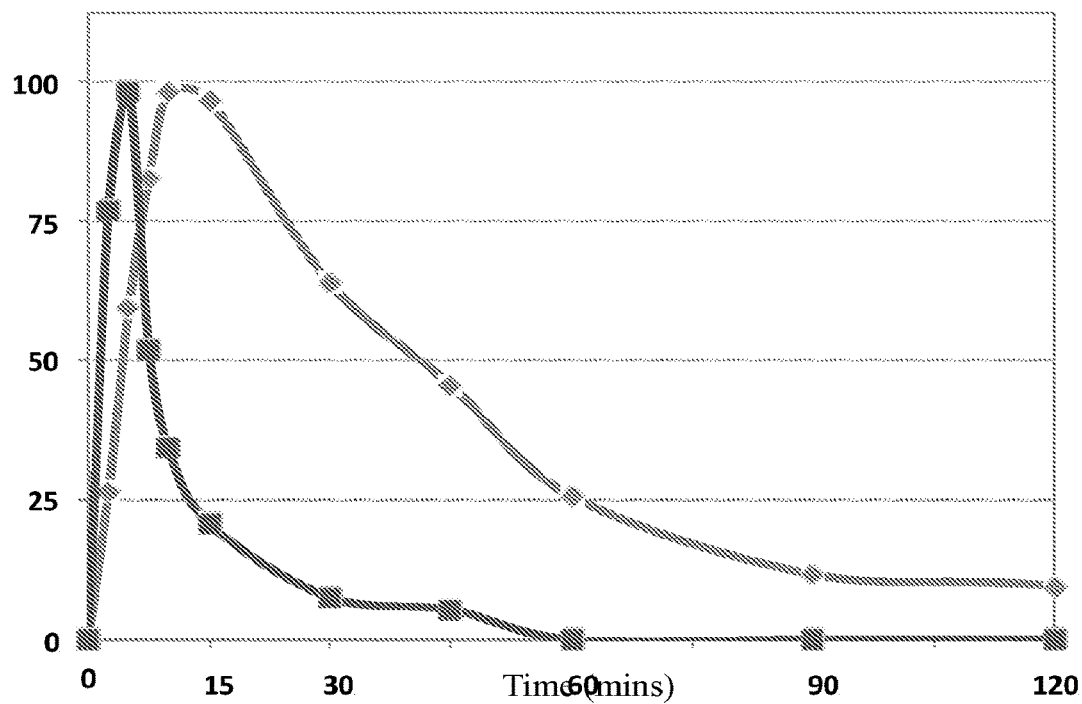
FIG. 2: Pharmacokinetic profile of formulations of abaloparatide administered by transdermal versus subcutaneous routes (SC). The abaloparatide preparation formulation of the abaloparatide for transdermal delivery did not comprise $ZnCl_2$ or PEG, (PBS buffer only) note the very quick $C_{max}$ of the transdermal delivery compare to SC and the increasing pulsatile nature of the delivery. Square: transdermal delivery (TD); and diamond: the abaloparatide-SC treatment. Administration in healthy postmenopausal women, % scale on vertical axis indicates the normalized plasma concentration of abaloparatide represented by % of $C_{max}$ for each group.

Example 2: Pharmacokinetics of Abaloparatide Delivered via Transdermal Patch Prepared Using Preparation Formulations with PBS Buffer in Human The pharmacokinetic profile of transdermal administration of abaloparatide and the abaloparatide-SC treatment was assessed in healthy postmenopausal women from 50 to 80 years of age, inclusive. Subjects received a single application of a transdermal patch (100 µg abaloparatide) prepared by coating with an abaloparatide formulation comprising 54% abaloparatide in 1× PBS buffer (FIG. 2, square), unless stated otherwise in this specification, PBS buffer refers to a ×1 PBS buffer concentration, or SC-injection of 80 µg of abaloparatide in an aqueous formulation comprising acetate buffer (5 mg/mL tri-hydrate sodium acetate, pH 5.1 adjusted with acetic acid), 5 mg/mL phenol, and 2 mg/mL abaloparatide (FIG. 2, diamond). Blood samples were collected at baseline and 5, 10, 15, 20, 30, 60, 90 and 120 minutes post dose. Abaloparatide concentrations were analyzed by LC-MS/MS method.

Transdermal delivery of abaloparatide using a transdermal patch prepared using an abaloparatide formulation without PEG or $ZnCl_2$ provided a much faster release of abaloparatide than the abaloparatide-SC treatment. Transdermal delivery using a transdermal patch prepared using an abaloparatide formulation with $ZnCl_2$ or PEG as an excipient as provided herein resulted in a PK profile that was much more similar to that of the abaloparatide-SC treatment.

Example 3 (Cohort 1 100 µg, 150 µg, 200 µg): Pharmacokinetics of Abaloparatide Delivered via Transdermal Patch Prepared Using Preparation Formulations Comprising $ZnCl_2$ The pharmacokinetic profile of transdermal administration of abaloparatide and the abaloparatide-SC treatment was assessed in healthy postmenopausal women.

Subjects received a single application of a transdermal patch (500×550 patch; needles had a length of 500 μm and needle tips were spaced 550 μm from each other) loaded with 100 μg, 150 μg, or 200 μg abaloparatide, or a SC-injection of 80 μg of abaloparatide.

Certain transdermal patches were prepared by coating with an abaloparatide formulation (Coating formulation A) comprising about 0.89% % $ZnCl_2$ w/w %, about 45% abaloparatide w/w %, remaining water for injection (Abaloparatide 100 μg TD, Abaloparatide 150 μg TD, and Abaloparatide 200 μg TD). Alternatively, the coating formulation is expressed as a molar ratio of excipient (eg $ZnCl_2$) to abaloparatide where, for example, a coating solution having about 0.89% w/w % had a molar ratio of about 0.7 $ZnCl_2$ to abaloparatide API (the molar ratio is expressed herein for convenience is 0.7M $ZnCl_2$). Coating with formulation A as used in the following examples resulted in patches with about 1.93% w/w of $ZnCl_2$ to formulation weight. Certain transdermal patches were loaded with 150 μg abaloparatide using a first general abaloparatide formulation comprising abaloparatide in PBS buffer with no additional excipients.

SC-injections of 80 μg of abaloparatide were administered by an injection pen (reusable is SC ref 1 and disposable is SC ref 2) of an aqueous formulation comprising acetate buffer (5 mg/mL tri-hydrate sodium acetate, pH 5.1 adjusted with acetic acid), 5 mg/mL phenol, and 2 mg/mL abaloparatide.

Blood samples were collected at baseline and various time points up to 4 hours post dose. Abaloparatide concentrations were analyzed by LC-MS/MS method. NCA (non-compartmental analyses) was performed using extravascular model. Relative actual times were used when possible, otherwise, relative nominal times were used. Nominal doses were used for the analysis. BQL were set to zero, and no subject or sample exclusions applied. Unless otherwise specified, in FIGS. 11 to 24, the box represent the 25th through 75th percentile of observations, the broken line represents the median of observations, the solid line represents the mean of observations, and the whiskers represents the extreme observations PK results are summarized in Table 2, FIG. 3 (longitude of median plasma abaloparatide concentration v. time post administration), FIG. 4 (median plasma abaloparatide concentration v. time post administration), FIG. 5 (longitude of mean plasma abaloparatide concentration v. time post administration), FIG. 6 (mean plasma abaloparatide concentration v. time post administration), FIG. 7 (longitude of median of dose normalized plasma abaloparatide concentration v. time post administration), FIG. 8 (median of dose normalized plasma abaloparatide concentration v. time post administration), FIG. 9 (longitude of mean of dose normalized plasma abaloparatide concentration v. time post administration), and FIG. 10 (mean of dose normalized plasma abaloparatide concentration v. time post administration), respectively.

PK results of treatment of Abaloparatide 100 μg TD, Abaloparatide 150 μg TD, Abaloparatide 200 μg TD, Abaloparatide 80 μg SC ref 1, and 150 μg TD (PBS buffer only) were compared to SC ref 2. (Table 3), and shown in FIGS. 11, 13, 15, 17, 19, 21, and 23 for $C_{max}$, $AUC_{last}$, $AUC_{inf}$, $C_{max}/D$ ($C_{max}$ per dosage), CL/F, HL_Lambda_z, and $T_{max}$, respectively.

PK results of treatment of Abaloparatide 100 μg TD, Abaloparatide 150 μg TD, Abaloparatide 200 μg TD, Abaloparatide 80 μg SC ref 1, and SC ref 2 were compared to 150 μg TD (PBS buffer) (Table 4). PK results of treatment of Abaloparatide 200 μg TD, and Abaloparatide 80 μg SC, compared to 150 μg TD (PBS buffer) are shown in FIGS. 12, 14, 16, 18, 20, 22, and 24 for $C_{max}$, $AUC_{last}$, $AUC_{inf}$, $C_{max}/D$ ($C_{max}$ per dosage), CL/F, HL_Lambda_z, and $T_{max}$, respectively. Abaloparatide 100 μg TD, Abaloparatide 150 μg TD, and Abaloparatide 200 μg TD treatments prepared from coating formulation A all significantly enhanced abaloparatide delivery (about twice of AUC), with lower $C_{max}$ (about 60% to about 70%), longer $t_{1/2}$ (about doubled), and longer time to $T_{max}$ compared to the TD PBS buffer-only formulation. The variability was similar between the two routes of administration (SC and TD), although the range (AUC maximum-minimum) appeared lower for the TD administration (FIG. 16). Comparison of the $C_{max}$ of the TD and SC delivery of Formulation A suggested a small incremental dose escalation may be needed to be more comparable (FIG. 12). FIG. 25 shows a PK profile of a subject treated with a transdermal patch prepared using Formulation A was within a comparable range of the SC ref 2. Some additional views of the data are shown in FIGS. 31 and 32. SC arm is SC ref 1, "TD First Generation" is abaloparatide in PBS buffer only and "TD Formulation" refers to formulation A.

Example 4: Phase 2 Study of Transdermal Patch Prepared Using Abaloparatide with PBS-Buffer Only Randomized, parallel-group, placebo-controlled, comparator-controlled, phase 2 study was carried out using transdermal patch prepared using a first generation abaloparatide formulation comprising abaloparatide and PBS. For 6 months, subjects received a daily TD application of a transdermal patch (with microprojections with length of 500 micrometer) loaded with 50 μg, 100 μg, or 150 μg abaloparatide (TD ABL 50 mcg, TD ABL 100 mcg, and TD ABL 150 mcg, respectively), a daily SC-injection of 80 μg of abaloparatide (SC ABL 80 mcg), or a placebo (TD Placebo) (Table 5).

Percent BMD changes from baseline of the subjects were determined at lumber spine (FIG. 26), and total hip (FIG. 27), respectively, N=231 total. Local tolerance data were summarized in FIG. 28 for % of subjects showing swelling or dermal response.

Summary of $C_{max}$, AUC and percent BMD change from baseline of the subjects treated with the abaloparatide transdermal patch (TD-50 mcg, TD-100 mcg and TD-150 mcg) and abaloparatide SC-injection (SC-80 mcg) were further summarized in Table 6.

Analysis of the PK/PD relationship ($C_{max}$ vs BMD and AUC vs BMD) revealed a dose dependence and a linear relationship with AUC, suggesting that AUC rather than $C_{max}$ was a key driver of efficacy (FIGS. 30A-30B). AUC of the subjects treated with the abaloparatide transdermal patch (green diamonds) and the subjects treated with abaloparatide SC-injection (orange diamond) showed a linear relationship versus percent BMD changes from baseline of the subjects (FIG. 30B), while $C_{max}$ of these subjects did not (FIG. 30A). Such data suggested AUC was a key driver of the efficacy of abaloparatide treatments.

As shown in FIG. 28, the TD patches were well tolerated. POC for TD delivery of abaloparatide was shown, but with lower BMD gain achieved compared to the SC delivery.

PK profile of the TD patch prepared using the first generation abaloparatide formulation showed more pulsatile delivery than SC delivery with comparable $C_{max}$ and lower AUC (about 25-30% of SC) (FIG. 29).

Example 5: Abaloparatide Formulation D Comprising Polyethylene Glycol for Use in Humans Formulation D was used to prepare coated patches with 100 μg, 150 μg and 200 μg abaloparatide patches wherein polyethylene glycol was an included excipient. Coating formulation D contained about 40% w/w abaloparatide, about 14% w/w PEG 3350NF and the rest sterile water for injection. The dried patch ready to use contained about 22%-30% PEG 3350 NF and the remainder abaloparatide. The patches prepared were administered to the abdomen and samples collected for pK measurements. The pK profiles of the PEG-coated patches for the three dose groups are shown in FIGS. 33-35.

The administration site was the abdomen, wear time was 15 minutes and the pK parameters are shown in FIGS. 33-35.

Example 6 Pharmacokinetics of Transdermal Formulations Containing PEG/ZnCl$_2$ Healthy postmenopausal volunteers were treated with an 80 μg sc injection as described previously or with a transdermal patch formulated to contain 100, 150 or 200 μg abaloparatide. The transdermal formulations were coated with PEG 3350 NF/ZnCl$_2$ with a coating solution (coating solution E) consisting of approximately 35% abaloparatide w/w, about 13%% w/w PEG3350NF, about 0.89% w/w ZnCl$_2$ and about 52% w/w water. The PEG/ZnCl$_2$ patch upon drying consisted essentially of 70-75%% abaloparatide and 24%-28%% PEG 33550 NF, and about 1.5% ZnCl$_2$. The administration site was the abdomen with wear time of 15 minutes and the pK parameters are shown in FIGS. 36-38.

Example 7-12

In a similar manner to that described in examples 5-6, additional variants were carried out as briefly described below in examples 7-12. Pharmacokinetic data for Examples 7-12 are shown in Tables 7-9.

Example 7 (4P1)

Microneedle patches made from coating formulation A as described and evaluated at a 200 ug abaloparatide dose and evaluated for its pharmacokinetic profile in healthy menopausal women. The administration site was the thigh.

Example 8 (4P3)

The same preparation formulation as example 8 (coating formulation A) was used together with 150 μg abaloparatide. Two coated patches were administered one immediately after the other (total of 300 μg abaloparatide) and both administrations were to a patient's abdomen.

Example 9 (5P1)

The microneedle patch was prepared from a preparation formulation containing about 2.2 M (mole ration ZnCl$_2$ to abaloparatide in coating solution Coating formulation B) ZnCl$_2$ concentration (about 2.2% w/w) and about 36% w/w abaloparatide (remaining weight from water for injection) resulting in a dried patch containing an abaloparatide formulation of about 5.83% w/w ZnCl$_2$, about 94.16% w/w abaloparatide (not including any residual water fraction), the weight of abaloparatide peptide was 200 μg. The administration site was the thigh.

Example 10 (5P2)

Patch was prepared using a 0.7M Zn(OAc)$_2$ coating solution C (1.38 w/w Zn(OAc)$_2$) producing a patch ready to use with about 97% w/w abaloparatide and about 3.3% w/w Zn(OAc)$_2$ with a total of about 200 μg abaloparatide on the patch. The administration site was the thigh.

Example 11 (5P3)

The microneedle patch was prepared from the same preparation formulation as Example 7 except it contained 260 μg abaloparatide and was applied to the thigh with a wear time of 15 minutes.

Example 12 (5P4)

Patches were circular and prepared according to the description in Example 9 with the same dose. This was a 2×200 μg patch study with both patches being delivered to the thigh, one immediately after the other. Since two patches were employed, the equivalent area employed as a single patch is approximately 2.52 cm$^2$ and the equivalent single patch diameter of approximately 2.52 cm (1.26 cm each). The pharmacokinetic curve of the patch administered abaloparatide from example 13 is overlayed with a reference data set with abaloparatide 80 μg SC.

Example 13: Blood Sample Collection from Female Non-Human Primates Following Administration of the Abaloparatide via Transdermal Patch Microneedle transdermal patches coated with various formulations of abaloparatide were provided ready for use and stored refrigerated at 2-8° C. At least one hour prior to use, the transdermal patches in individual pouches were placed at room temperature. Eight female non-naïve Chinese Cynomolgus monkeys (2-4 kg at time of dosing) were included in the study. The same eight animals were used to test each formulation, with a three day washout period between tests.

Time points were calculated from the time of patch application at 5 minutes, 10 minutes, 20 minutes, 30 minutes, 1 hour, and 1.5 hours post-dose. A time point of pre-dose was taken at Day 1. 1.5 mL of whole blood was collected at each time point. K$_3$EDTA/aprotinin was used as an anti-coagulant.

Each animal received a fixed dose of abaloparatide without correcting for body weight. The dose administration was performed as follows:

Day 1: Test material was delivered by application of a transdermal patch. The skin was prepared 24 hours prior to each transdermal patch application as follows: a small area (5×5 cm) of the dorsal flank was prepared by close clipping of the hair with a small animal clipper. Care was taken during the clipping procedure to avoid abrasion of the skin. Both sides of the dorsal flank (thigh) were prepared for each administration to ensure a side without skin irritation was used for dose administration. Fifteen (15) minutes prior to patch application the skin was wiped with an alcohol swab. Extra care was taken to ensure the collar of the path was firmly attached to the applicator prior to application and that the transdermal patch was firmly seated on the leg for administration.

Days 4, 7, and 10: Test material was delivered by application of a transdermal patch. The skin was prepared 24 hours prior to each transdermal patch application as described above. Extra care was taken to ensure the collar of the path is firmly attached to the applicator prior to application and that the transdermal patch was firmly seated on the leg for administration.

Days 1, 4, 7, and 10: The transdermal patch was left in place for 15 minutes after placement. A line was drawn around the site of administration to enable post dose observations. After patch removal, the transdermal patch was analyzed for residual content.

Animals were observed at each study blood collection time point. Any abnormalities were recorded by exception and reported immediately. Each dose site at pre-dose, 1 hour and 24 hours post-dose was scored using the Draize scoring system. Body weights of the animals were recorded prior to Day 1.

coated with various coating formulations disclosed herein in comparison to those of Abaloparatide administered subcutaneously.

FIG. 41 show the PK profile of subcutaneous (SC) delivery of abaloparatide (ABL), and transdermal delivery (TD) of abaloparatide (ABL) using patches prepared by various transdermal formulations for coating. Filled diamond: ABL administered SC; unfilled triangle: an ABL formulation without excipient administered TD; filled circle: an ABL formulation comprising a PVP administered TD; filled square: an ABL formulation comprising a PLGA administered TD; filled triangle: an ABL formulations comprising a PLGA administered TD; X: an ABL formulations comprising a HPβCD administered TD; star: an ABL formulations comprising a PLGA administered TD; unfilled circle: an ABL formulations comprising a PEG administered TD; +: an ABL formulations comprising a HPβCD administered TD; unfilled square: an ABL formulations comprising $ZnCl_2$ administered TD. ABL plasma concentration at various time after each administration is summarized in the following table

| Administration Route | SC | TD | TD | TD | TD | TD | TD | TD | TD | TD |
|---|---|---|---|---|---|---|---|---|---|---|
| Formulation | ABL only | ABL + PVPC17 | ABL + PLGA | ABL + PLGA | ABL + HPbCD* | ABL + PLGA | ABL + PEG3350 | ABL + HPbCD* | ABL + $ZnCl_2$ |
| % formulation or concentration | | | | | | | 15% | 4.90% | 2.60% |
| Dose/patch, mcg | 145 | 120 | 96 | 88 | 113 | 253 | 188 | 84 | 119.00 |
| Time (min) | Average ABL plasma concentration (pg/mL) | | | | | | | | | |
| 0 | 0 | 0 | 0 | 0 | 0 | 0 | 4 | 0 | 0 | 0 |
| 5 | 1900 | 3903 | 1432 | 2605 | 2309 | 17283 | 7731 | 16690 | 5591 | 4448 |
| 10 | 880 | 2422 | 1608 | 1959 | 2385 | 18503 | 7651 | 16799 | 6496 | 10651 |
| 20 | 542 | 1789 | 1953 | 2250 | 2648 | 19764 | 7290 | 13830 | 6260 | 18404 |
| 30 | 222 | 698 | 893 | 1287 | 2675 | 20134 | 6390 | 12469 | 5391 | 20460 |
| 60 | 120 | 186 | 538 | 465 | 2539 | 15212 | 4634 | 8846 | 5082 | 17271 |
| 90 | 224 | 68 | 108 | 335 | 1927 | 13082 | 5042 | 7564 | 4913 | 14879 |
| Cmax | 3341 | 3800 | 2758 | 3237 | 3439 | 22261 | 8757 | 17640 | 7096 | 22090 |
| Tmax | 7 | 9 | 20 | 9 | 14 | 17 | 13 | 8 | 25 | 26 |
| T½ | 14 | 15 | 19 | 22 | 57 | 142 | 54 | 63 | 94 | 148 |
| AUC | 131610 | 74391 | 74371 | 94925 | 204233 | 1433788 | 474246 | 975961 | 444580 | 1436678 |

*HPbCD is a HPβCD.

All blood samples were collected from a peripheral vessel. At Day 1, 1.5 mL of whole blood was collected pre-dose into a $K_3$EDTA/aprotinin tube containing 15 μL (of 2.5 mg protein/mL/aprotinin solution) per ml of whole blood. At Days 1, 4, 7, and 10, 1.5 mL of whole blood was collected at each time point (5 minutes, 10 minutes, 20 minutes, 30 minutes, 60 minutes and 90 minutes after patch application) into a $K_3$EDTA/aprotinin tube containing 15 μL (of 2.5 mg protein/mL/aprotinin solution) per ml of whole blood. Whole blood samples were collected within ±5% of the scheduled collection time, with actual collection times recorded. Samples were kept on wet ice until processed.

The whole blood samples were processed to plasma. Blood was centrifuged for 10±2 minutes in a refrigerated centrifuge. Plasma samples were transferred to two approximately equal aliquots (aliquot 1 and aliquot 2). Samples were frozen at −70° C.±10° C.

B): Pharmacokinetics of Various Abaloparatide Formulations Delivered via Transdermal Patch FIGS. 39 and 40 show Cmax and AUC of delivery of Abaloparatide upon administration by transdermal patches The foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references in the present disclosure are hereby incorporated by reference herein in their entireties.

REFERENCES

References listed below are herein incorporated by reference.

1. Augustine et al., "Parathyroid hormone and parathyroid hormone-related protein analogs as therapies for osteoporosis," Curr Osteoporos Rep 11:400-406 (2013).
2. Bostrom et al., "Parathyroid hormone-related protein analog RS-66271 is an effective therapy for impaired bone healing in rabbits on corticosteroid therapy," Bone 26:437-442 (2000).

3. Dean et al., "Altered selectivity of parathyroid hormone (PTH) and PTH-related protein (PTHrP) for distinct conformations of the PTH/PTHrP receptor," Mol Endocrinol 22:156-166 (2008).
4. Dempster et al., "Skeletal histomorphometry in subjects on teriparatide or zoledronic acid therapy (SHOTZ) study: a randomized controlled trial," J Clin Endocrinol Metab 97:2799-2808 (2012).
5. Dhainaut et al., "Cortical hand bone porosity and its association with distal radius fracture in middle aged and elderly women," PLoS One 8:e68405 (2013).
6. Doyle et al., "BA058, a novel human PTHrP analog: reverses ovariectomy-induced bone loss and strength at the lumbar spine in aged cynomolgus monkeys," J Bone Miner Res 28 (Suppl 1) (2013a).
7. Doyle et al., "Long term effect of BA058, a hovel human PTHrP analog, restores bone mass in the aged osteopenic ovariectomized cynomolgus monkey," J Bone Miner Res 28 (Suppl 1) (2013a).
8. Hattersley G, Lesage E, Varela A, Mith S Y. BA058, a Novel Human PTHrP Analog, Restores Bone Density and Increases Bone Strength At the Spine and Femur in Osteopenic Rats. Endocr Rev. 2013; 34(abstract).
9. Horwitz et al., "Safety and tolerability of subcutaneous PTHrP(1-36) in healthy human volunteers: a dose escalation study," Osteoporos Int 17:225-230 (2006).
10. Horwitz et al., "Parathyroid hormone-related protein for the treatment of postmenopausal osteoporosis: defining the maximal tolerable dose," J Clin Endocrinol Metab 95:1279-1287 (2010).
11. Kronenberg, "PTHrP and skeletal development," Ann N Y Acad Sci 1068:1-13 (2006).
12. Leder et al., "Two years of Denosumab and teriparatide administration in postmenopausal women with osteoporosis (The DATA Extension Study): a randomized controlled trial," J Clin Endocrinol Metab 99:1694-1700 (2014).
13. Ma et al., "Comparative effects of teriparatide and strontium ranelate in the periosteum of iliac crest biopsies in postmenopausal women with osteoporosis," Bone 48:972-978 (2011).
14. MacLean et al., "Systematic review: comparative effectiveness of treatments to prevent fractures in men and women with low bone density or osteoporosis," Ann Intern Med 148:197-213 (2008).
15. Neer et al., "Effect of parathyroid hormone (1-34) on fractures and bone mineral density in postmenopausal women with osteoporosis," N Engl J Med 344:1434-1441 (2001)
16. Obaidi et al., "Pharmacokinetics and Pharmacokinetics and pharmacodynamic of subcutaneously (SC) administered doses of BA058, a bone mass density restoring agent in healthy postmenopausal women," AAPS Abstract W5385 (2010)
17. Oei et al., "High bone mineral density and fracture risk in type 2 diabetes as skeletal complications of inadequate glucose control: the Rotterdam Study," Diabetes Care 36:1619-1628 (2013).
18. Okazaki et al., "Prolonged signaling at the parathyroid hormone receptor by peptide ligands targeted to a specific receptor conformation," Proc Natl Acad Sci USA 105: 16525-16530 (2008).
19. Pioszak et al., "Structural basis for parathyroid hormone-related protein binding to the parathyroid hormone receptor and design of conformation-selective peptides," J Biol Chem 284:28382-28391 (2009).
20. Recker et al., "Comparative effects of teriparatide and strontium ranelate on bone biopsies and biochemical markers of bone turnover in postmenopausal women with osteoporosis," J Bone Miner Res 24:1358-1368 (2009).

TABLE 1

Modeling of TD-A32 data for bioequivalence for the abaloparatide-SC treatment (SC)

|  | SC | TD-A32 | SC | TD-A32 | SC | TD-A32 | SC | TD-A32 | SC | TD-A32 |
|---|---|---|---|---|---|---|---|---|---|---|
| Dose (µg) |  | 79 |  | 118.5 |  | 146.95 |  | 158 |  | 177.75 |
| n | 34 | 16 | 34 | 34 | 34 | 34 | 34 | 34 | 34 | 34 |
| $C_{max}$ (pg/mL) | 6342 | 3381 | 6342 | 5072 | 6342 | 6289 | 6342 | 6763 | 6342 | 7608 |
| $C_{max}$ SD | 3171 | 1690.5 | 3171 | 2536.0 | 3171 | 3144.5 | 3171 | 3381.5 | 3171 | 3804.0 |
| $C_{max}$ SC/TD-A32 |  | 1.876 |  | 1.250 |  | 1.008 |  | 0.938 |  | 0.834 |
| $C_{max}$ 90% CI | 145% | 259% | 107% | 147% | 86% | 118% | 80% | 110% | 71% | 98% |
| AUC | 375862 | 172271 | 375862 | 258407 | 375862 | 320425 | 375862 | 344542 | 375862 | 387611 |
| AUC SD | 187931 | 86135.5 | 187931 | 129203.5 | 187931 | 160212.5 | 187931 | 172271 | 187931 | 193805.5 |
| AUC SC/TD-A32 |  | 2.182 |  | 1.455 |  | 1.173 |  | 1.091 |  | 0.970 |
| AUC 90% CI | 164% | 318% | 123% | 173% | 100% | 138% | 93% | 128% | 83% | 113% |

TABLE 2

Abaloparatide (from coating formulation A) 100 μg TD, Abaloparatide 150 μg TD, Abaloparatide 200 μg TD; Abaloparatide 80 μg SC (Ref1), 150 μg TD (PBS buffer only) - site of administration is abdomen

| TRT | | T½ (h) | Tlag (h) | Tmax (h) | Cmax (pg/mL) | Cmax/D (pg/mL/ug) | AUClast (h*pg/mL) | AUCINF (h*pg/mL) | Vz/F (L) | CL/F (L/h) |
|---|---|---|---|---|---|---|---|---|---|---|
| ABALOPARATIDE | N | 9 | 9 | 9 | 9 | 9 | 9 | 9 | 9 | 9 |
| 80 ug SC | Mean | 0.92 | 0.00926 | 0.526 | 566 | 7.07 | 793 | 919 | 131 | 102 |
| | Min | 0.657 | 0 | 0.167 | 300 | 3.75 | 421 | 464 | 77.3 | 51.7 |
| | Median | 0.875 | 0 | 0.5 | 608 | 7.6 | 654 | 791 | 132 | 101 |
| | Max | 1.25 | 0.0833 | 1 | 768 | 9.6 | 1304 | 1549 | 207 | 172 |
| | CV % | 19.7 | 300 | 56 | 28.6 | 28.6 | 39.2 | 42.1 | 37 | 40.5 |
| | Geo Mean | 0.905 | | 0.457 | 542 | 6.78 | 741 | 849 | 123 | 94.2 |
| | CV % GeoMean | 19.9 | | 62 | 33 | 33 | 40.7 | 44.1 | 39.8 | 44.1 |
| ABALOPARATIDE | N | 4 | 8 | 8 | 8 | 8 | 8 | 4 | 4 | 4 |
| 100 ug TD | Mean | 1.34 | 0.0104 | 0.252 | 354 | 3.54 | 414 | 545 | 380 | 195 |
| | Min | 0.913 | 0 | 0.167 | 148 | 1.48 | 150 | 399 | 221 | 135 |
| | Median | 1.45 | 0 | 0.167 | 364 | 3.64 | 406 | 519 | 371 | 197 |
| | Max | 1.54 | 0.0833 | 0.5 | 554 | 5.54 | 736 | 743 | 556 | 250 |
| | CV % | 21.8 | 283 | 50.7 | 35.9 | 35.9 | 49.4 | 28.8 | 39.7 | 27.3 |
| | Geo Mean | 1.31 | | 0.229 | 330 | 3.3 | 363 | 529 | 357 | 189 |
| | CV % GeoMean | 24.9 | | 47.7 | 44.4 | 44.4 | 64.1 | 29 | 43.3 | 29 |
| ABALOPARATIDE | N | 7 | 8 | 8 | 8 | 8 | 8 | 7 | 7 | 7 |
| 150 ug TD | Mean | 1.29 | 0 | 0.292 | 387 | 2.58 | 487 | 445 | 694 | 370 |
| | Min | 1.09 | 0 | 0.167 | 202 | 1.35 | 235 | 280 | 345 | 219 |
| | Median | 1.3 | 0 | 0.333 | 427 | 2.85 | 389 | 412 | 626 | 364 |
| | Max | 1.57 | 0 | 0.5 | 530 | 3.53 | 1250 | 683 | 1030 | 535 |
| | CV % | 14.9 | | 40.4 | 30.1 | 30.1 | 68.2 | 33.3 | 36.3 | 31.6 |
| | Geo Mean | 1.28 | | 0.27 | 368 | 2.45 | 420 | 424 | 653 | 353 |
| | CV % GeoMean | 15 | | 44.3 | 36.5 | 36.5 | 58.4 | 33.8 | 39.7 | 33.8 |
| ABALOPARATIDE | N | 8 | 9 | 9 | 9 | 9 | 9 | 8 | 8 | 8 |
| 200 ug TD | Mean | 1.26 | 0 | 0.281 | 435 | 2.17 | 494 | 635 | 676 | 373 |
| 150 μg TD PBS | Min | 0.904 | 0 | 0.167 | 234 | 1.17 | 160 | 271 | 272 | 191 |
| | Median | 1.17 | 0 | 0.2 | 394 | 1.97 | 459 | 611 | 702 | 327 |
| | Max | 1.94 | 0 | 0.5 | 752 | 3.76 | 914 | 1045 | 1280 | 737 |
| | CV % | 25.9 | | 50.3 | 41 | 41 | 50.5 | 40.8 | 49 | 47.9 |
| | Geo Mean | 1.22 | | 0.253 | 405 | 2.02 | 434 | 586 | 602 | 341 |
| | CV % GeoMean | 24.2 | | 50.7 | 41.5 | 41.5 | 61.1 | 46.8 | 57.1 | 46.8 |
| Historical | N | 12 | 12 | 12 | 12 | 12 | 12 | 12 | 12 | 12 |
| 80 ug TD | Mean | 0.676 | 0 | 0.135 | 536 | 3.57 | 225 | 262 | 549 | 698 |
| | Min | 0.185 | 0 | 0.0833 | 238 | 1.59 | 62.8 | 75.3 | 251 | 389 |
| | Median | 0.61 | 0 | 0.125 | 504 | 3.36 | 236 | 293 | 534 | 512 |
| | Max | 1.81 | 0 | 0.208 | 860 | 5.73 | 368 | 386 | 1090 | 1990 |
| | CV % | 63.2 | | 35 | 31.8 | 31.8 | 35.8 | 35.4 | 39.9 | 63 |
| | Geo Mean | 0.572 | | 0.128 | 509 | 3.39 | 208 | 242 | 513 | 621 |
| | CV % GeoMean | 67 | | 37.1 | 35.4 | 35.4 | 48.2 | 48.4 | 40.1 | 48.4 |

TABLE 3

Comparison of Abaloparatide (coating formulation A) 100 μg TD; Abaloparatide 150 μg TD; Abaloparatide 200 μg TD; Abaloparatide 80 μg SC (Ref1); and 150 μg TD (PBS buffer only); all to SC Ref2. - Site of administration is abdomen

| Test | Dependent | GeoMean Ref | GeoMean Test | % Ratio | 90% CI | |
|---|---|---|---|---|---|---|
| ABALOPARATIDE | AUCinf | 913 | 849 | 92.9 | 71 | 122 |
| 80 ug SC | AUClast | 861 | 741 | 86.1 | 63.3 | 117 |
| | CL/F | 87.6 | 94.2 | 108 | 82.1 | 141 |
| | Cmax | 602 | 542 | 90 | 72.1 | 112 |
| | Cmax/D | 7.53 | 6.78 | 90 | 72.1 | 112 |
| | T½ | 1.01 | 0.905 | 89.9 | 71.1 | 114 |
| ABALOPARATIDE | AUCinf | 913 | 529 | 57.9 | 39.7 | 84.4 |
| 100 ug TD | AUClast | 861 | 363 | 42.1 | 30.5 | 58.1 |
| | CL/F | 87.6 | 189 | 216 | 148 | 315 |
| | Cmax | 602 | 330 | 54.8 | 43.5 | 69.1 |
| | Cmax/D | 7.53 | 3.3 | 43.8 | 34.8 | 55.3 |
| | T½ | 1.01 | 1.31 | 130 | 93.7 | 181 |
| ABALOPARATIDE | AUCinf | 913 | 424 | 46.5 | 34.5 | 62.6 |
| 150 ug TD | AUClast | 861 | 420 | 48.7 | 35.3 | 67.2 |
| | CL/F | 87.6 | 353 | 404 | 300 | 544 |
| | Cmax | 602 | 368 | 61.1 | 48.5 | 77.1 |
| | Cmax/D | 7.53 | 2.45 | 32.6 | 25.8 | 41.1 |
| | T½ | 1.01 | 1.28 | 127 | 98.3 | 165 |
| A150 μg TD PBS 00 | AUCinf | 913 | 586 | 64.2 | 48.4 | 85.1 |
| buffer | AUClast | 861 | 434 | 50.4 | 37.1 | 68.6 |
| | CL/F | 87.6 | 341 | 390 | 294 | 517 |

TABLE 3-continued

Comparison of Abaloparatide (coating formulation A) 100 μg TD; Abaloparatide 150 μg TD; Abaloparatide 200 μg TD; Abaloparatide 80 μg SC (Ref1); and 150 μg TD (PBS buffer only); all to SC Ref2. - Site of administration is abdomen

| Test | Dependent | GeoMean Ref | GeoMean Test | % Ratio | 90% CI | |
|---|---|---|---|---|---|---|
| Historical 80 ug TD | Cmax | 602 | 405 | 67.2 | 53.8 | 83.9 |
| | Cmax/D | 7.53 | 2.02 | 26.9 | 21.5 | 33.6 |
| | T½ | 1.01 | 1.22 | 122 | 95.1 | 156 |
| | AUCinf | 913 | 242 | 26.5 | 20.8 | 33.7 |
| | AUClast | 861 | 208 | 24.1 | 18.3 | 31.8 |
| | CL/F | 87.6 | 621 | 709 | 556 | 904 |
| | Cmax | 602 | 509 | 84.6 | 69.3 | 103 |
| | Cmax/D | 7.53 | 3.39 | 45.1 | 36.9 | 55.1 |
| | T½ | 1.01 | 0.572 | 56.9 | 46.1 | 70.4 |

TABLE 4

Comparisons of Abaloparatide (coating formulation A) 100 μg TD, Abaloparatide 150 μg TD, Abaloparatide 200 μg TD, Abaloparatide 80 μg SC to 150 μg TD (PBS only), Site of administration is abdomen

| Test | Dependent | GeoMean Ref | GeoMean Test | % Ratio | 90% CI | |
|---|---|---|---|---|---|---|
| ABALOPARATIDE 80 ug SC | AUCinf | 242 | 849 | 351 | 257 | 479 |
| | AUClast | 208 | 741 | 357 | 251 | 508 |
| | CL/F | 621 | 94.2 | 15.2 | 11.1 | 20.7 |
| | Cmax | 509 | 542 | 106 | 82.5 | 137 |
| | Cmax/D | 3.39 | 6.78 | 200 | 155 | 258 |
| | T½ | 0.572 | 0.905 | 158 | 121 | 207 |
| ABALOPARATIDE 100 ug TD | AUCinf | 242 | 529 | 219 | 146 | 329 |
| | AUClast | 208 | 363 | 175 | 121 | 252 |
| | CL/F | 621 | 189 | 30.5 | 20.3 | 45.8 |
| | Cmax | 509 | 330 | 64.8 | 49.8 | 84.4 |
| | Cmax/D | 3.39 | 3.3 | 97.2 | 74.5 | 127 |
| | T½ | 0.572 | 1.31 | 229 | 160 | 326 |
| ABALOPARATIDE 150 ug TD | AUCinf | 242 | 424 | 176 | 126 | 245 |
| | AUClast | 208 | 420 | 202 | 140 | 292 |
| | CL/F | 621 | 353 | 57 | 40.7 | 79.6 |
| | Cmax | 509 | 368 | 72.3 | 55.5 | 94.1 |
| | Cmax/D | 3.39 | 2.45 | 72.3 | 55.5 | 94.1 |
| | T½ | 0.572 | 1.28 | 224 | 167 | 300 |
| ABALOPARATIDE 200 ug TD | AUCinf | 242 | 586 | 242 | 176 | 334 |
| | AUClast | 208 | 434 | 209 | 147 | 298 |
| | CL/F | 621 | 341 | 55 | 39.9 | 75.9 |
| | Cmax | 509 | 405 | 79.5 | 61.6 | 103 |
| | Cmax/D | 3.39 | 2.02 | 59.6 | 46.2 | 76.9 |
| | T½ | 0.572 | 1.22 | 214 | 161 | 283 |

TABLE 5

Design for a Phase 2 study of transdermal delivery of abaloparatide using a transdermal patch (PBS buffer only) abaloparatide formulation

| Treatment | Daily Dose | Number of Patients |
|---|---|---|
| ABL-TD | 50 μg | 50 |
| ABL-TD | 100 μg | 50 |
| ABL-TD | 150 μg | 50 |
| ABL-SC | 80 μg | 50 |
| Placebo | — | 50 |
| Total | | 250 |

TABLE 6

$C_{max}$, AUC, and BMD improvement of a Phase 2 study of transdermal delivery of abaloparatide using a transdermal patch (PBS buffer only) abaloparatide formulation

| Administration method - Dose | $C_{max}$ (pg/mL) | AUC (pg/ml · hr) | BMD Lumbar spine at 6 month (% change from baseline (n = 231)) |
|---|---|---|---|
| TD-50 mcg | 275 | 75 | 1.87 |
| TD-100 mcg | 468 | 130 | 2.33 |
| TD-150 mcg | 656 | 215 | 2.95 |
| SC-80 mcg | 592 | 820 | 5.8 |

TABLE 7

Pharmacokinetic parameters from Examples 8-13 compared to a reference group of 80 μg sc abaloparatide treated women. Geometric LS-means and ratios of TD and sc.

| Cohort/Period | Parameters | Units | SC LSM | TD Test Form/Dose | TD LSM | % Ratio | 90% CI | | 95% CI | |
|---|---|---|---|---|---|---|---|---|---|---|
| Example 8 | Cmax | pg/mL | 574 | A | 503 | 87.7 | 76.7 | 100.3 | 74.7 | 103.0 |
| | AUClast | h*pg/mL | 774 | 200 μg | 516 | 66.7 | 55.8 | 79.7 | 53.9 | 82.5 |
| | AUCinf | h*pg/mL | 850 | | 632 | 74.4 | 61.5 | 90.1 | 59.2 | 93.5 |
| Example 9 | Cmax | pg/mL | 574 | A | 707 | 123.2 | 103.1 | 147.4 | 99.5 | 152.6 |
| | AUClast | h*pg/mL | 774 | 300 μg | 686 | 88.6 | 69.8 | 112.7 | 66.5 | 118.1 |
| | AUCinf | h*pg/mL | 850 | (2 × 150) | 798 | 93.8 | 73.1 | 120.5 | 69.6 | 126.6 |
| Example 10 | Cmax | pg/mL | 574 | B | 358 | 62.5 | 53.8 | 72.6 | 52.2 | 74.8 |
| | AUClast | h*pg/mL | 774 | 200 μg | 490 | 63.3 | 51.8 | 77.3 | 49.8 | 80.4 |
| | AUCinf | h*pg/mL | 850 | | 645 | 75.9 | 61.3 | 94.1 | 58.7 | 98.2 |
| Example 11 | Cmax | pg/mL | 574 | C | 504 | 87.9 | 74.9 | 103.1 | 72.6 | 106.4 |
| | AUClast | h*pg/mL | 774 | 200 μg | 386 | 49.8 | 40.3 | 61.6 | 38.7 | 64.2 |
| | AUCinf | h*pg/mL | 850 | | 444 | 52.2 | 41.9 | 65.2 | 40.1 | 68.1 |
| Example 12 | Cmax | pg/mL | 574 | A | 545 | 95.0 | 81.6 | 110.7 | 79.2 | 114.0 |
| | AUClast | h*pg/mL | 774 | 260 μg | 426 | 55.0 | 44.7 | 67.6 | 43.0 | 70.4 |
| | AUCinf | h*pg/mL | 850 | | 499 | 58.7 | 47.0 | 73.3 | 45.0 | 76.6 |
| Example 13 | Cmax | pg/mL | 574 | B | 658 | 114.7 | 98.1 | 134.1 | 95.1 | 138.3 |
| | AUClast | h*pg/mL | 774 | 400 μg | 913 | 117.9 | 95.7 | 145.3 | 91.8 | 151.4 |
| | AUCinf | h*pg/mL | 850 | (2 × 200) | 1292 | 152.0 | 119.4 | 193.5 | 113.9 | 202.9 |

TABLE 8

Pharmacokinetic parameters from individuals from Examples 12.

| Subject | $T_{1/2}$ (h) | Tmax (h) | Cmax (pg/mL) | AUClast (h*pg/mL) | AUCINF (h*pg/mL) | Vz/F (L) | CL/F (mL/h) |
|---|---|---|---|---|---|---|---|
| 5001 | 0.80 | 0.17 | 430 | 267 | 297 | 862 | 748849 |
| 5002 | NC | 0.17 | 548 | 334 | NC | NC | NC |
| 5003 | 1.59 | 0.17 | 604 | 493 | 589 | 369 | 161152 |
| 5004 | 1.39 | 0.17 | 646 | 553 | 637 | 364 | 182030 |
| 5005 | 0.54 | 0.17 | 562 | 423 | 454 | 235 | 304561 |
| 5006 | 1.34 | 0.08 | 872 | 1156 | 1469 | 254 | 131356 |
| 5007 | 1.24 | 0.33 | 450 | 397 | 458 | 718 | 402388 |
| 5008 | 2.07 | 0.35 | 536 | 460 | 579 | 1166 | 390748 |
| 5009 | 1.55 | 0.33 | 418 | 279 | 382 | 1123 | 502928 |
| 5010 | 0.76 | 0.17 | 766 | 691 | 730 | 156 | 142960 |
| 5011 | 0.74 | 0.17 | 582 | 333 | 361 | 451 | 420388 |
| 5012 | 0.26 | 0.08 | 420 | 154 | 166 | 311 | 825569 |
| 5013 | 1.15 | 0.17 | 536 | 495 | 555 | 542 | 325925 |
| 5015 | 1.21 | 0.33 | 200 | 258 | 314 | 1003 | 572745 |
| 5016 | 0.96 | 0.17 | 1040 | 892 | 992 | 303 | 218817 |
| 5017 | 0.78 | 0.18 | 638 | 477 | 522 | 435 | 386718 |

NC = Not Calculated

TABLE 9

Pharmacokinetic parameters from individuals from Examples 13.

| Subject | $T_{1/2}$ (h) | Tmax (h) | Cmax (pg/mL) | AUClast (h*pg/mL) | AUCINF (h*pg/mL) | Vz/F (L) | CL/F (mL/h) |
|---|---|---|---|---|---|---|---|
| 5001 | NC | 0.33 | 578 | 532 | NC | NC | NC |
| 5002 | 1.61 | 0.33 | 554 | 719 | 919 | 854 | 367733 |
| 5003 | 1.54 | 0.50 | 612 | 1189 | 1687 | 245 | 110167 |
| 5005 | 1.37 | 0.33 | 712 | 837 | 1039 | 500 | 252504 |
| 5006 | 1.75 | 0.33 | 1518 | 2333 | 3378 | 197 | 78062 |
| 5007 | 1.56 | 0.33 | 576 | 967 | 1337 | 298 | 131921 |
| 5008 | 2.06 | 0.33 | 676 | 905 | 1340 | 375 | 126060 |
| 5009 | 1.15 | 0.33 | 456 | 582 | 699 | 421 | 253166 |
| 5010 | 1.82 | 0.33 | 1022 | 1393 | 2040 | 241 | 91472 |
| 5011 | 0.94 | 0.33 | 700 | 745 | 862 | 298 | 219611 |
| 5012 | 1.00 | 0.20 | 328 | 372 | 424 | 878 | 608262 |
| 5013 | 2.11 | 0.50 | 992 | 1650 | 2641 | 239 | 78603 |
| 5015 | NC | 0.33 | 474 | 795 | NC | NC | NC |
| 5016 | 1.90 | 0.50 | 842 | 1458 | 2216 | 288 | 104681 |
| 5017 | 1.41 | 0.33 | 536 | 760 | 939 | 554 | 272097 |

NC = Not Calculated

What is claimed is:

1. A method of treating osteoporosis in a human subject comprising administering a therapeutically effective amount of abaloparatide with a transdermal patch comprising a plurality of microprojections coated at least in part by a formulation comprising about 300 μg abaloparatide and an excipient comprising one or more $Zn^{2+}$ salts.

2. The method of claim 1, wherein the molar ratio of the one or more $Zn^{2+}$ salts to abaloparatide is from 0.1 to 3.0.

3. The method of claim 1, wherein the molar ratio of the one or more $Zn^{2+}$ salts to abaloparatide is from 1.5 to 2.5.

4. The method of claim 1, wherein the molar ratio of the one or more $Zn^{2+}$ salts to abaloparatide is about 2.2.

5. The method according to claim 1, wherein the transdermal patch comprises from about 85 to about 99% w/w abaloparatide and from about 5 to about 8% w/w $ZnCl_2$.

6. The method according to claim 1, wherein the transdermal patch comprises about 95% w/w abaloparatide and about 6% w/w $ZnCl_2$.

7. The method according to any of the preceding claims, comprising administering the transdermal patch at a site of administration for about 5, 10 or 15 minutes.

8. The method of claim 7, comprising administering the transdermal patch at the site of administration for about 5 minutes.

9. The method of claim 1, comprising administering the transdermal patch at a site of administration for at least 5 minutes.

10. The method of claim 7, wherein the site of administration is an abdomen.

11. The method of claim 7, wherein the site of administration is a thigh.

12. The method of claim 7, wherein the transdermal delivery of abaloparatide is substantially bioequivalent to a subcutaneous delivery of abaloparatide at a dosage of about 80 μg.

13. The method of claim 7, wherein the transdermal delivery of abaloparatide is bioequivalent to a subcutaneous delivery of abaloparatide at a dosage of 80 μg.

14. The method of claim 7, wherein the human subject is a postmenopausal woman.

15. The method of claim 7, wherein the human subject is a postmenopausal woman at a high risk for fracture.

16. The method of claim 7, wherein the human subject is male.

17. The method of claim 7, wherein the osteoporosis is a glucocorticoid induced osteoporosis.

18. The method of claim 7, wherein administering the transdermal patch comprises penetrating the skin to a depth of up to about 700 μm by applying the transdermal patch with an applicator.

* * * * *

UNITED STATES PATENT AND TRADEMARK OFFICE
CERTIFICATE OF CORRECTION

PATENT NO. : 10,980,862 B2
APPLICATION NO. : 16/733779
DATED : April 20, 2021
INVENTOR(S) : Gary Hattersley et al.

Page 1 of 1

It is certified that error appears in the above-identified patent and that said Letters Patent is hereby corrected as shown below:

In the Claims

At Column 44, Claim 6, Line number 42, "95%" should read --94%--.

Signed and Sealed this
First Day of November, 2022

Katherine Kelly Vidal
*Director of the United States Patent and Trademark Office*